US009556462B2

(12) United States Patent
Reed et al.

(10) Patent No.: US 9,556,462 B2
(45) Date of Patent: *Jan. 31, 2017

(54) METHODS OF USING NATURAL AND ENGINEERED ORGANISMS TO PRODUCE SMALL MOLECULES FOR INDUSTRIAL APPLICATION

(71) Applicant: Kiverdi, Inc., Berkeley, CA (US)

(72) Inventors: John S. Reed, Emeryville, CA (US); Itzhak Kurek, San Francisco, CA (US); Henrik Fyrst, Oakland, CA (US); Lisa Dyson, Berkeley, CA (US)

(73) Assignee: Kiverdi, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/214,784

(22) Filed: Mar. 15, 2014

(65) Prior Publication Data

US 2014/0273112 A1 Sep. 18, 2014

Related U.S. Application Data

(60) Provisional application No. 61/791,456, filed on Mar. 15, 2013.

(51) Int. Cl.
C12P 7/64 (2006.01)

(52) U.S. Cl.
CPC .................................... C12P 7/6409 (2013.01)

(58) Field of Classification Search
CPC .................................................. C12P 7/6409
USPC ........................................................ 435/134
See application file for complete search history.

(56) References Cited

U.S. PATENT DOCUMENTS

| | | | |
|---|---|---|---|
| 7,399,855 | B2 | 7/2008 | Frost |
| 7,491,520 | B2 | 2/2009 | Raemakers-Franken et al. |
| 7,799,545 | B2 | 9/2010 | Burgard et al. |
| 8,283,466 | B2 | 10/2012 | Frost |
| 2010/0145003 | A1 | 6/2010 | Frost |
| 2012/0151833 | A1* | 6/2012 | Myllyntausta et al. ........ 44/385 |
| 2013/0078690 | A1 | 3/2013 | Reed et al. |
| 2013/0089899 | A1 | 4/2013 | Kurek et al. |
| 2013/0149755 | A1 | 6/2013 | Reed et al. |
| 2013/0189763 | A1 | 7/2013 | Dalla-Betta et al. |
| 2014/0024091 | A1 | 1/2014 | Reed et al. |
| 2015/0017694 | A1 | 1/2015 | Kurek et al. |
| 2015/0140640 | A1 | 5/2015 | Reed et al. |

FOREIGN PATENT DOCUMENTS

| | | | |
|---|---|---|---|
| NL | WO2011078667 | A2 | 6/2011 |
| WO | WO2011056183 | A1 | 5/2011 |
| WO | WO2011139804 | A2 | 11/2011 |
| WO | WO2013082309 | A1 | 6/2013 |
| WO | WO2013090769 | A2 | 6/2013 |
| WO | WO2013148348 | A1 | 10/2013 |
| WO | WO2014145194 | A3 | 9/2014 |
| WO | WO2015027209 | A2 | 2/2015 |

OTHER PUBLICATIONS

Yano et al. Carbon Monoxide Utilization of an Extremely Oligotrophic Bacterium, Rhodococcus Erythropolis N9T-4; Journal of Bioscience and Bioengineering, vol. 114, No. 1 (May 4, 2012) pp. 53-55.*
Sharma et al. Biodegradation and Conversion of Alkanes and Crude Oil by a *Marine Rhodococcus* sp.; Biodegradation, vol. 11 (2000) pp. 289-294.*
Alvarez et al. Accumulation of Storage Lipids in Species of *Rhodococcus* and *Nocardia* and Effect of Inhibitors and Polyethylene Glycol; Fett/Lipid, vol. 99 (1997) pp. 239-246.*
Adrio, J., et al., Recombinant Organisms for Production of Industrial Products, Bioengineered Bugs, 2010; 1(2): 116-131.
Piel, J., et al., Cloning, Sequencing and Analysis of the Enterocin Biosynthesis Gene Cluster from the Marine Isolate 'Streptomyces Maritimus':Evidence for the Derailment of an Aromatic Polyketide Synthase, Chemistry & Biology, 2000;7(12):943-955.
McLeod, M., et al., The Complete Genome of *Rhodoccocus* sp. RHA1 Provides Insights into a Catabolic Powerhouse, Proc. Natl. Acad. Sci., 2006; 103(42)15582-15587.
Senkus, M., Recovery of 2,3-Butanediol Produced by Fermentation, Industrial and Engineering Chemistry, 1946; 38 (9): 913-916.
Qureshi, A., et al., Cloning and Expression of Mutations Demonstrating Intragenic Complementation in mut0 Methylmalonic Aciduria, J. Clin. Invest., 1994; 93:1812-1819.
Dahiyat, B. and Mayo, S. De Novo Protein Design: Fully Automated Sequence Selection, Science, 1997; 278:82-87.
Kunkel, T., et al., Rapid and Efficient Site-specific Mutagenesis Without Phenotypic Selection, Proc. Nat. Acad Sci. U.S.A., 1985; 82:488-492.
Kalinowski, J., et al., Genetic and Biochemical Analysis of the Aspartokinase from Corynebacterium gluticum, Molecular Microbiology 1991; 5(5):1197-1204.
Patek, M., et al., Identification and Transcriptional Analysis of the dapB-ORF2-dapA-ORF4 Operon of Corynebacterium glutamicum, Encoding Two Enzymes Involved in L-lysine Synthesis, Biotechnology Letters 1997; 19 (11): 1113-1117.
Vrljic, M, et al., A New Type of Transporter with a New Type of Cellular Function: L-Lysine Export from Corynebacterium Glutamicum, Molecular Microbiology, 1996; 22(5):815-826.
Johnson, J., et al., Genetic Evidence for the Expression of ATP- and GTP-specific Succinyl-CoA Synthetases in Multicellular Eucaryotes, Journal of Biological Chemistry, 1998; 273(42):27580-27586.
Holder, J., et al., Comparative and Functional Genomics of Rhodococcus Opacus PD630 for Biofuels Development, PLoS Genetics, 2011; 7(9): 1-18.

(Continued)

Primary Examiner — Scott Long
Assistant Examiner — Paul Martin
(74) Attorney, Agent, or Firm — Jill A. Jacobson

(57) ABSTRACT

Methods are provided for producing omega-7 fatty acids from feedstock that includes syngas using *Rhodococcus* microorganisms. The syngas feedstock includes at least one of CO or a mixture of $CO_2$ and $H_2$, and the methods include introducing syngas into a bioreactor, where chemoautotrophic *Rhodococcus* microorganisms convert the gaseous feedstock into omega-7 fatty acids, such as palmitoleic acid and vaccenic acid.

7 Claims, 6 Drawing Sheets

(56) References Cited

OTHER PUBLICATIONS

Schneider, J., et al., Putrescine Production by Engineered Corynebacterium glutamicum, Appl Microbiol Biotechnol., 2010; 88:859-868.
Mooney, A., et al., Microbial Degradation of Styrene: Biochemistry, Molecular Genetics, and Perspectives for Biotechnological Applications, Appl. Microbiol. Biotechnol., 2006; 72:1-10.
Alberts, et al., Cell Breakage and Fractionation; Part 2 [online]. Access Excellence About Biotech. 1998[retrieved on Aug. 26, 2014]. Retrieved from the Internet: <URL: http://www.accessexcellence.org/RC/VL/GG/garland_PDFs/Panel_5.04b.pdf, p. 1; figure 1.
Tsitko, I., et al. Effect of Aromatic compounds on Cellular Fatty Acid Composition of Rhoddoccus opacus. Applied and Environmental Microbiology. 1999; 65(2):853-855.
Pedersen, D., et al., Dry Column Vaccum Chromatography [online]. Synthesis. 2001. [retrieved on Aug. 26, 2014]. Retrieved from the Internet: <URL: https://www.erowid.org/archive/rhodium/chemistiy/equipment/drycolumn.vacuum.chromatography.html; pp. 1-5; p. 4, line 13; paragraph 2.

* cited by examiner

FIGURE 4

| FA | Name | | C# | A Neutral ug | B Neutral ug | A Phosph ug | B Phosph ug | A Glyco ug | B Glyco ug | A FFA ug | B FFA ug |
|---|---|---|---|---|---|---|---|---|---|---|---|
| C14:0 | myristic acid | | 14 | 2.01 | | | | | | | |
| C14:0 | 12-methyltetradecanoic acid | anteiso-pentadecanoic acid | 15 | | | 3.15 | 6.46 | 12.57 | 64.76 | | |
| C14:0 | 13-methyltetradecanoic acid | iso-pentadecanoic acid | 15 | | | 4.42 | 4.96 | 3.74 | | | |
| C15:0 | pentadecanoic acid | | 15 | 3.24 | | | | | | | |
| C15:0 | 14-methylpentadecanoic acid | | 16 | | | | | | | 14.73 | 4.22 |
| C16:0 | palmitic acid | | 16 | 26.2 | 3.21 | 29.66 | 14.34 | 20.37 | 43.73 | | |
| C16:1n7 | palmitoleic acid | | 16 | 16.03 | 2.57 | 16.27 | 7.95 | 2.27 | 2.36 | | |
| C16:0 | 10-methylhexadecanoic acid | | 17 | 2.29 | | | | | | | |
| C16:0 | 14-methylhexadecanoic acid | anteiso-peptadecanoic acid | 17 | | | | | | | | |
| C16:0 | 15-methylhexadecanoic acid | iso-peptadecanoic acid | 17 | 2.1 | | 6.12 | 3.41 | 13.71 | 67.25 | | |
| C16:0 | cyclopropane-hexadecanoic acid | | 17 | | | | | | 4.06 | | |
| C17:0 | margaric acid | | 17 | 5.34 | | | | | | | |
| C17:0 | 10-methylheptadecanoic acid | | 17 | 2.32 | | | 2.05 | | 2.59 | | |
| C17:0 | 16-methylheptadecanoic acid | | 18 | 1.7 | | 2.28 | | 6.61 | | | |
| C18:0 | stearic acid | iso-octadecanoic acid | 18 | 4.5 | | 4.55 | 3.67 | 9.63 | 8.86 | | |
| C18:0 | 3-hydroxyoctadecanoic acid | | 18 | | 6.67 | | | | | | |
| C18:0 | 9,10-dichlorooctadecatoic acid | | 18 | | | | | | 6.94 | | |
| C18:1n7 | vaccenic acid | | 18 | 25.69 | 3.42 | 64.62 | 49.75 | 43.35 | 74.14 | | |
| C18:1n9 | oleic acid | | 18 | 15.64 | | 4.55 | | | | | |
| C18:1n9 | elaidic acid | | 18 | | | | | | 3.39 | 5.21 | |
| C18:2n6,9 | linoleic acid | | 18 | | | | | 2.79 | | 4.22 | |
| C18:3n3,6,9 | alpha-linoleinic | | 18 | | | | | 2.91 | | | |
| C18:0 | 10-methyloctadecanoid acid | | 19 | 14.09 | | 14.22 | 6.51 | | | | |
| C20:0 | arachidic acid | | 20 | | | | | 4.75 | 5.95 | | |
| C20:0 | Bicyclo-eicosane | | 20 | | | | | 3.62 | | | |
| C20:1 | eicosenoic acid | | 20 | 2.71 | | | | | 4.97 | | |
| C22:0 | behenic acid | | 22 | | 2.17 | | | 2.62 | | | |
| Total (ug) | | | | 123.86 | 18.04 | 149.84 | 101.81 | 128.94 | 289 | 24.16 | 4.22 |

METHODS OF USING NATURAL AND ENGINEERED ORGANISMS TO PRODUCE
SMALL MOLECULES FOR INDUSTRIAL
APPLICATION

RELATED APPLICATIONS

This application claims the benefit under 35 U.S.C. 119(e) of U.S. Provisional Application Ser. No. 61/791,456, entitled "Methods of using natural and engineered organisms to produce small molecules for industrial application," filed on Mar. 15, 2013, the entire disclosure of which is incorporated by reference herein in its entirety.

FIELD OF THE INVENTION

The disclosure relates to methods of producing small molecules for industrial application using natural organisms and engineered organisms.

BACKGROUND OF THE INVENTION

Microorganisms have been used for a variety of industrial applications. Genetic engineering of microorganisms has increased their potential, such as by manipulating enzymatic pathways, or creating new enzymatic pathways, within cells (Adrio et al. (2010) Bioeng. Bugs. 1(2):116-131).

SUMMARY OF INVENTION

The instant invention provides methods of using engineered organisms and natural organisms to produce small molecules for industrial application.

Aspects of the invention relate to methods for the production of omega-7 fatty acids from feedstock comprising syngas and containing at least one of CO or a mixture of $CO_2$ and $H_2$, the process comprising passing syngas to a bioreactor for contact therein with *Rhodococcus* microorganisms.

In some embodiments, methods further comprise a separation step wherein a cell mass is separated from a supernatant by centrifugation to create a biomass pellet. In some embodiments, the biomass pellet contains omega-7 fatty acids. In some embodiments, the omega-7 fatty acids comprise palmitoleic acid (C16:1) and vaccenic acid (C18:1).

In some embodiments, methods further comprise an extraction step wherein the supernatant is discarded and the biomass pellet is applied to a Silica-60 column. In some embodiments, the extraction step further includes eluting lipids with an organic solvent. In some embodiments, the organic solvent is selected from a group comprising: hexane, chloroform, isopropanol, methanol, and acetone. In some embodiments, the microorganism is a *Rhodococcus opacus* strain.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The accompanying drawings are not intended to be drawn to scale. The figures are illustrative only and are not required for enablement of the disclosure. For purposes of clarity, not every component may be labeled in every drawing. In the drawings:

FIG. 4 presents results from gas chromatography-mass spectrometry analysis of fatty acid methyl esters produced by *Rhodococcus opacus*.

DETAILED DESCRIPTION OF THE INVENTION

Figure 1:
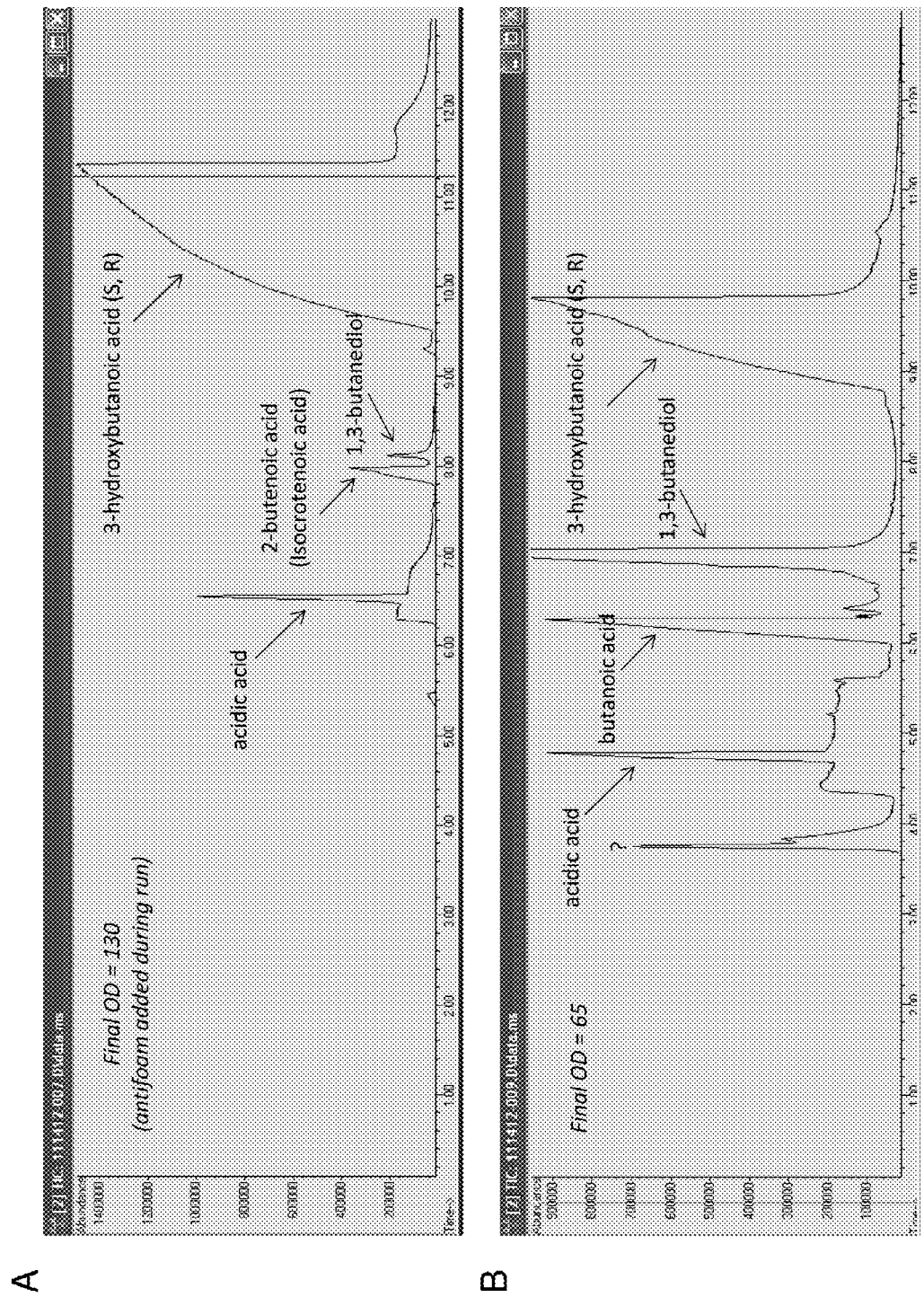
FIGS. 1A and 1B show gas chromatography-mass spectrometry analysis of secreted bacterial fermentation products from *C. necator*.

In some embodiments, the instant invention provides a method of using a natural strain microorganism that grows on carbon-containing gas such as syngas, producer gas, $CO_2$, carbon monoxide and mixtures of the same containing hydrogen gas; and/or C1 compounds, gaseous or liquid, including but not limited to methanol or methane, to produce and/or secrete amino containing compounds including amino acids by combining the natural microorganism and said carbon-containing gas in a bioreactor or solution. In some non-limiting embodiments the microorganism is *Cupriavidus necator* DSM 531 or DSM 541 (Table 2). In some non-limiting embodiments the microorganism is *Ralstonia eutropha* N-1, DSM 13513.

In some embodiments, the amino containing compounds secreted and/or produced include glutamic acid, sarcosine, serine, glycine, alanine, threonine, valine, isoleucine, ornithine, histidine, arginine, phenylalanine, lysine, tyrosine, cytosine, asparatic acid, glutamine, proline, leucine, tryptophan, methionine, β-alanine, S-adenosylmethionine, S-adenosylhomocysteine, methionine sulfoxide and putrescine (Table 2).

In some embodiments, the instant invention provides for an engineered microorganism that converts a carbon-containing gas such as syngas, producer gas, CO2, carbon monoxide and mixtures of the same containing hydrogen gas; and/or C1 compounds, gaseous or liquid, including but not limited to methanol or methane, into amino containing compounds and encodes one or more genes useful for the production of amino containing compounds.

In some embodiments, the instant invention provides for a method of producing amino containing compounds by combining, in a bioreactor or solution, a carbon-containing gas and an engineered microorganism that converts a carbon-containing gas such as syngas, producer gas, CO2, carbon monoxide and mixtures of the same containing hydrogen gas; and/or C1 compounds, gaseous or liquid, including but not limited to methanol or methane, into amino containing compounds and encodes one or more genes useful for the production of amino containing compounds. (Table 2).

In some embodiments, the instant invention provides for a method of producing styrene by combining, in a bioreactor or solution, one or more enzymes useful for the production of amino containing compounds, a carbon-containing gas, and an engineered or natural microorganism that converts a carbon-containing gas such as syngas, producer gas, CO2, carbon monoxide and mixtures of the same containing hydrogen gas; and/or C1 compounds, gaseous or liquid, including but not limited to methanol or methane, into the precursors utilized by the enzymes to produce amino containing compounds. (Table 2).

In some embodiments, the instant invention provides for a natural or engineered microorganism that converts a carbon-containing gas such as syngas, producer gas, CO2, carbon monoxide and mixtures of the same containing hydrogen gas; and/or C1 compounds, gaseous or liquid, including but not limited to methanol or methane, into putrescine and encodes one or more genes including but not limited to the enzyme ornithine decarboxylase. In some non-limiting embodiments the microorganism is *Cupriavidus necator* DSM 531 or DSM 541 (Table 2). In some non-limiting embodiments the microorganism is *Ralstonia eutropha* N-1, DSM 13513.

In some embodiments, the instant invention provides for a method of producing putrescine by combining, in a bioreactor or solution, a carbon-containing gas and a natural or engineered microorganism that converts a carbon-containing gas such as syngas, producer gas, CO2, carbon monoxide and mixtures of the same containing hydrogen gas; and/or C1 compounds liquid or gaseous including but not limited to methanol or methane, into putrescine and encodes one or more genes including but not limited to the enzyme ornithine decarboxylase. In some non-limiting embodiments the microorganism is *Cupriavidus necator* DSM 531 or DSM 541. In some non-limiting embodiments the microorganism is *Ralstonia eutropha* N-1, DSM 13513. In some embodiments, the instant invention further provides for the additional step of adding adipic acid to the putrescine to produce nylon-4,6.

In some embodiments, the instant invention provides for a method of producing putrescine by combining, in a bioreactor or solution, a carbon-containing gas and a natural strain microorganism that converts a carbon-containing gas such as syngas, producer gas, CO2, carbon monoxide and mixtures of the same containing hydrogen gas; and/or C1 compounds liquid or gaseous including but not limited to methanol or methane, into putrescine. In some non-limiting embodiments the microorganism is *Cupriavidus necator* DSM 531 or DSM 541 (Table 2). In some non-limiting embodiments the microorganism is *Ralstonia eutropha* N-1, DSM 13513. In some embodiments, the instant invention further provides for the additional step of adding adipic acid to the putrescine to produce nylon-4,6.

In some embodiments, the instant invention provides for a method of producing putrescine by combining, in a bioreactor or solution, ornithine decarboxylase, a carbon-containing gas, and an engineered or natural microorganism that converts a carbon-containing gas such as syngas, producer gas, CO$_2$, carbon monoxide and mixtures of the same containing hydrogen gas; and/or C1 compounds liquid or gaseous including but not limited to methanol or methane, into ornithine. In some non-limiting embodiments the microorganism is *Cupriavidus necator* DSM 531 or DSM 541 (Table 2). In some non-limiting embodiments the microorganism is *Ralstonia eutropha* N-1, DSM 13513. In some embodiments, the instant invention further provides for the additional step of converting ornithine into putrescine through the catalytic action of the enzyme ornithine decarboxylase. In some embodiments, the instant invention further provides for the additional step of adding adipic acid to the putrescine to produce nylon-4,6.

In one embodiment, the instant invention provides a composition containing an engineered or natural microorganism that converts a carbon-containing gas such as syngas, producer gas, CO2, carbon monoxide and mixtures of the same containing hydrogen gas; and/or C1 compounds, gaseous or liquid, including but not limited to methanol or methane, into lysine. In some non-limiting embodiments the microorganism is *Cupriavidus necator* DSM 531 or DSM 541 (Table 2). In some non-limiting embodiments the microorganism is *Ralstonia eutropha* N-1, DSM 13513.

In some embodiments, the instant invention further provides for the engineered microorganism that converts a carbon-containing gas such as syngas, producer gas, CO2, carbon monoxide and mixtures of the same containing hydrogen gas; and/or C1 compounds, gaseous or liquid, including but not limited to methanol or methane, into lysine and encodes one or more genes including but not limited to, a carbon nitrogen lyase, an oxidoreductase, α-β-enoate reductase (EC 1.3.1.-) and/or an amidohydrolase (EC 3.5.2.-).

In some embodiments, the instant invention further provides for the engineered microorganism that converts a carbon-containing gas such as syngas, producer gas, CO$_2$, carbon monoxide and mixtures of the same containing hydrogen gas; and/or C1 compounds, gaseous or liquid, including but not limited to methanol or methane, into tyrosine and encodes one or more genes including but not limited to, tyrosine phenol lyase (EC 4.1.99.2). In some embodiments the reaction of tyrosine catalyzed by tyrosine phenol lyase results in the production of phenol.

In some embodiments, the instant invention provides for a method of producing phenol by combining, in a bioreactor or solution, one or more enzymes including but not limited to tyrosine ammonium lyase and, a carbon-containing gas, and an engineered or natural microorganism that converts a carbon-containing gas such as syngas, producer gas, CO$_2$, carbon monoxide and mixtures of the same containing hydrogen gas; and/or C1 compounds, gaseous or liquid, including but not limited to methanol or methane, into a tyrosine. (Table 2). In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention further provides for a method of producing caprolactam by combining the engineered microorganism that converts a carbon-containing gas such as syngas, producer gas, CO$_2$, carbon monoxide and mixtures of the same containing hydrogen gas; and/or C1 compounds, gaseous or liquid, including but not limited to methanol or methane, into lysine, with said carbon-containing gas and an enzyme encoded into the microorganism or supplied to the organism including but not limited to α-β-enoate reductase and/or amidohydrolase in a bioreactor or solution. In some embodiments the caprolactam is used to produce nylon-6 using chemical conversion processes known to one well versed in the art and science.

In some embodiments, the instant invention further provides for a method of producing caprolactam by combining the engineered microorganism that converts a carbon-containing gas such as syngas, producer gas, CO$_2$, carbon monoxide and mixtures of the same containing hydrogen gas; and/or C1 compounds, gaseous or liquid, including but not limited to methanol or methane, into tyrosine (Table 2), with said carbon-containing gas and an enzyme encoded into the microorganism or supplied to the organism including but not limited to tyrosine phenol lyase (EC 4.1.99.2) in a bioreactor or solution. In some embodiments the action of tyrosine phenol lyase on tyrosine produces phenol. In some embodiments the phenol is separated from the aqueous broth using methods known to one well versed in the art and science. In some embodiments commercial technologies that have been developed for the recovery of phenol from an aqueous process stream are utilized for the separation of phenol from the aqueous broth. In some non-limiting embodiments a pervaporation process is used to separate phenol from the aqueous broth. In some non-limiting embodiments pervaporation is followed by liquid-liquid phase separation to produce a higher purity phenol output. In some embodiments the phenol product resulting from pervaporation followed by liquid-liquid phase separation is over 72 wt % phenol. In some embodiments the aqueous residual from pervaporation followed by liquid-liquid phase separation is 7-8 wt % phenol, which is recycled to the feed stream entering the pervaporation step. In some embodiments the phenol-rich liquid produced through pervaporation is further purified by distillation using methods known to one well versed in the art and science. In some other non-limiting embodiments solvent extraction is used to separate phenol from the aqueous broth. In some non-limiting embodiments the cells are filtered from the aqueous broth using methods known to one well versed in the art and science and are recycled into the bioreactor prior to the aqueous broth entering solvent. In some embodiments Methylisobutylketone (MIBK), is used as an extracting agent to extract phenol from the aqueous broth in an extraction column. In some embodiments the phenol is further purified and the MIBK recovered for further extractions using a distillation column. In some embodiments the stream of aqueous broth after having phenol removed by solvent extraction flowing out of the solvent extraction unit may carry traces of the extracting agent. In some embodiments the traces of extracting agent are recovered in a stripper column. In some embodiments the MIBK/water azeotrope accumulates at the head of the stripper column, where it is separated in the separator into the light MIBK phase and the heavy water phase. In some embodiments the recovered MIBK is used for additional solvent extraction. In some embodiments the recovered phenol is converted to cyclohexanone using methods known to one well versed in the art and science. In some embodiments phenol is converted to cyclohexanone using a commercial process for the hydrogenation of phenol to cyclohexanone. In some non-limiting embodiments the hydrogenation of phenol occurs in the vapor phase. In some non-limiting embodiments the hydrogenation of phenol occurs in the liquid phase. In some non-limiting embodiments the hydrogenation of phenol to cyclohexanone utilizes a palladium based catalyst.

In some non-limiting embodiments vapor phase phenol hydrogenation is conducted at temperatures from 140-170° C. and a pressure slightly above atmospheric. In some embodiments the conversion of phenol to cyclohexanone occurs in a single reactor. In some embodiments over a 90% yield in cyclohexanone is achieved in a single reactor. In some non-limiting embodiments a nickel-type catalyst is used instead of a palladium based catalyst. In some non-limiting embodiments the conversion of phenol to cyclohexanone has two distinct reaction steps, 1) full hydrogenation to cyclohexanol followed by 2) dehydrogenation to cyclohexanone. In some non-limiting embodiments a liquid-phase hydrogenation of phenol to cyclohexanone is performed at temperatures below the atmospheric boiling point. In some non-limiting embodiments a liquid-phase hydrogenation of phenol to cyclohexanone is performed at temperatures from 140-150° C. In some non-limiting embodiments over 99% yield of cyclohexanone is achieved at greater than or equal to 90% conversion. In some embodiments the cyclohexanone produced is converted to caprolactam using chemical conversion processes known to one well versed in the art and science. In some embodiments the cyclohexanone is converted to the oxime by reaction with hydroxylamine which in turn rearranges to form caprolactam in the presence of a sulfuric acid catalyst. In some embodiments the caprolactam is used to produce nylon-6 using chemical conversion processes known to one well versed in the art and science. In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention further provides for a method of producing caprolactam by combining the engineered or natural microorganism that converts a carbon-containing gas such as syngas, producer gas, $CO_2$, carbon monoxide and mixtures of the same containing hydrogen gas; and/or C1 compounds, gaseous or liquid, including but not limited to methanol or methane, into lysine (Table 2), recovering lysine from the microbial broth using methods known in the art and science of microbial lysine production, and using high temperatures and alcohol as described in and specifically incorporated by reference from U.S. Pat. No. 8,283,466 (U.S. patent application Ser. No. 12/527,848) to convert the lysine into caprolactam. In some embodiments the caprolactam is used to produce nylon-6 using chemical conversion processes known to one well versed in the art and science. In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention further provides for a method of producing caprolactam by combining the engineered or natural microorganism that converts a carbon-containing gas such as syngas, producer gas, CO2, carbon monoxide and mixtures of the same containing hydrogen gas; and/or C1 compounds, gaseous or liquid, including but not limited to methanol or methane, into lysine (Table 2), with said carbon-containing gas and a chemical catalyst as described in and specifically incorporated by reference from U.S. Pat. No. 7,399,855 used to convert the lysine into caprolactam. In some embodiments the caprolactam is used to produce nylon-6 using chemical conversion processes known to one well versed in the art and science. In some non-limiting embodiments the microorganism is *Cupriavidus necator* DSM 531 or DSM 541. In some non-limiting embodiments the microorganism is *Ralstonia eutropha* N-1, DSM 13513.

In an alternative embodiment, the instant invention provides for an engineered or natural microorganism that converts a carbon-containing gas such as syngas, producer gas, $CO_2$, carbon monoxide and mixtures of the same containing hydrogen gas; and/or C1 compounds, gaseous or liquid, including but not limited to methanol or methane, into phenylalanine (Table 2). In some embodiments the engineered or natural microorganism encodes one or more genes including but not limited to enzymes in the Shikimate pathway including but not limited to chorismate synthase. In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for a method of producing phenylalanine by combining, in a bioreactor or solution, a carbon-containing gas and an engineered or natural microorganism that converts a carbon-containing gas such as syngas, producer gas, CO2, carbon monoxide and mixtures of the same containing hydrogen gas; and/or C1 compounds, gaseous or liquid, including but not limited to methanol or methane, into phenylalanine (Table 2), and in some embodiments it encodes one or more genes including but not limited to enzymes in the Shikimate pathway including but not limited to chorismate synthase. In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for a method of producing phenylalanine by combining, in a bioreactor or solution, one or more enzymes including but not limited to enzymes in the Shikimate pathway including but not limited to chorismate synthase, a carbon-containing gas, and an engineered or natural microorganism that converts a carbon-containing gas such as syngas, producer gas, CO2, carbon monoxide and mixtures of the same containing hydrogen gas; and/or C1 compounds, gaseous or liquid, including but not limited to methanol or methane, into a precursor to phenylalanine that the enzymes use. (Table 2). In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for an engineered microorganism that converts a carbon-containing gas such as syngas, producer gas, $CO_2$, carbon monoxide and mixtures of the same containing hydrogen gas; and/or C1 compounds, gaseous or liquid, including but not limited to methanol or methane, into cinnamic acid and encodes one or more genes including but not limited to the enzyme phenylalanine ammonium lyase (EC 4.3.1.24).

In some embodiments, the instant invention provides for a method of producing cinnamic acid by combining, in a bioreactor or solution, a carbon-containing gas and an engineered microorganism that converts a carbon-containing gas such as syngas, producer gas, $CO_2$, carbon monoxide and mixtures of the same containing hydrogen gas; and/or C1 compounds, gaseous or liquid, including but not limited to methanol or methane, into cinnamic acid and encodes one or more genes including but not limited to the enzyme phenylalanine ammonium lyase. In some non-limiting embodiments the phenylalanine ammonium lyase gene is taken from *Streptomyces maritimus* (Piel et al., 2000).

In some embodiments, the instant invention provides for a method of producing cinnamic acid by combining, in a bioreactor or solution, one or more enzymes including but not limited to phenylalanine ammonium lyase, a carbon-containing gas, and an engineered or natural microorganism that converts a carbon-containing gas such as syngas, producer gas, CO2, carbon monoxide and mixtures of the same containing hydrogen gas; and/or C1 compounds, gaseous or liquid, including but not limited to methanol or methane, into a phenylalanine. (Table 2). In some embodiments the phenylalanine is converted to cinnamic acid. In some non-limiting embodiments the phenylalanine ammonium lyase enzyme is taken from *Streptomyces maritimus* (Piel et al., 2000). In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for a method of producing cinnamic acid by combining, in a bioreactor or solution, one or more enzymes including but not limited to tyrosine ammonium lyase and, a carbon-containing gas, and an engineered or natural microorganism that converts a carbon-containing gas such as syngas, producer gas, $CO_2$, carbon monoxide and mixtures of the same containing hydrogen gas; and/or C1 compounds, gaseous or liquid, including but not limited to methanol or methane, into a tyrosine. In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for an engineered microorganism that converts a carbon-containing gas such as syngas, producer gas, $CO_2$, carbon monoxide and mixtures of the same containing hydrogen gas; and/or C1 compounds, gaseous or liquid, including but not limited to methanol or methane, into styrene and encodes one or more genes including but not limited to the enzyme cinnamic acid decarboxylase. In some embodiments two or more genes are encoded including phenylalanine ammonium lyase and cinnamic acid decarboxylase. In some embodiments phenylalanine is converted to cinnamic acid. In some embodiments cinnamic acid is converted to styrene. In some embodiments phenylalanine ammonium lyase (EC 4.3.1.24) activity converts phenylalanine into cinnamic acid. In some embodiments cinnamic acid is further converted into styrene through a decarboxylation step catalyzed by enzymes belonging to a family of oxalate decarboxylases (EC 4.1.1.2). In some non-limiting embodiments the genes that encode phenylalanine ammonium lyase (EC 4.3.1.24) are taken from *Streptomyces maritimus* [Piel et al., 2000]. In some non-limiting embodiments the genes that encode oxylate decarboxylase are taken from *Rhodococcus jostii* RHA1 (McLeod et al., 2006). In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for a method of producing styrene by combining, in a bioreactor or solution, a carbon-containing gas and an engineered microorganism that converts a carbon-containing gas such as syngas, producer gas, $CO_2$, carbon monoxide and mixtures of the same containing hydrogen gas; and/or C1 compounds, gaseous or liquid, including but not limited to methanol or methane, into styrene and encodes one or more genes including but not limited to the enzyme cinnamic acid decarboxylase. In some embodiments two or more genes are encoded including phenylalanine ammonium lyase and cinnamic acid decarboxylase. In some embodiments phenylalanine is converted to cinnamic acid. In some embodiments cinnamic acid is converted to styrene. In some embodiments phenylalanine ammonium lyase (EC 4.3.1.24) activity converts phenylalanine into cinnamic acid. In some embodiments cinnamic acid is further converted into styrene through a decarboxylation step catalyzed by enzymes belonging to a family of oxalate decarboxylases (EC 4.1.1.2). In some non-limiting embodiments the genes that encode phenylalanine ammonium lyase (EC 4.3.1.24) are taken from *Streptomyces maritimus* (Piel et al., 2000). In some non-limiting embodiments the genes that encode oxylate decarboxylase are taken from *Rhodococcus jostii* RHA1 (McLeod et al., 2006). In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for a method of producing styrene by combining, in a bioreactor or solution, one or more enzymes including but not limited to cinnamic acid decarboxylase, a carbon-containing gas, and an engineered or natural microorganism that converts a carbon-containing gas such as syngas, producer gas, CO2, carbon monoxide and mixtures of the same containing hydrogen gas; and/or C1 compounds, gaseous or liquid, including but not limited to methanol or methane, into a cinnamic acid. In some embodiments the cinnamic acid is converted to styrene. In some embodiments cinnamic acid is converted into styrene through a decarboxylation step catalyzed by enzymes belonging to a family of oxalate decarboxylases (EC 4.1.1.2). In some non-limiting embodiments the oxalate decarboxylase enzyme that decarboxylates the cinnamic acid to produce styrene is encode by a genes taken from *Rhodococcus jostii* RHA1 (McLeod et al., 2006). In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for an engineered microorganism that converts a carbon-containing gas such as syngas, producer gas, CO2, carbon monoxide and mixtures of the same containing hydrogen gas; and/or C1 compounds, gaseous or liquid, including but not limited to methanol or methane, into tyrosine and encodes one or more genes including but not limited to the enzyme phenylalanine hydroxylase. In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for a method of producing tyrosine by combining, in a bioreactor or solution, a carbon-containing gas and an engineered or natural microorganism that converts a carbon-containing gas such as syngas, producer gas, CO2, carbon monoxide and mixtures of the same containing hydrogen gas; and/or C1 compounds, gaseous or liquid, including but not limited to methanol or methane, into tyrosine and encodes one or more genes including but not limited to the enzyme phenylalanine hydroxylase (Table 2). In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for a method of producing tyrosine by combining, in a bioreactor or solution, one or more enzymes including but not limited to phenylalanine hydroxylase, a carbon-containing gas, and an engineered or natural microorganism that converts a carbon-containing gas such as syngas, producer gas, CO2, carbon monoxide and mixtures of the same containing hydrogen gas; and/or C1 compounds, gaseous or liquid, including but not limited to methanol or methane, into a phenylalanine (Table 2). In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for an engineered microorganism that converts a carbon-containing gas such as syngas, producer gas, CO2, carbon monoxide and mixtures of the same containing hydrogen gas; and/or C1 compounds, gaseous or liquid, including but not limited to methanol or methane into phenol and encodes one or more genes including but not limited to the enzyme tyrosine phenol lyase. In some embodiments tyrosine is converted into phenol. In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for a method of producing phenol by combining, in a bioreactor or solution, a carbon-containing gas and an engineered microorganism that converts a carbon-containing gas such as syngas, producer gas, CO2, carbon monoxide and mixtures of the same containing hydrogen gas; and/or C1 compounds, gaseous or liquid, including but not limited to methanol or methane, into phenol and encodes one or more genes including but not limited to the enzyme tyrosine phenol lyase. In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for a method of producing phenol by combining, in a bioreactor or solution, one or more enzymes including but not limited to tyrosine phenol lyase, a carbon-containing gas, and an engineered or natural microorganism that converts a carbon-containing gas such as syngas, producer gas, CO2, carbon monoxide and mixtures of the same containing hydrogen gas; and/or C1 compounds, gaseous or liquid, including but not limited to methanol or methane, into a tyrosine. In some embodiments tyrosine is converted to phenol. In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for a method of producing benzene by first producing phenol by combining, in a bioreactor or solution, a carbon-containing gas and an engineered microorganism that converts a carbon-containing gas such as syngas, producer gas, CO2, carbon monoxide and mixtures of the same containing hydrogen gas; and/or C1 compounds, gaseous or liquid, including but not limited to methanol or methane, into phenol and encodes one or more genes including but not limited to the enzyme tyrosine phenol lyase; then by converting phenol into benzene chemically by one or more methods known to one well versed in the art and science including but not limited to combining heat, zinc metal and phenol to produce benzene according to well established and known protocols. In some embodiments, the instant invention further provides for a method of converting the benzene produced by said method into caprolactam known to one well versed in the art and science through commercial chemical processes for the hydrogenation of benzene into cyclohexane, then oxidizing cyclohexane into cyclohexanol which is dehydrogenated into cyclohexanone which in some embodiments is converted into caprolactam through the Beckman rearrangement. In an alternative embodiment, the instant invention further provides for a method of converting said benzene into teraphthalic acid through commercial chemical processes well known to one well versed in the art and science including but not limited to by converting benzene through dehydrocyclodimerization into xylene, which is then converted by oxidation into teraphthalic acid. In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for a method of producing cyclohexanone by combining, in a bioreactor or solution, a carbon-containing gas, and an engineered or natural microorganism that converts a carbon-containing gas such as syngas, producer gas, $CO_2$, carbon monoxide and mixtures of the same containing hydrogen gas; and/or C1 compounds, gaseous or liquid, including but not limited to methanol or methane, into a phenol, then converting the phenol into cyclohexanone chemically through hydrogenation, a commercial chemical process well known to one well versed in the art and science. In some embodiments the cyclohexanone is converted into caprolactam through, a commercial chemical process well known to one well versed in the art and science known as the Beckman rearrangement. In some embodiments the caprolactam is a precursor for nylon-6. In some embodiments it encodes one or more genes including but not limited to the enzyme tyrosine phenol lyase. In some embodiments tyrosine is converted to phenol. In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for an engineered microorganism that converts a carbon-containing gas such as syngas, producer gas, $CO_2$, carbon monoxide and mixtures of the same containing hydrogen gas; and/or C1 compounds, gaseous or liquid, including, but not limited to methanol or methane, into caprolactam and encodes one or more genes including but not limited to the enzyme carbon nitrogen lyase, α-β-enoate reductase, amidohydrolase. In some embodiments the caprolactam is used as a precursor for the production of nylon-6. In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for a method of producing caprolactam by combining, in a bioreactor or solution, a carbon-containing gas and an engineered microorganism that converts a carbon-containing gas such as syngas, producer gas, $CO_2$, carbon monoxide and mixtures of the same containing hydrogen gas; and/or C1 compounds, gaseous or liquid, including but not limited to methanol or methane, into caprolactam and encodes one or more genes including but not limited to the enzyme carbon nitrogen lyase, α-β-enoate reductase, amidohydrolase. In some embodiments the caprolactam is used as a precursor for nylon-6. In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for a method of producing caprolactam by combining, in a bioreactor or solution, one or more enzymes including but not limited to Carbon nitrogen lyase, α-β-enoate reductase, amidohydrolase, a carbon-containing gas, and an engineered or natural microorganism that converts a carbon-containing gas such as syngas, producer gas, $CO_2$, carbon monoxide and mixtures of the same containing hydrogen gas; and/or C1 compounds, gaseous or liquid, including but not limited to methanol or methane, into a lysine (Table 2). In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for a method of producing caprolactam by combining, in a bioreactor or solution, a carbon-containing gas, and an engineered or natural microorganism that converts a carbon-containing gas such as syngas, producer gas, $CO_2$, carbon monoxide and mixtures of the same containing hydrogen gas; and/or C1 compounds, gaseous or liquid, including but not limited to methanol or methane, into a cyclohexanone, then performing the acid induced Beckman rearrangement on the cyclohexanone produced. In some embodiments the cyclohexanone is converted to caprolactam. In some embodiments the caprolactam is converted to nylon-6. In some non-limiting embodiments the microorganism is *Cupriavidus necator* DSM 531 or DSM 541. In some non-limiting embodiments the microorganism is *Ralstonia eutropha* N-1, DSM 13513.

Figure 2:
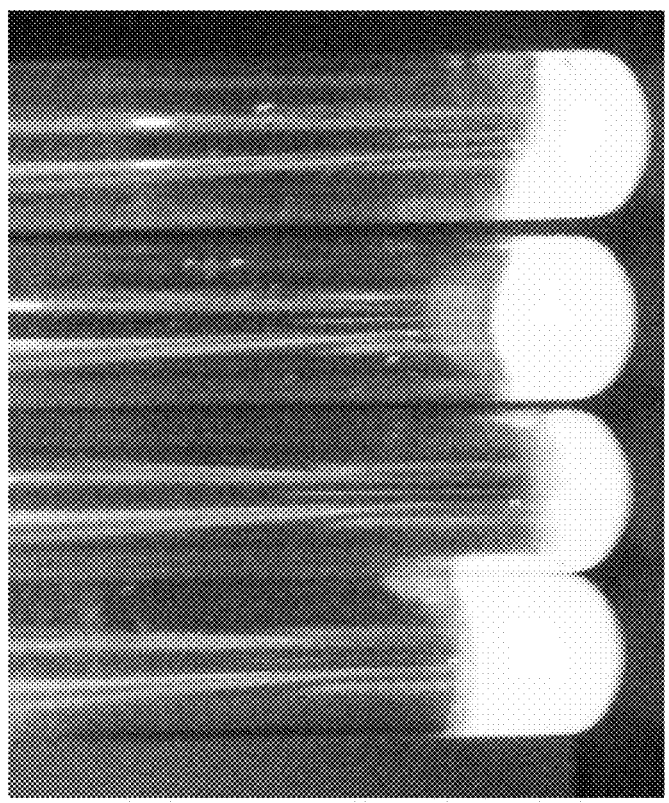
FIG. 2 shows samples of polymer extracted from *C. necator* DSM 531.
Figure 3:
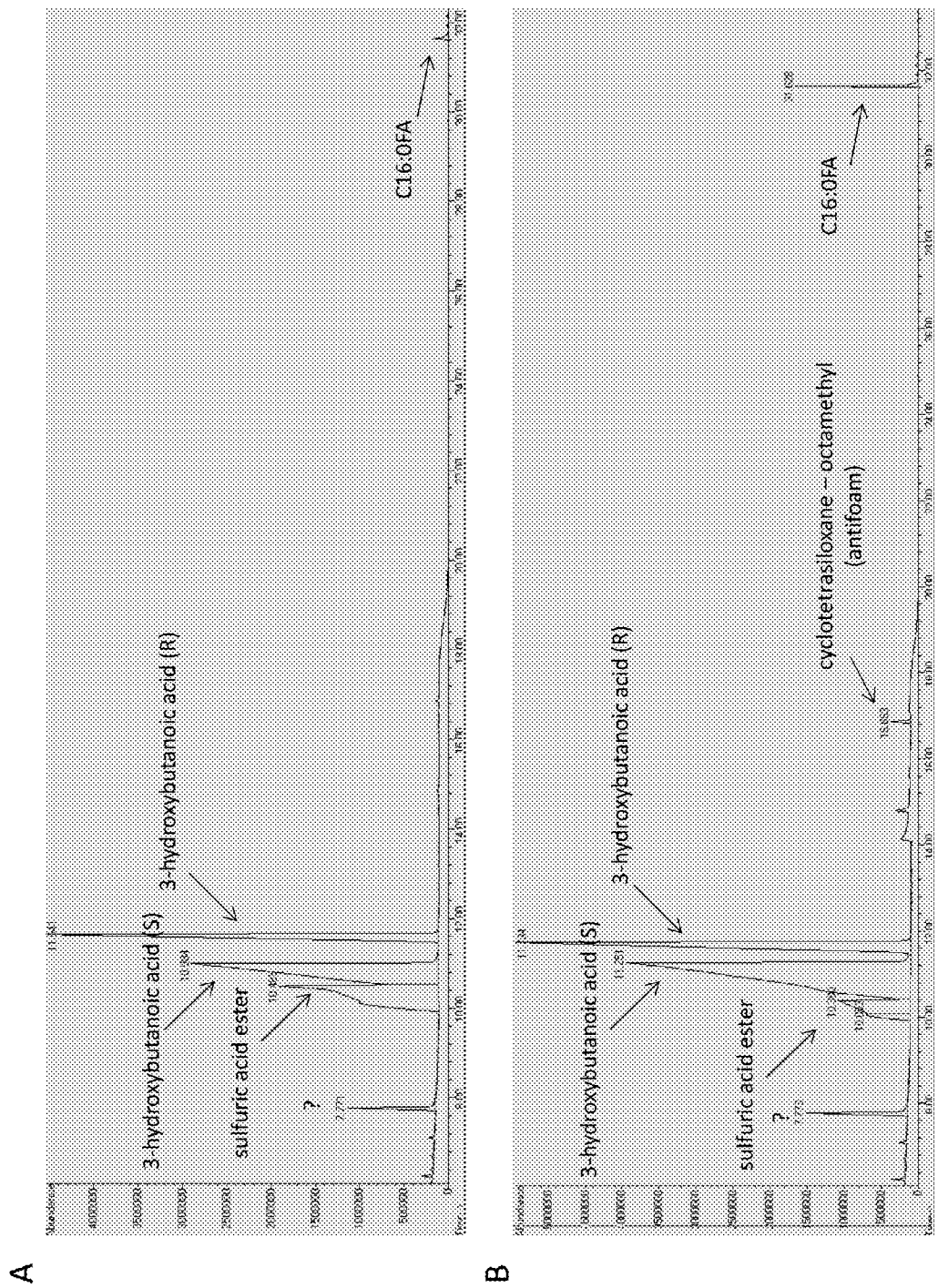
FIG. 3A-3D show gas chromatography-mass spectrometry analysis of monomers derived from extracted polymers from *C. necator* cultures.
Figure 3:
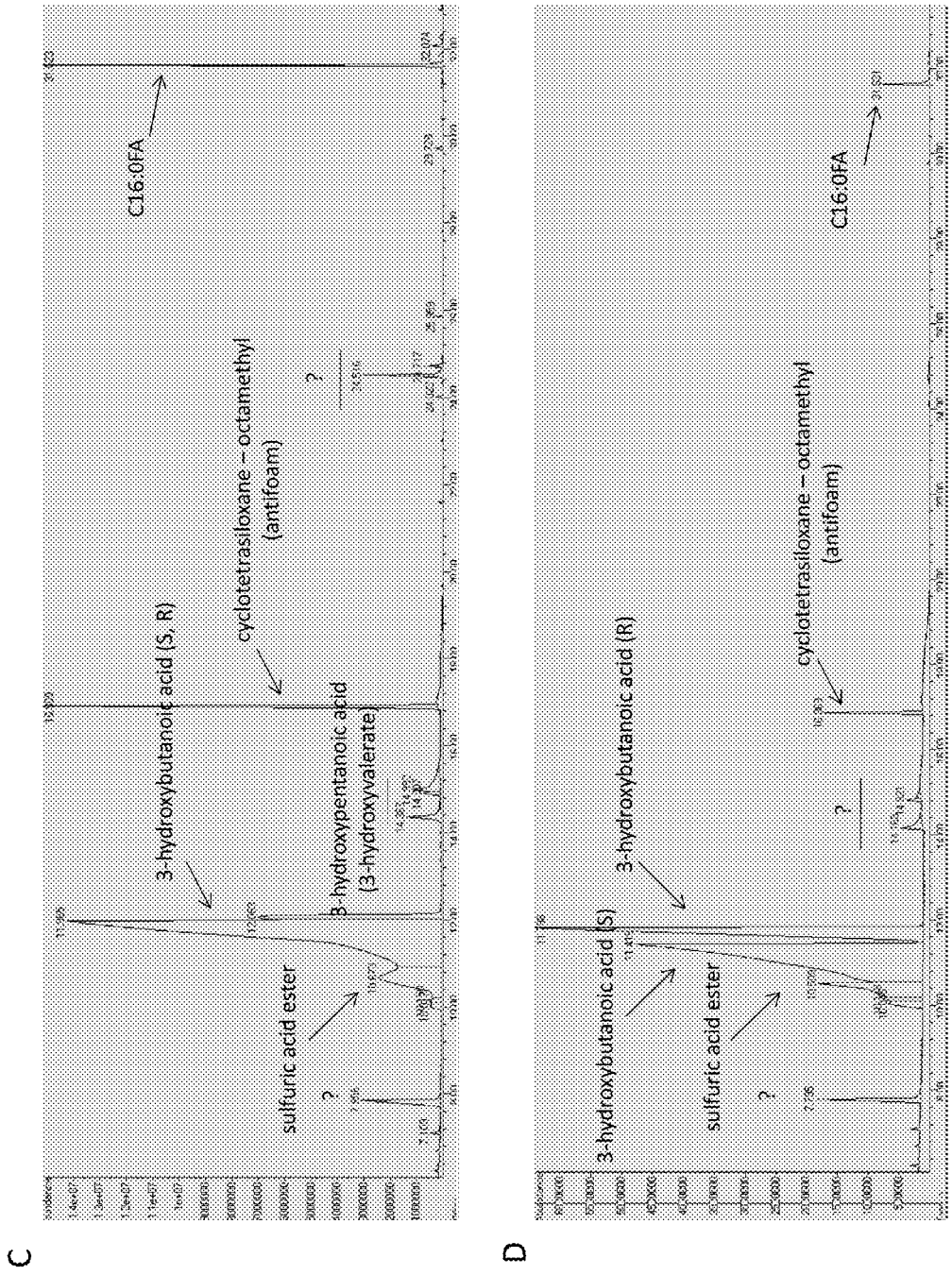

In some embodiments, the instant invention provides for a method of producing polyhydroxybutyrate (PHB) by combining, in a bioreactor or solution, a carbon-containing gas and a natural strain microorganism that converts a carbon-containing gas such as syngas, producer gas, CO2, carbon monoxide and mixtures of the same containing hydrogen gas; and/or C1 compounds, gaseous or liquid, including but not limited to methanol or methane, into polyhydroxybutyrate. (FIGS. 2, 3A and 3B). In some non-limiting embodiments the microorganism is *Cupriavidus necator* DSM 531.

In some embodiments, the instant invention provides for a method of producing polyhydroxybutyrate by combining, in a bioreactor or solution, one or more enzymes used to convert a carbon containing gas into polyhydroxybutyrate including but not limited to HMG-CoA lyase, 3-hydroxybutyrate dehydrogenase, and/or 3-hydroxybuterate polymerase, a carbon-containing gas, and a natural microorganism that converts a carbon-containing gas such as syngas, producer gas, $CO_2$, carbon monoxide and mixtures of the same containing hydrogen gas; and/or C1 compounds, gaseous or liquid, including but not limited to methanol or methane, into a precursor compound that can be enzymatically converted to polyhydroxybutyrate including but not limited to acetyl-CoA, pyruvate, acetoacetate, and 3-hydroxybuterate. (FIG. 1). In some non-limiting embodiments the microorganism is *Cupriavidus necator* DSM 531.

In some embodiments, the instant invention further provides for a method of producing 3-hydroxybuterate by combining, in a bioreactor or solution, a carbon-containing gas and a natural or engineered strain microorganism that converts a carbon-containing gas such as syngas, producer gas, CO2, carbon monoxide and mixtures of the same containing hydrogen gas; and/or C1 compounds, gaseous or liquid, including but not limited to methanol or methane, into 3-hydroxybuterate. (FIG. 1). In some non-limiting embodiments the microorganism is *Cupriavidus necator* DSM 531.

In some embodiments, the instant invention further provides for a method of producing 3-hydoxybuterate by combining, in a bioreactor or solution, one or more enzymes including but not limited to PHB depolymerase, a carbon-containing gas, and a natural or engineered microorganism that converts a carbon-containing gas such as syngas, producer gas, CO2, carbon monoxide and mixtures of the same containing hydrogen gas; and/or C1 compounds, gaseous or liquid, including but not limited to methanol or methane, into a polyhydroxybutyrate. (FIGS. 2, 3A, 3B). In some non-limiting embodiments the microorganism is *Cupriavidus necator* DSM 531. In some non-limiting embodiments the microorganism is *Ralstonia eutropha* N-1, DSM 13513.

In some embodiments, the instant invention further provides for a method of producing 1,3-butanediol by combining, in a bioreactor or solution, a carbon-containing gas and a natural or engineered microorganism that converts a carbon-containing gas such as syngas, producer gas, $CO_2$, carbon monoxide and mixtures of the same containing hydrogen gas; and/or C1 compounds, gaseous or liquid, including but not limited to methanol or methane, into 1,3-butanediol. (FIG. 1). In some embodiments the 1,3-butanediol produced in certain embodiments of the present invention is recovered from the aqueous broth using methods known to one well versed in the art and science. In some embodiments 1,3-butanediol is recovered from the aqueous broth by solvent extraction. In some embodiments 1,3- butanediol is recovered from the aqueous broth using in situ solvent extraction. In some embodiments a biocompatible but not bioavailable solvent is used for in situ solvent extraction of 1,3-BDO. In some non-limiting embodiments the biocompatible but not bioavailable solvent used to extract 1,3-BDO from the aqueous broth is cis-9-octadecen-1-ol. In some embodiments one or more of the following separation steps are used to recover 1,3-BDO from the aqueous broth: steam stripping, pervaporation, reverse osmosis, and/or solvent extraction. In some embodiments one or more of the following solvents are used in liquid-liquid extraction of the 1,3-BDO from the aqueous broth: solvent extractants, e.g., ethyl acetate, tributylphosphate, diethyl ether, n-butanol, dodecanol, and/or oleyl alcohol. In some embodiments prior to exposure to solvent, the aqueous broth is dewatered by evaporation or both microfiltration and reverse osmosis. In some embodiments reactive extraction is used to recover 1,3-butanediol from the aqueous broth whereby 1,3-butanediol is reacted with formaldehyde to form a formal under catalysis of acid (Senkus 1946), with the 1,3-butanediol formal collected in the top oil phase and allowed to react with acid methanol to form 1,3-butanediol and methylal, and the methylal can be hydrolyzed to methanol and formaldehyde, with each of the three reaction steps using acids as catalyst. In some embodiments pervaporation or vacuum membrane distillation is used for the concentration of 1,3-butanediol from the aqueous broth (Qureshi et al. 1994). In some embodiments an integrated process for fed-batch fermentation of 1,3-butanediol combined with recovery of 1,3-butanediol by vacuum membrane distillation is used. In some non-limiting embodiments a microporous polytetrafluoroethylene (PTFE) membrane is used for the recovery by pervaporation or vacuum membrane distillation. In some non-limiting embodiments a silicone membrane is used for the pervaporative recovery of 1,3-butanediol from the aqueous broth. In some embodiments the recovered 1,3-butanediol is converted to butadiene by dehydration using methods known to one well versed in the art and science. In some embodiments a commercially used process for the conversion of 1,3-butanediol to butadiene by dehydration will be utilized. In some non-limiting embodiments the 1,3-butanediol is dehydrated in the gas phase at 270° C. using a Na polyphosphate catalyst to produce 1,3-butadiene. In some non-limiting embodiments the selectivity of the conversion from 1,3-butanediol to butadiene is about 70%. In some non-limiting embodiments the microorganism is *Cupriavidus necator* DSM 531. In some non-limiting embodiments the microorganism is *Ralstonia eutropha* N-1, DSM 13513.

In some embodiments, the instant invention further provides for a method of producing 1,3-butanediol by combining, in a bioreactor or solution, one or more enzymes including but not limited to PHB depolymerase, aldehyde dehydrogenase, and/or alcohol dehydrogenase, a carbon-containing gas, and a natural or engineered microorganism that converts a carbon-containing gas such as syngas, producer gas, $CO_2$, carbon monoxide and mixtures of the same containing hydrogen gas; and/or C1 compounds, gaseous or liquid, including but not limited to methanol or methane, into a polyhydroxybutyrate. (FIGS. 1, 2, 3A, 3B). In some non-limiting embodiments the microorganism is *Cupriavidus necator* DSM 531. In some non-limiting embodiments the microorganism is *Ralstonia eutropha* N-1, DSM 13513.

In some embodiments, the instant invention provides for a natural or engineered microorganism that converts a carbon-containing gas such as syngas, producer gas, $CO_2$, carbon monoxide and mixtures of the same containing hydrogen gas; and/or C1 compounds, gaseous or liquid, including but not limited to methanol or methane, into butanediol (BDO) and encodes one or more genes including but not limited to the enzyme acetolactate synthase, α-acetolactate decarboxylase, and/or 2,3-butanediol dehydrogenase. In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for a method of producing butanediol by combining, in a bioreactor or solution, a carbon-containing gas and a natural or engineered microorganism that converts a carbon-containing gas such as syngas, producer gas, $CO_2$, carbon monoxide and mixtures of the same containing hydrogen gas; and/or C1 compounds, gaseous or liquid, including but not limited to methanol or methane, into butanediol and encodes one or more genes including but not limited to the enzyme acetolactate synthase, α-acetolactate decarboxylase, and/or 2,3-butanediol dehydrogenase. In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for a method of producing butanediol by combining, in a bioreactor or solution, one or more enzymes including but not limited to acetolactate synthase, α-acetolactate decarboxylase, and/or 2,3-butanediol dehydrogenase, a carbon-containing gas, and an engineered or natural microorganism that converts a carbon-containing gas such as syngas, producer gas, $CO_2$, carbon monoxide and mixtures of the same containing hydrogen gas; and/or C1 compounds, gaseous or liquid, including but not limited to methanol or methane, into a pyruvate. In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for a natural or engineered microorganism that converts a carbon-containing gas such as syngas, producer gas, CO2, carbon monoxide and mixtures of the same containing hydrogen gas; and/or C1 compounds, gaseous or liquid, including but not limited to methanol or methane, into butadiene and encodes one or more genes including but not limited to a fatty acid hydrotase including but not limited to oleate hydratase. In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for a method of producing butadiene by combining, in a bioreactor or solution, a carbon-containing gas and an engineered microorganism that converts a carbon-containing gas such as syngas, producer gas, CO2, carbon monoxide and mixtures of the same containing hydrogen gas; and/or C1 compounds, gaseous or liquid, including but not limited to methanol or methane, into butadiene and encodes one or more genes including but not limited to the enzyme a fatty acid hydratase including but not limited to oleate hydratase. In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for a method of producing butadiene by combining, in a bioreactor or solution, one or more enzymes including but not limited to a fatty acid hydratase including but not limited to oleate hydratase, a carbon-containing gas, and an engineered or natural microorganism that converts a carbon-containing gas such as syngas, producer gas, CO2, carbon monoxide and mixtures of the same containing hydrogen gas; and/or C1 compounds, gaseous or liquid, including but not limited to methanol or methane, into a 1,3-butanediol. (FIG. 1). In some embodiments 1,3-butanediol is recovered from the aqueous broth using methods known to one well versed in the art and science. In some embodiments 1,3-butanediol is recovered from the aqueous broth by solvent extraction. In some embodiments 1,3-butanediol is recovered from the aqueous broth using in situ solvent extraction. In some embodiments a biocompatible but not bioavailable solvent is used for in situ solvent extraction of 1,3-BDO. In some non-limiting embodiments the biocompatible but not bioavailable solvent used to extract 1,3-BDO from the aqueous broth is cis-9-octadecen-1-ol. In some embodiments one or more of the following separation steps are used to recover 1,3-BDO from the aqueous broth: steam stripping, pervaporation, reverse osmosis, and/or solvent extraction. In some embodiments one or more of the following solvents are used in liquid-liquid extraction of the 1,3-BDO from the aqueous broth: solvent extractants, e.g., ethyl acetate, tributylphosphate, diethyl ether, n-butanol, dodecanol, and/or oleyl alcohol. In some embodiments prior to exposure to solvent, the aqueous broth is dewatered by evaporation or both microfiltration and reverse osmosis. In some embodiments reactive extraction is used to recover 1,3-butanediol from the aqueous broth whereby 1,3-butanediol is reacted with formaldehyde to form a formal under catalysis of acid (Senkus 1946), with the 1,3-butanediol formal collected in the top oil phase and allowed to react with acid methanol to form 1,3-butanediol and methylal, and the methylal can be hydrolyzed to methanol and formaldehyde, with each of the three reaction steps using acids as catalyst. In some embodiments pervaporation or vacuum membrane distillation is used for the concentration of 1,3-butanediol from the aqueous broth (Qureshi et al. 1994). In some embodiments an integrated process for fed-batch fermentation of 1,3-butanediol combined with recovery of 1,3-butanediol by vacuum membrane distillation is used. In some non-limiting embodiments a microporous polytetrafluoroethylene (PTFE) membrane is used for the recovery by pervaporation or vacuum membrane distillation. In some non-limiting embodiments a silicone membrane is used for the pervaporative recovery of 1,3-butanediol from the aqueous broth. In some embodiments the recovered 1,3-butanediol is converted to butadiene by dehydration using methods known to one well versed in the art and science. In some embodiments a commercially used process for the conversion of 1,3-butanediol to butadiene by dehydration will be utilized. In some non-limiting embodiments the 1,3-butanediol is dehydrated in the gas phase at 270° C. using a Na polyphosphate catalyst to produce 1,3-butadiene. In some non-limiting embodiments the selectivity of the conversion from 1,3-butanediol to butadiene is about 70%. In some non-limiting embodiments the microorganism is *Cupriavidus necator* DSM 531. In some non-limiting embodiments the microorganism is *Ralstonia eutropha* N-1, DSM 13513.

In some embodiments, the instant invention provides for a method of producing butadiene by combining, in a bioreactor or solution, a carbon-containing gas and an engineered microorganism that converts a carbon-containing gas such as syngas, producer gas, $CO_2$, carbon monoxide and mixtures of the same containing hydrogen gas; and/or C1 compounds, gaseous or liquid, including but not limited to methanol or methane, into 1,3-butanediol and encodes one or more genes including but not limited to the enzyme a fatty acid hydratase including but not limited to oleate hydratase. In some non-limiting embodiments the microorganism is *Cupriavidus necator* DSM 531. In some non-limiting embodiments the microorganism is *Ralstonia eutropha* N-1, DSM 13513.

In some embodiments, the instant invention provides for a method of producing butadiene by combining, in a bioreactor or solution, one or more enzymes including but not limited to a fatty acid hydratase including but not limited to oleate hydratase, a carbon-containing gas, and an engineered or natural microorganism that converts a carbon-containing gas such as syngas, producer gas, CO2, carbon monoxide and mixtures of the same containing hydrogen gas; and/or C1 compounds, gaseous or liquid, including, but not limited to methanol or methane, into a 2,3-butanediol. In some embodiments the 2,3-butandiol is converted to butadiene by dehydration. In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for a method of producing butadiene by combining, in a bioreactor or solution, a carbon-containing gas and an engineered microorganism that converts a carbon-containing gas such as syngas, producer gas, CO2, carbon monoxide and mixtures of the same containing hydrogen gas; and/or C1 compounds, gaseous or liquid, including but not limited to methanol or methane, into 2,3-butanediol and encodes one or more genes including but not limited to the enzyme a fatty acid hydratase including but not limited to oleate hydratase. In some non-limiting embodiments the microorganism is *Cupriavidus necator* DSM 531 or DSM 541. In some non-limiting embodiments the microorganism is *Ralstonia eutropha* N-1, DSM 13513.

In some embodiments, the instant invention provides for a method of producing butadiene by first producing butanediol by combining, in a bioreactor or solution, a carbon-containing gas and a natural or engineered microorganism that converts a carbon-containing gas such as syngas, producer gas, $CO_2$, carbon monoxide and mixtures of the same containing hydrogen gas; and/or C1 compounds, gaseous or liquid, including but not limited to methanol or methane into butanediol. In some embodiments the butanediol is recovered from the aqueous broth using methods known to one well versed in the art and science. In some embodiments butanediol is recovered from the aqueous broth by solvent extraction. In some embodiments butanediol is recovered from the aqueous broth using in situ solvent extraction. In some embodiments a biocompatible but not bioavailable solvent is used for in situ solvent extraction of BDO. In some non-limiting embodiments the biocompatible but not bioavailable solvent used to extract BDO from the aqueous broth is cis-9-octadecen-1-ol. In some embodiments one or more of the following separation steps are used to recover BDO from the aqueous broth: steam stripping, pervaporation, reverse osmosis, and/or solvent extraction. In some embodiments one or more of the following solvents are used in liquid-liquid extraction of the BDO from the aqueous broth: solvent extractants, e.g., ethyl acetate, tributylphosphate, diethyl ether, n-butanol, dodecanol, and/or oleyl alcohol. In some embodiments prior to exposure to solvent, the aqueous broth dewatered by evaporation or both microfiltration and reverse osmosis. In some embodiments reactive extraction is used to recover butanediol from the aqueous broth whereby butanediol is reacted with formaldehyde to form a formal under catalysis of acid (Senkus 1946), with the butanediol formal collected in the top oil phase and allowed to react with acid methanol to form butanediol and methylal, and the methylal can be hydrolyzed to methanol and formaldehyde, with each of the three reaction steps using acids as catalyst. In some embodiments pervaporation or vacuum membrane distillation is used for the concentration of butanediol from the aqueous broth (Qureshi et al. 1994). In some embodiments an integrated process for fed-batch fermentation of butanediol combined with recovery of butanediol by vacuum membrane distillation is used. In some non-limiting embodiments a microporous polytetrafluoroethylene (PTFE) membrane is used for the recovery by pervaporation or vacuum membrane distillation. In some non-limiting embodiments a silicone membrane is used for the pervaporative recovery of butanediol from the aqueous broth. In some embodiments the butanediol recovered from the aqueous broth is then by converting into butadiene chemically by dehydrating butanediol over a catalyst such as thorium oxide using methods known to one well versed in the art and science. In some embodiments the isomer of butanediol produced in the bioreactor and recovered from the broth is 1,3-butanediol. In some embodiments a commercially used process for the conversion of 1,3-butanediol to butadiene by dehydration will be utilized. In some non-limiting embodiments the 1,3-butanediol is dehydrated in the gas phase at 270° C. using a Na polyphosphate catalyst to produce 1,3-butadiene. In some non-limiting embodiments the selectivity of the conversion from 1,3-butanediol to butadiene is about 70%. In some embodiments, 1,3-butadiene is further converted into styrene-butadiene rubber by mixing butadiene with styrene using methods known to one well versed in the art and science of synthetic rubber manufacturing. In some embodiments the butadiene is further converted to caprolactam using methods known to one well versed in the art and science by first carbonylating butadiene into methyl 3-pentenoate, then isomerizing methyl 3-pentenoate into methyl 4-pentenoate, then hydroformylating methyl 4-pentenoate into methyl 5-formylvalerate, which is mixed with hydrogen and ammonia into methyl 6-aminocaproate, which is mixed in a multitubular reactor with xylene to produce caprolactam and methanol. In some embodiments, butadiene is further converted into adiponitrile using methods known to one well versed in the art and science by a nickel-catalyzed hydrocynation of butadiene, involving butadiene monohydocynated into isomers of pentenenitriles, and 2- and 3-methylbutenentriles, the unsaturated nitriles are isomerized into 3- and 4-pentenenitriles, which are hydrocynated to produce adiponitrile. In some embodiments, using methods known to one well versed in the art and science adiponitrile is further hydrogenated into 1,6-diaminohexane, which is then mixed with adipic acid for the production of nylon 6,6. In some embodiments using methods known to one well versed in the art and science the butadiene is used to produce synthetic rubber through polymerization. In some non-limiting embodiments the microorganism is Cupriavidus necator DSM 531 or DSM 541. In some non-limiting embodiments the microorganism is Ralstonia eutropha N-1, DSM 13513.

In some embodiments, the instant invention provides for a method of producing omega-7 fatty acids including but not limited to palmitoleic acid also known as 7-hexadecenoic acid, by combining, in a bioreactor or solution, a carbon-containing gas, and a natural strain microorganism that converts a carbon-containing gas such as syngas, producer gas, CO2, carbon monoxide and mixtures of the same containing hydrogen gas; and/or C1 compounds, gaseous or liquid, including but not limited to methanol or methane, into omega-7 fatty acids, including but not limited to palmitoleic acid (FIG. 4). In some non-limiting embodiments the microorganism is *Rhodococcus opacus* DSM 43205. In some non-limiting embodiments the microorganism is *Rhodococcus* sp. DSM 3346.

In some embodiments, the instant invention provides for a method of producing polyunsaturated fatty acids including but not limited to alpha-linoleic acid, by combining, in a bioreactor or solution, a carbon-containing gas, and a natural strain microorganism that converts a carbon-containing gas such as syngas, producer gas, CO2, carbon monoxide and mixtures of the same containing hydrogen gas; and/or C1 compounds, gaseous or liquid, including but not limited to methanol or methane, into a polyunsaturated fatty acids, including but not limited to alpha-linoleic acid (FIG. 4). In some non-limiting embodiments the microorganism is *Rhodococcus opacus* DSM 43205. In some non-limiting embodiments the microorganism is *Rhodococcus* sp. DSM 3346.

In some embodiments, the instant invention provides for a method of producing carotenoids including but not limited to beta-carotene, by combining, in a bioreactor or solution, a carbon-containing gas, and a natural strain microorganism that converts a carbon-containing gas such as syngas, producer gas, $CO_2$, carbon monoxide and mixtures of the same containing hydrogen gas; and/or C1 compounds, gaseous or liquid, including but not limited to methanol or methane, into a carotenoid, including but not limited to beta-carotene.

In some embodiments, the instant invention provides for a method of producing long chain alkanes including but not restricted to eicosane, by combining, in a bioreactor or solution, a carbon-containing gas, and a natural strain microorganism that converts a carbon-containing gas such as syngas, producer gas, $CO_2$, carbon monoxide and mixtures of the same containing hydrogen gas; and/or C1 compounds, gaseous or liquid, including but not limited to methanol or methane, into long chain alkanes including but not restricted to eicosane (FIG. 4). In some non-limiting embodiments the microorganism is *Rhodococcus opacus* DSM 43205. In some non-limiting embodiments the microorganism is *Rhodococcus* sp. DSM 3346.

In some embodiments, the instant invention provides for an engineered or natural microorganism that converts carbon monoxide and water ($H_2O$) into hydrogen gas ($H_2$) and carbon dioxide and encodes one or more enzyme genes including but not limited to hydrogenase, and/or carbon monoxide dehydrogenase.

In some embodiments, the instant invention provides for a method of producing hydrogen gas and carbon dioxide by combining, in a bioreactor or solution, carbon monoxide, water ($H_2O$) and an engineered or natural microorganism that converts carbon monoxide and water ($H_2O$) into hydrogen gas ($H_2$) and carbon dioxide and encodes one or more genes including but not limited to the enzyme hydrogenase, and/or carbon monoxide dehydrogenase.

In some embodiments, the instant invention provides for a method of producing hydrogen gas ($H_2$) and carbon dioxide by combining, in a bioreactor or solution, one or more enzymes including but not limited to hydrogenase and/or carbon monoxide dehydrogenase, carbon monoxide, and water ($H_2O$).

In some embodiments, the instant invention provides for a method of producing hydrogen gas and carbon dioxide by combining, in a bioreactor or solution, carbon monoxide, water ($H_2O$) and a natural strain or engineered microorganism that converts carbon monoxide and water ($H_2O$) into hydrogen gas ($H_2$) and carbon dioxide.

In some embodiments the natural or engineered strain includes but is not limited to carbon monoxide utilizing microbes including but not limited to *Rhodospirillum rubrum* or *Rhodopseudomonas sp*. In some embodiments the natural or engineered strain includes but is not limited to hydrogen utilizing microbes including but not limited to the genera *Rhodococcus* or *Gordonia, Ralstonia* or *Cupriavidus*. In some embodiments the natural or engineered strain includes but is not limited to *Corynebacterium autotrophicum*. In some embodiments the natural or engineered strain includes but is not limited to *Corynebacterium glutamicum*. In some embodiments the natural or engineered strain includes but is not limited to the chemoautotrophic microorganisms from the group consisting of one or more of the following genera: *Acetoanaerobium* sp.; *Acetobacterium* sp.; *Acetogenium* sp.; *Achromobacter* sp.; *Acidianus* sp.; *Acinetobacter* sp.; *Actinomadura* sp.; *Aeromonas* sp.; *Alcaligenes* sp.; *Alcaligenes* sp.; *Arcobacter* sp.; *Aureobacterium* sp.; *Bacillus* sp.; *Beggiatoa* sp.; *Butyribacterium* sp.; *Carboxydothermus* sp.; *Clostridium* sp.; *Comamonas* sp.; *Dehalobacter* sp.; *Dehalococcoide* sp.; *Dehalospirillum* sp.; *Desulfobacterium* sp.; *Desulfomonile* sp.; *Desulfotomaculum* sp.; *Desulfovibrio* sp.; *Desulfurosarcina* sp.; *Ectothiorhodospira* sp.; *Enterobacter* sp.; *Eubacterium* sp.; *Ferroplasma* sp.; *Halothibacillus* sp.; *Hydrogenobacter* sp.; *Hydrogenomonas* sp.; *Leptospirillum* sp.; *Metallosphaera* sp.; *Methanobacterium* sp.; *Methanobrevibacter* sp.; *Methanococcus* sp.; *Methanosarcina* sp.; *Micrococcus* sp.; *Nitrobacter* sp.; *Nitrosococcus* sp.; *Nitrosolobus* sp.; *Nitrosomonas* sp.; *Nitrosospira* sp.; *Nitrosovibrio* sp.; *Nitrospina* sp.; *Oleomonas* sp.; *Paracoccus* sp.; *Peptostreptococcus* sp.; *Planctomycetes* sp.; *Pseudomonas* sp.; *Ralstonia* sp.; *Rhodobacter* sp.; *Rhodococcus* sp.; *Rhodocyclus* sp.; *Rhodomicrobium* sp.; *Rhodopseudomonas* sp.; *Rhodospirillum* sp.; *Shewanella* sp.; *Streptomyces* sp.; *Sulfobacillus* sp.; *Sulfolobus* sp.; *Thiobacillus* sp.; *Thiomicrospira* sp.; *Thioploca* sp.; *Thiosphaera* sp.; *Thiothrix* sp. In some embodiments the natural or engineered strain includes but is not limited to the following genera: *Rhizobium* sp.; *Thiocapsa* sp.; *Nocardia* sp.; *Hydrogenovibrio* sp.; *Helicobacter* sp.; *Xanthobacter* sp.; *Bradyrhizobium* sp.; *Gordonia* sp.; *Mycobacteria* sp.; *Variovorax* sp.; *Acidovorax* sp.; *Anabaena* sp.; *Scenedesmus* sp.; *Chlamydomonas* sp., *Ankistrodesmus* sp., and *Rhaphidium* sp.

In some embodiments, a natural strain or engineered microorganism converts a carbon-containing gas such as syngas, producer gas, $CO_2$, carbon monoxide and mixtures of the same containing hydrogen gas; and/or C1 compounds, gaseous or liquid, including but not limited to methanol or methane, into organic compounds including but not limited to one or more of the following: Methyl undecanoate (11:0), Cyclopentasiloxane, decamethyl-, Cyclotetrasiloxane, octamethyl-, 7H-Dibenzo[b,g]carbazole, 7-methyl-, Cyclohexasiloxane, dodecamethyl-, Cyclopentasiloxane, decamethyl-, Cyclopentasiloxane, decamethyl-, Benzeneacetic acid, .alpha.,3,4-tris[(t, Malonic acid, 2-(2,3-dihydro-benzo[b]th, .beta.-D-Fructofuranose, 2,3,4,6-tetrak, Benzoic acid, 2,5-bis(trimethylsiloxy)-, 2-Acetyl-1,3,3,4,4-pentamethylcyclopent, Cycloheptasiloxane, tetradecamethyl-, Cyclohexasiloxane, dodecamethyl-, 7-Chloro-2,3-dihydro-3-(4-N,N-dimethyla, Cyclohexasiloxane, dodecamethyl-, Benzothiophene, 5-chloro-3-methyl-2-(2-, 7-Chloro-2,3-dihydro-3-(4-N,N-dimethyla, Ethyl alpha-hydroxy-O-nitrocinnamate, 2-Methyl-4-ethoxycarbonyl-3H-imidazo[1, Heptasiloxane, 1,1,3,3,5,5,7,7,9,9,11,1,2-Acetyl-1,3,3,4,4-pentamethylcyclopent, Silane, [[4-[1,2-bis[(trimethylsilyl)ox, TETRADECANOIC ACID, METHYL ESTER (14:0), Thiocyanic acid carbazol-3,6-diyl ester, Cycloheptasiloxane, tetradecamethyl-, Thiophene, 2-(trimethylsilyl)-5-[(trime, 2-Acetyl-1,3,3,4,4-pentamethylcyclopent, ISOPENTADECANOIC ACID, METHYL ESTER (IS, ANTEISO PENTADECANOIC ACID (A15:0), 3-Isopropoxy-1,1,1,7,7,7-hexamethyl-3,5, Cyclononasiloxane, octadecamethyl-, ISO HEXADECANOIC ACID, METHYL ESTER, 7-HEXADECENOIC ACID, METHYL ESTER (16:1, 7-HEXADECENOIC ACID, METHYL ESTER (16:1, HEXADECANOIC ACID, METHYL ESTER (16:0), HEXADECANOIC ACID, METHYL ESTER (16:0), HEXADECANOIC ACID, METHYL ESTER (16:0), Cyclohexane, (1,2-dimethylbutyl)-, cis-13-Octadecenoic acid, Cyclopentane, 1-pentyl-2-propyl-, Cyclohexanone, 2-ethyl-2-propyl-, 4-Methyl-dodec-3-en-1-ol, n-Hexadecanoic acid, Cyclopentane, 1-pentyl-2-propyl-, Cyclohexane, 1,2,4-trimethyl-, 7,8-Epoxide-Octadecanoic Acid, Methyl E, CYCLOPROPYLHEPTADECANOIC ACID, METHYL E, CYCLOPROPYLHEPTADECANOIC ACID, METHYL E, 3-HYDROXY DODECANOIC ACID, METHYL ESTER, Cyclononasiloxane, octadecamethyl-, 2-HYDROXY HEXADECANOIC ACID, METHYL EST, Cycloheptane, 3-HYDROXY DODECANOIC ACID, METHYL ESTER, 2,4-Difluoroaniline, 9-OCTADECENOIC ACID, METHYL ESTER (18:1, Succinic acid, 2-hexyl pentyl ester, 7-OCTADECENOIC ACID, METHYL ESTER (18:1, OCTADECANOIC ACID, METHYL ESTER (18:0), 2,2-Dimethylpropanoic acid, undecyl est, Nonanoic acid, trimethylsilyl ester, Carbamic acid, 1-naphthyl-, propyl este, 2-(5-Nitro-2-furyl)benzimidazole monohy, 10-METHYL OCTADECANOIC ACID (10ME18:0), Decanoic acid, methyl ester, Cyclopentaneundecanoic acid, methyl est, 12-NONADECENOIC ACID, METHYL ESTER (19: Cyclopropyl Nonadecanoic Acid (Cyc 19:0, 13-Tetradecynoic acid, methyl ester, Propenoic acid, 3-(5-ethoxycarbonyl-2,4, Octadecanoic acid, 11-methoxy-, methyl, Succinic acid, di(2-(2-methoxyethyl) hep, 6-Aza-2-thiothymine, Octadecanoic acid, 11-methoxy-, methyl, 3-Methoxymethoxy-2,3-dimethylundec-1-en, 10-Hydroxydecanoic acid, methyl ester, 1,4-Benzenedicarboxylic acid, methyl tr, Cyclohexanebutanoic acid, .alpha., 4-dim, Di-n-octyl phthalate, 3,6-Dioxa-2,4,5,7-tetrasilaoctane, 2,2, Picein, Methyl undecanoate (11:0), TETRADECANOIC ACID, METHYL ESTER (14:0), ISOPENTADECANOIC ACID, METHYL ESTER (IS, 7-HEXADECENOIC ACID, METHYL ESTER (16:1, 7-HEXADECENOIC ACID, METHYL ESTER (16:1, HEXADECANOIC ACID, METHYL ESTER (16:0), Oleyl alcohol, trifluoroacetate, 4-Octene, 2,6-dimethyl-, [S-(E)]-, Cyclooctane, 1,2-dimethyl-, Cyclopentane, pentyl-, Cyclohexane, 1,2,4-trimethyl-, CYCLOPROPYLHEPTADECANOIC ACID, METHYL E, cis-10-Heptadecenoic acid, methyl ester, CYCLOPROPYLHEPTADECANOIC ACID, METHYL E, Octadecanoic acid, 9,10,12-trimethoxy-, 7-OCTADECENOIC ACID, METHYL ESTER (18:1, OCTADECANOIC ACID, METHYL ESTER (18:0), Nonanoic acid, trimethylsilyl ester, Dipyrido[3,2-b; 2,3-d]pyrrole, 1,9-dioxi, Adipic acid, di(trans-2-methylcyclohexy, Nonanoic acid, 9-oxo-, methyl ester, Cyclopropyl Nonadecanoic Acid (Cyc 19:0, TETRADECANOIC ACID, METHYL ESTER (14:0), ISOPENTADECANOIC ACID, METHYL ESTER (ISO 15:0), ANTEISO PENTADECANOIC ACID (A15:0), ISO HEXADECANOIC ACID, METHYL ESTER, 7-HEXADECENOIC ACID, METHYL ESTER (16:1W7TRANS), 7-HEXADECENOIC ACID, METHYL ESTER (16:1W7CIS), HEXADECANOIC ACID, METHYL ESTER (16:0), CYCLOPROPYLHEP- TADECANOIC ACID, METHYL ESTER (CYC17:0), n-Hexadecanoic acid, Cyclopentane, undecyl-, 1-Nonene, 11-Methyl Hexadecanoic Acid, Methyl Ester (11-Me 16:0), 7-HEXADECENOIC ACID, METHYL ESTER (16:1W7TRANS), 7-HEXADECENOIC ACID, METHYL ESTER (16:1W7CIS), HEPTADECANOIC ACID, METHYL ESTER (17:0), 3-HYDROXY TETRADECANOIC ACID, METHYL ESTER (3-OH 14:0), 3-HYDROXY TETRADECANOIC ACID, METHYL ESTER (3-OH 14:0), Methane, diethoxy-, Heptanedioic acid, 4-methyl-, dimethyl ester, 1,2,4-Triazine-6-carboxylic acid, 2,3,4,5-tetrahydro-5-oxo-3-thioxo-, ethyl ester, OCTADECANOIC ACID, METHYL ESTER (18:0), Cyclopentanone, 2-methyl-3-(1-methylethyl)-, Carbamic acid, 1-naphthyl-, propyl ester, 1-Methoxycarbonylethyl-5-methoxycarbonylpentyl ether, Decanoic acid, methyl ester, 1,6-Anhydro-3,4-O-isopropylidene-2-tosyl-D-galactose, 12-NONADECENOIC ACID, METHYL ESTER (19:1W12 CIS), Cyclopropyl Nonadecanoic Acid (Cyc 19:0), 9-Hydroxypentadecanoic acid, methyl ester, Methyl 5,9-dimethyldecanoate, Octadecanoic acid, 11-methoxy-, methyl ester, 9-OCTADECENOIC ACID, METHYL ESTER (18:1W9 TRANS), 1,1-Dipropyl-3-[2-thiazolyl]-2-thiourea, Octadecanoic acid, 11-methoxy-, methyl ester, (.+/−.)-, Nordextromethorphan, Dodecanoic acid, 2-methyl-, Cyclohexyl undecanoic acid, methyl ester (Cyclohexyl 17:0), Methyl 5,9-dimethyldecanoate, Cyclotrisiloxane, hexamethyl-, Iso-Tridecanoic Acid, Methyl Ester (Iso 13:0), ISOTETRADECANOIC ACID, METHYL ESTER (ISO 14:0), TETRADECANOIC ACID, METHYL ESTER (14:0), ISOPENTADECANOIC ACID, METHYL ESTER (ISO 15:0), ANTEISO PENTADECANOIC ACID (A15:0), ISOPENTADECANOIC ACID, METHYL ESTER (ISO 15:0), HEXADECANOIC ACID, METHYL ESTER (16:0), 7-HEXADECENOIC ACID, METHYL ESTER (16:1W7TRANS), HEXADECANOIC ACID, METHYL ESTER (16:0), 7-Hexadecenoic acid, methyl ester, (Z)-, n-Hexadecanoic acid, 2-Propenoic acid, 2-methyl-, dodecyl ester, Cyclooctane, methyl-, ISO HEPTADECANOIC ACID, METHYL ESTER (ISO17:0), ANTEISO HEPTADECANOIC ACID, METHYL ESTER, 7-HEXADECENOIC ACID, METHYL ESTER (16:1W7TRANS), 7-HEXADECENOIC ACID, METHYL ESTER (16:1W7CIS), ISO HEPTADECANOIC ACID, METHYL ESTER (ISO17:0), 3-HYDROXY TETRADECANOIC ACID, METHYL ESTER (3-OH 14:0), 2-HYDROXY HEXADECANOIC ACID, METHYL ESTER (2-OH 16:0), 3-HYDROXY TETRADECANOIC ACID, METHYL ESTER (3-OH 14:0), 2-Octanol, 2-methyl-6-methylene-, Octadecanoic acid, methyl ester, 1,2,4-Triazine-6-carboxylic acid, 2,3,4,5-tetrahydro-5-oxo-3-thioxo-, ethyl ester, 7-OCTADECENOIC ACID, METHYL ESTER (18:1W7 CIS), OCTADECANOIC ACID, METHYL ESTER (18:0), Cyclohexane, 1,2,3-trimethyl-, (1.alpha.,2.alpha.,3.beta.)-, Octadecanoic acid, 3-hydroxy-, methyl ester, Cyclopropaneoctanoic acid, 2-octyl-, methyl ester, trans-, Octadecanoic acid, 11-methoxy-, methyl ester, Methyl trans-9-(2-butylcyclopentyl)nonanoate, 1,2-Dodecanediol, NONADECENOIC ACID, METHYL ESTER (19:1W12 TRANS), 12-NONADECENOIC ACID, METHYL ESTER (19:1W12 CIS), Cyclopropyl Nonadecanoic Acid (Cyc 19:0), Decanoic acid, methyl ester, Undecanoic acid, 11-bromo-, methyl ester, Cyclobutane, 1-butyl-2-ethyl-, Ethyl tetradecyl ether, Octadecanoic acid, 11-methoxy-, methyl ester, Methyl 8-methyl-nonanoate, 1,1-Dipropyl-3-[2-thiazolyl]-2-thiourea, 3,8-Dinitrocarbazole, Dodecanoic acid, 2-methyl-, Cyclopropaneoctanoic acid, 2-octyl-, methyl ester, Piperidine, 1-(1-oxo-3-phenyl-2-propynyl)-, Tridecanoic acid, methyl ester, Cyclopenteno[4.3-b]tetrahydrofuran, 3-[(4-methyl-5-oxo-3-phenylthio)tetrahydrofuran-2-yloxymethylene]-, TETRADECANOIC ACID, METHYL ESTER (14:0), ISOPENTADECANOIC ACID, METHYL ESTER (IS, ANTEISO PENTADECANOIC ACID (A15:0), ISO HEXADECANOIC ACID, METHYL ESTER, 7-HEXADECENOIC ACID, METHYL ESTER (16:1, 7-HEXADECENOIC ACID, METHYL ESTER (16:1, 7-HEXADECENOIC ACID, METHYL ESTER (16:1, HEXADECANOIC ACID, METHYL ESTER (16:0), 2(1H)-Naphthalenone, octahydro-1,4a-dim, 3,4,4-Trimethyl-cyclohex-2-en-1-ol, Cyclopentane, 1-pentyl-2-propyl-, Cyclohexane, 1,2,3-trimethyl-, (1.alpha, Triallylsilane, Cyclopentane, pentyl-, Cyclohexane, 1,2,3-trimethyl-, (1.alpha, 7-HEXADECENOIC ACID, METHYL ESTER (16:1, CYCLOPROPYLHEPTADECANOIC ACID, METHYL E, Octadecanoic acid, 9,10,12-trimethoxy-, 7-OCTADECENOIC ACID, METHYL ESTER (18:1, 4-Hydroxy-3-methylpent-2-enoic acid, me, 9-OCTADECENOIC ACID, METHYL ESTER (18:1, OCTADECANOIC ACID, METHYL ESTER (18:0), 2-Octene, 4-ethyl-, 1,2-Benzenediol, o-isonicotinoyl-o'-val, Carbamic acid, 1-naphthyl-, propyl este, Methyl (13S)-(E)-13-trimethylsilyloxy-9, Octadecanoic acid, 11-methoxy-, methyl, Decanoic acid, methyl ester, 5-Decanol, Methyl tetradecanoate, 12-NONADECENOIC ACID, METHYL ESTER (19: Cyclopropyl Nonadecanoic Acid (Cyc 19:0, Methyl 5,9-dimethyldecanoate, 1-Methoxycarbonylethyl-5-methoxycarbony, TETRADECANOIC ACID, METHYL ESTER (14:0), ISOPENTADECANOIC ACID, METHYL ESTER (IS, ANTEISO PENTADECANOIC ACID (A15:0), ISO HEXADECANOIC ACID, METHYL ESTER, 7-HEXADECENOIC ACID, METHYL ESTER (16:1, 7-HEXADECENOIC ACID, METHYL ESTER (16:1, 7-HEXADECENOIC ACID, METHYL ESTER (16:1, HEXADECANOIC ACID, METHYL ESTER (16:0), Oxacyclododecan-2-one, 1,2-Decanediol, Cyclohexane, 1,2,3-trimethyl-, (1.alpha, 2-Hexanone, 5-methyl-3-methylene-, Cyclopentane, pentyl-, Cyclohexanone, 3,5-dimethyl-, cis-, 7-HEXADECENOIC ACID, METHYL ESTER (16:1, CYCLOPROPYLHEPTADECANOIC ACID, METHYL E, Octadecanoic acid, 9,10,12-trimethoxy-, 7-OCTADECENOIC ACID, METHYL ESTER (18:1, Succinic acid, 2,2-dichloroethyl nonyl, OCTADECANOIC ACID, METHYL ESTER (18:0), Cyclopentanone, 2-methyl-3-(1-methyleth, 1,2-Benzenediol, o-isonicotinoyl-o'-val, Carbamic acid, 1-naphthyl-, propyl este, 1H-1-Benzazepine-2,5-dione, 1,4-dimethy, 4-Acetyl-2,3-O-acetone-d-mannosan, Nonanoic acid, 9-oxo-, methyl ester, 1-Azabicyclo[2.2.2]octane-2-carboxylic, Cyclopropyl Nonadecanoic Acid (Cyc 19:0, Nonanoic acid, 9-hydroxy-, methyl ester, 1-Methoxycarbonylethyl-5-methoxycarbony ISOTETRADECANOIC ACID, METHYL ESTER (ISO 14:0), TETRADECANOIC ACID, METHYL ESTER (14:0), ISOPENTADECANOIC ACID, METHYL ESTER (ISO 15:0), ANTEISO PENTADECANOIC ACID (A15:0), PENTADECANOIC ACID, METHYL ACID (15:0), ISO HEXADECANOIC ACID, METHYL ESTER, 7-HEXADECENOIC ACID, METHYL ESTER (16:1W7TRANS), 7-HEXADECENOIC ACID, METHYL ESTER (16:1W7CIS), HEXADECANOIC ACID, METHYL ESTER (16:0), Methyl 8-heptadecenoate, Cyclooctane, methyl-, n-Hexadecanoic acid, Cyclooctane, methyl-, ISO HEPTADECANOIC ACID, METHYL ESTER (ISO17:0), ANTEISO HEPTADECANOIC ACID, METHYL ESTER, 7-HEXADECENOIC ACID, METHYL ESTER (16:1W7TRANS), HEPTADECANOIC ACID, METHYL ESTER (17:0), Methyl 2-hydroxy-hexadecanoate, 3-HYDROXY TETRADECANOIC ACID, METHYL ESTER (3-OH 14:0), Ethyl tetradecyl ether, Heptanedioic acid, 4-methyl-, dimethyl ester, 1,2,4-Triazine-6-carboxylic acid, 2,3,4,5-tetrahydro-5-oxo-3-thioxo-, ethyl ester, Dichloromethyldimethylsilyloxycyclobutane, OCTADECANOIC ACID, METHYL ESTER (18:0), Oxirane, 2-decyl-3-(5-methylhexyl)-, cis-, 2,4,5-Trifluorobenzonitrile, Octadecanoic acid, 11-methoxy-, methyl ester, Nonanoic acid, 9-oxo-, methyl ester, cis-Vaccenic acid, 1-Nitrododecane, 12-NONADECENOIC ACID, METHYL ESTER (19:1W12 CIS), Cyclopropyl Nonadecanoic Acid (Cyc 19:0), Decanoic acid, 2-methyl-, Heptanoic acid, methyl ester, Octadecanoic acid, 11-methoxy-, methyl ester, Phosphonous acid, phenyl-, bis[5-methyl-2-(1-methylethyl)cyclohexyl] ester, [1R-[1.alpha.(1R*,2S*,5R*),2.beta.,5.alpha.]]-, Octadecanoic acid, 11-methoxy-, methyl ester, Dodecanoic acid, methyl ester, 10-Nonadecenoic acid, methyl ester, 1,2-Bis(trimethylsilyl)benzene ISOTETRADECANOIC ACID, METHYL ESTER (ISO 14:0), TETRADECANOIC ACID, METHYL ESTER (14:0), ISOPENTADECANOIC ACID, METHYL ESTER (ISO 15:0), ANTEISO PENTADECANOIC ACID (A15:0), ISOPENTADECANOIC ACID, METHYL ESTER (ISO 15:0), ISO HEXADECANOIC ACID, METHYL ESTER, 7-HEXADECENOIC ACID, METHYL ESTER (16:1W7TRANS), 7-HEXADECENOIC ACID, METHYL ESTER (16:1W7CIS), 7-HEXADECENOIC ACID, METHYL ESTER (16:1W7CIS), HEXADECANOIC ACID, METHYL ESTER (16:0), cis-10-Heptadecenoic acid, methyl ester, n-Hexadecanoic acid, Heptafluorobutyric acid, n-octadecyl ester, Cyclooctane, methyl-, ISO HEPTADECANOIC ACID, METHYL ESTER (ISO17:0), ISO HEPTADECANOIC ACID, METHYL ESTER (ISO17:0), CYCLOPROPYLHEPTADECANOIC ACID, METHYL ESTER (CYC17:0), HEPTADECANOIC ACID, METHYL ESTER (17:0), 2-HYDROXY HEXADECANOIC ACID, METHYL ESTER (2-OH 16:0), 3-HYDROXY DODECANOIC ACID, METHYL ESTER (3-OH 12:0), 2-Octanol, 2-methyl-6-methylene-, Octadecanoic acid, methyl ester, 1,2,4-Triazine-6-carboxylic acid, 2,3,4,5-tetrahydro-5-oxo-3-thioxo-, ethyl ester, OCTADECANOIC ACID, METHYL ESTER (18:0), Cyclohexane, 1,2,3-trimethyl-, (1.alpha.,2.alpha.,3.beta.)-, 1,2-Benzenediamine, 4-(4-aminophenoxy)-, Octadecanoic acid, 11-methoxy-, methyl ester, 9-Hydroxypentadecanoic acid, methyl ester, Decanoic acid, methyl ester, 12-NONADECENOIC ACID, METHYL ESTER (19:1W12 CIS), Cyclopropyl Nonadecanoic Acid (Cyc 19:0), Octadecanoic acid, 9,10-dichloro-, methyl ester, Octadecanoic acid, 11-methoxy-, methyl ester, 1-Methyl-1-(2-pentadecyl)oxy-1-silacyclopentane, Octadecanoic acid, 11-methoxy-, methyl ester, Undecanoic acid, 10-methyl-, methyl ester, METHYL DODECANOATE (12:0), 12-NONADECENOIC ACID, METHYL ESTER (19:1W12 CIS), Cyclotrisiloxane, hexamethyl-, TETRADECANOIC ACID (14:0), ISO/ANTEISO-PENTADECANOIC ACID (C14:0-Me), ISO HEXADECANOIC ACID, HEXADECANOIC ACID (16:0), 7-HEXADECENOIC ACID (16:1), HEXADECANOIC ACID, 11-Methyl, ISO/ANTEISO-HEPTADECANOIC ACID (C16:0-ME), CYCLOPROPYLHEPTADECANOIC ACID (Cyc 17:0)/10-HEPTADECENOIC ACID (17:1), HEPTADECANOIC ACID (C17:0), OCTADECANOIC ACID (18:0), 7-OCTADECENOIC ACID (18:1), 9-OCTADECENOIC ACID (18:1), OCTADECANOIC ACID, 11-METHOXY, OCTADECANOIC ACID, 9,10,12-TRIMETHOXY, CYCLOPROPYL NONADECANOIC ACID (Cyc 19:0)/12-NONADECENOIC ACID (19:1), TETRADECANOIC ACID (C14:0), ISO/ANTEISO-PENTADECANOIC ACID (C14:0-Me), ISO-HEXADECANOIC ACID (C15:0-Me), HEXADECANOIC ACID (16:0), 7-HEXADECENOIC ACID (16:1), ISO/ANTEISO-HEPTADECANOIC ACID (C16:0-Me), CYCLOPROPYL-HEPTADECANOIC ACID (Cyc 17:0), HEPTADECANOIC ACID (C17:0), OCTADECANOIC ACID (18:0), 7-OCTADECENOIC ACID (18:1), 9-OCTADECENOIC ACID (18:1), OCTADECANOIC ACID, 11-METHOXY, OCTADECANOIC ACID, 9,10,12-TRIMETHOXY, CYCLOPROPYL NONADECANOIC ACID (Cyc 19:0)/12-NONADECENOIC ACID (19:1), Methyl undecanoate (11:0), Cyclohexasiloxane, dodecamethyl-, 7-Chloro-2,3-dihydro-3-(4-N,N-dimethyla, Hexasiloxane, tetradecamethyl-, Cycloheptasiloxane, tetradecamethyl-, Cycloheptasiloxane, tetradecamethyl-, Cycloheptasiloxane, tetradecamethyl-, 3,5-Dioxa-4-phospha-2-silaheptan-7-oic, 2,4-Dimethyldodecane, Pentadecane, 3-methyl-, 5-Tetradecene, (E)-, 1-Undecene, 8-methyl-, Cyclotetradecane, Heptasiloxane, hexadecamethyl-, Hexasiloxane, tetradecamethyl-, Hexasiloxane, tetradecamethyl-, 2-Methyl-E-7-hexadecene, Benzoic acid, 2,4-bis[(trimethylsilyl)o, Cyclohexanecarboxylic acid, 6-chlorohex, Succinic acid, hexyl 2-pentyl ester, 5,5-Dibutylnonane, 2-Heptenoic acid, methyl ester, Isopropylmalic acid, O-(tert-butyldimet, 3-Dodecanol, 3,7,11-trimethyl-, Dodecane, 2,6,11-trimethyl-, Eicosane, 2,4-dimethyl-, Hexadecane, 3-methyl-, Piperidine, 1-(5-trifluoromethyl-2-pyri, 9-Octadecene, (E)-, Hexadecanoic acid, 2-hydroxy-, methyl e, 5-Octadecene, (E)-, Trifluoroacetoxy hexadecane, 9-Octadecene, (E)-, 5-Octadecene, (E)-, Ethanol, 2-(octadecyloxy)-, Cyclononasiloxane, octadecamethyl-, Cyclononasiloxane, octadecamethyl-, Cyclononasiloxane, octadecamethyl-, Adipic acid, cyclohexyl isobutyl ester, Succinic acid, butyl tetradecyl ester, 2-Amino-2-oxo-acetic acid, N-[3,4-dimet, Nonadecane, 9-methyl-, cis-10-Heptadecenoic acid, methyl ester, Hexasiloxane, tetradecamethyl-, Cyclononasiloxane, octadecamethyl-, Cyclodecasiloxane, eicosamethyl-, Piperidine, 1-(5-trifluoromethyl-2-pyri, Cyclononasiloxane, octadecamethyl-, Cyclodecasiloxane, eicosamethyl-, Piperidine, 1-(5-trifluoromethyl-2-pyri, n-Nonadecanoic acid, pentamethyldisilyl, Piperidine, 1-(5-trifluoromethyl-2-pyri, Piperidine, 1-(5-trifluoromethyl-2-pyri, n-Nonadecanoic acid, pentamethyldisilyl, Hexasiloxane, tetradecamethyl-, 1,2-Benzenedicarboxylic acid, mono(2-et, Piperidine, 1-(5-trifluoromethyl-2-pyri, Silane, [[4-[1,2-bis[(trimethylsilyl)ox, Hexasiloxane, tetradecamethyl-, Heptasiloxane, hexadecamethyl-, Hexasiloxane, tetradecamethyl-, Cyclononasiloxane, octadecamethyl-, 2,6,10,14,18,22-Tetracosahexaene, 2,6,1, 2-Amino-2-oxo-acetic acid, N-[3,4-dimet, Cyclononasiloxane, octadecamethyl-, Heptasiloxane, hexadecamethyl-, 1,2-Benzisothiazole-3-acetic acid, meth, 2-Amino-2-oxo-acetic acid, N-[3,4-dimet, Hexasiloxane, tetradecamethyl-, Heptasiloxane, hexadecamethyl-, Cyclononasiloxane, octadecamethyl-, Heptasiloxane, hexadecamethyl-, Cyclononasiloxane, octadecamethyl-, DL-Leucine, N-acetyl-, methyl ester, Pentadecanal-, ISOTETRADECANOIC ACID, METHYL ESTER (ISO 14:0), ISO PENTADECENOIC ACID, METHYL ESTER (ISO 15:1), AnteISOPENTADECANOIC ACID, METHYL ESTER (a 15:0), ANTEISO PENTADECANOIC ACID (A15:0), Tetradecanal, ISOPENTADECANOIC ACID, METHYL ESTER (ISO 15:0), HEXADECANOIC ACID, METHYL ESTER (16:0), 7-HEXADECENOIC ACID, METHYL ESTER (16:1W7TRANS), Oxirane, tridecyl-, HEXADECANOIC ACID, METHYL ESTER (16:0), ISO HEPTADECANOIC ACID, METHYL ESTER (ISO17:0), ANTEISO HEPTADECANOIC ACID, METHYL ESTER, Hexadecanal, HEPTADECANOIC ACID, METHYL ESTER (17:0), 6,9-OCTADECADIENOIC ACID, METHYL ESTER (18:2W6,9 ALL CIS), 9-OCTADECENOIC ACID, METHYL ESTER (18:1W9TRANS), 7-OCTADECENOIC ACID, METHYL ESTER (18:1W7 CIS), Oxirane, heptadecyl-, OCTADECANOIC ACID, METHYL ESTER (18:0), Octadecanoic acid, 3-hydroxy-, methyl ester, 10-METHYL OCTADECANOIC ACID (10ME18:0), Bicyclo[10.8.0]eicosane, cis-, EICOSANOIC ACID, METHYL ESTER (20:0), 3-Methoxymethoxy-2,3-dimethylundec-1-ene, Octadecanoic acid, 3-hydroxy-, methyl ester, Octadecanoic acid, 9,10-dichloro-, methyl ester, 9-DOCOSENOIC ACID, METHYL ESTER (22:1 W9CIS), 1-Methoxycarbonylethyl-5-methoxycarbonylpentyl ether, DOCOSANOIC ACID, METHYL ESTER (22:0), trans-13-Octadecenoic acid, methyl ester, 2,6,10,14,18,22-Tetracosahexaene, 2,6,10,15,19,23-hexamethyl-, (all-E)-, Cyclotrisiloxane, hexamethyl-, 7-HEXADECENOIC ACID, METHYL ESTER (16:1W7TRANS), ISO HEXADECANOIC ACID, METHYL ESTER, ANTEISO HEPTADECANOIC ACID, METHYL ESTER, HEPTADECANOIC ACID, METHYL ESTER (17:0), OCTADECATRIENOIC ACID, METHYL ESTER (18: 3W6), Methyl 10-oxohexadecanoate, 6,9-OCTADECADIENOIC ACID, METHYL ESTER (18:2W6,9 ALL CIS), 9-OCTADECENOIC ACID, METHYL ESTER (18:1W9 CIS), 4-Hydroxy-2-methylthio-5-pyrimidinehydroxamic acid, OCTADECANOIC ACID, METHYL ESTER (18:0), 10-METHYL OCTADECANOIC ACID (10ME18:0), Cyclopropyl Nonadecanoic Acid (Cyc 19:0), 3-Methoxymethoxy-2,3-dimethylundec-1-ene, Thiazole, 2-ethyl-4,5-dimethyl-, n-Decylsuccinic anhydride, Cyclopropanecarboxylic acid, heptadecyl ester, Octadecanoic acid, 11-methoxy-, methyl ester, 4-Bromo-2-methoxybut-2-enoic acid, methyl ester, Octadecanoic acid, 9,10-dichloro-, methyl ester, Adipic acid, di(trans-2-methylcyclohexyl) ester, 11-Octadecenoic acid, methyl ester, Cyclotrisiloxane, hexamethyl-, Cyclopentasiloxane, decamethyl-, 4-(Nonafluoro-tert-butyl) nitrobenzene, Cyclohexasiloxane, dodecamethyl-, Methyl undecanoate (11:0), Cycloheptasiloxane, tetradecamethyl-, Silane, [[4-[1,2-bis[(trimethylsilyl)oxy]ethyl]-1,2-phenylene]bis(oxy)]bis[trimethyl-, TETRADECANOIC ACID, METHYL ESTER (14:0), 1,2-Bis(trimethylsilyl)benzene, ISOPENTADECANOIC ACID, METHYL ESTER (ISO 15:0), ANTEISO PENTADECANOIC ACID (A15:0), ISOPENTADECANOIC ACID, METHYL ESTER (ISO 15:0), 3-HYDROXY TETRADECANOIC ACID, METHYL ESTER (3-OH 14:0), Cyclononasiloxane, octadecamethyl-, Pentanamide, N-(4-methoxyphenyl)-, ISO HEXADECANOIC ACID, METHYL ESTER, 7-HEXADECENOIC ACID, METHYL ESTER (16:1W7TRANS), 7-HEXADECENOIC ACID, METHYL ESTER (16:1W7TRANS), Cyclododecanol, HEXADECANOIC ACID, METHYL ESTER (16:0), HEXADECANOIC ACID, METHYL ESTER (16:0), Eicosane, n-Hexadecanoic acid, 10-Methyl Hexadecanoic Acid, Methyl Ester (10-Me 16:0), Cyclobarbital, 2,4-Cyclohexadien-1-one, 3,5-bis(1,1-dimethylethyl)-4-hydroxy-, 9,12-Octadecadienoic acid (Z,Z)-, cis-10-Heptadecenoic acid, methyl ester, Butanoic acid, undec-2-enyl ester, HEPTADECANOIC ACID, METHYL ESTER (17:0), Cyclodecasiloxane, eicosamethyl-, OCTADECATRIENOIC ACID, METHYL ESTER (18:3W6), 9,12-Octadecadienoic acid, methyl ester, (E,E)-, 1-(2-Isopropyl-5-methylcyclopentyl) ethanone, 6,9-OCTADECADIENOIC ACID, METHYL ESTER (18:2W6,9 ALL CIS), 7-OCTADECENOIC ACID, METHYL ESTER (18:1W7 CIS), 7-OCTADECENOIC ACID, METHYL ESTER (18:1W7 CIS), 9-OCTADECENOIC ACID, METHYL ESTER (18:1W9 CIS), Z-11 (13-Methyl)tetradecen-1-ol acetate, OCTADECANOIC ACID, METHYL ESTER (18:0), Octadecanoic acid, 10-METHYL OCTADECANOIC ACID (10ME18:0), Methyl 10-trans,12-cis-octadecadienoate, i-Propyl tricosanoate, 2H-Pyran, 2-(8-dodecynyloxy)tetrahydro-, 12-NONADECENOIC ACID, METHYL ESTER (19:1W12 CIS), 3-Pentane isothiocyanate, Cyclotrisiloxane, hexamethyl-, Methyl 8,11,14-eicosatrienoate, .alpha.-D-Ribopyranose, 5-thio-, cyclic 1,2:3,4-bis(ethylboronate), Cyclononasiloxane, octadecamethyl-, Adipic acid, di(trans-2-methylcyclohexyl) ester, Octadecanoic acid, 9,10-dichloro-, methyl ester, Cyclononasiloxane, octadecamethyl-, Cyclononasiloxane, octadecamethyl-, Octasiloxane, 1,1,3,3,5,5,7,7,9,9,11,11,13,13,15,15-hexadecamethyl-, Trimethyl(4-tert.-butylphenoxy)silane, Trimethyl[4-(1,1,3,3,-tetramethylbutyl)phenoxy]silane, ISOTETRADECANOIC ACID, METHYL ESTER (ISO 14:0), ISOPENTADECANOIC ACID, METHYL ESTER (ISO 15:0), AnteISOPENTADECANOIC ACID, METHYL ESTER (a 15:0), PENTADECANOIC ACID, METHYL ACID (15:0), ISO HEXADECANOIC ACID, METHYL ESTER, 7-HEXADECENOIC ACID, METHYL ESTER (16:1W7CIS), 7-HEXADECENOIC ACID, METHYL ESTER (16:1W7TRANS), HEXADECANOIC ACID, METHYL ESTER (16:0), 10-Methyl Hexadecanoic Acid, Methyl Ester (10-Me 16:0), ISO HEPTADECANOIC ACID, METHYL ESTER (ISO17:0), Methyl 9,10-methylene-hexadecanoate, ISO HEPTADECANOIC ACID, METHYL ESTER (ISO17:0), 9-OCTADECENOIC ACID, METHYL ESTER (18:1W9TRANS), 7-OCTADECENOIC ACID, METHYL ESTER (18:1W7 CIS), OCTADECANOIC ACID, METHYL ESTER (18:0), 10-METHYL OCTADECANOIC ACID (10ME18:0), Cyclopropaneoctanoic acid, 2-octyl-, methyl ester, 2-Bromo-4,6-di-tert-butylphenol, TETRADECENOIC ACID, METHYL ESTER (14:1W5), TETRADECANOIC ACID, METHYL ESTER (14:0), Heneicosane, 1-Iodo-2-methylundecane, PENTADECANOIC ACID, METHYL ACID (15:0), ANTEISO PENTADECANOIC ACID (A15:0), 9-Octadecenoic acid (Z)-, methyl ester, PENTADECANOIC ACID, METHYL ACID (15:0), ISO HEXADECANOIC ACID, METHYL ESTER, 7-HEXADECENOIC ACID, METHYL ESTER (16:1W7TRANS), 7-HEXADECENOIC ACID, METHYL ESTER (16:1W7TRANS), 7-HEXADECENOIC ACID, METHYL ESTER (16:1W7TRANS), HEXADECANOIC ACID, METHYL ESTER (16:0), Heptadecane, 9-octyl-, 10-Methyl Hexadecanoic Acid, Methyl Ester (10-Me 16:0), ISO HEPTADECANOIC ACID, METHYL ESTER (ISO17:0), Eicosane, cis-10-Heptadecenoic acid, methyl ester, Methyl 9,10-methylene-hexadecanoate, HEPTADECANOIC ACID, METHYL ESTER (17:0), Heptacosane, 10-Methyl Heptadecanoic Acid, Methyl Ester (10-Me 17:0), 2-Furanethanol, .beta.-ethoxy-, 6,9-OCTADECADIENOIC ACID, METHYL ESTER (18:2W6,9 ALL CIS), 9-OCTADECENOIC ACID, METHYL ESTER (18:1W9 CIS), 7-OCTADECENOIC ACID, METHYL ESTER (18:1W7 CIS), OCTADECANOIC ACID, METHYL ESTER (18:0), Hexadecanenitrile, 10-METHYL OCTADECANOIC ACID (10ME18:0), Methyl 10-trans,12-cis-octadecadienoate, Octadecanoic acid, 10-oxo-, methyl ester, 12-NONADECENOIC ACID, METHYL ESTER (19:1W12 CIS), NONADECENOIC ACID, METHYL ESTER (19:1W12CIS), Heptadecane, 9-octyl-, Cyclopropyl Nonadecanoic Acid (Cyc 19:0), 12-Methyl Octadecanoic Acid, Methyl Ester (12-Me 18:0), 3-Methoxymethoxy-2,3-dimethylundec-1-ene, Naphthalene, 1,1'-(1,2-ethanediyl)bis-, Heneicosane, 1,2-Benzisothiazole, 3-(hexahydro-1H-azepin-1-yl)-, 1,1-dioxide, 9-EICOSENOIC ACID, METHYL ESTER (20:1W9TRANS), 9-EICOSENOIC ACID, METHYL ESTER (20:1W9TRANS), Cyclopropanecarboxylic acid, heptadecyl ester, EICOSANOIC ACID, METHYL ESTER (20:0), Hexadecane, 2-methyl-, Undecanoic acid, methyl ester, 6-Octadecenoic acid, (Z)-, Heptacosane, Pyrimidine, 2,4-diamino-5-(3-pyridylmethyl)-, Adipic acid, di(trans-2-methylcyclohexyl) ester, Octadecanoic acid, 9,10-dichloro-, methyl ester, 9-DOCOSENOIC ACID, METHYL ESTER (22:1W9TRANS), 4-Acetyl-2,3-O-acetone-d-mannosan, DOCOSANOIC ACID, METHYL ESTER (22:0), 10-Undecynoic acid, methyl ester, Heneicosane, Heptacosane, TETRACOSENOIC ACID, METHYL ESTER (24:1), Eicosane, Cyclotrisiloxane, hexamethyl-, Heneicosane, 3-methyl-, ISOPENTADECANOIC ACID, METHYL ESTER (ISO 15:0), 7-HEXADECENOIC ACID, METHYL ESTER (16:1W7TRANS), ISO HEXADECANOIC ACID, METHYL ESTER, 9,12-Octadecadienoic acid (Z,Z)-, cis-10-Heptadecenoic acid, methyl ester, HEPTADECANOIC ACID, METHYL ESTER (17:0), OCTADECATRIENOIC ACID, METHYL ESTER (18:3W6), 6,9-OCTADECADIENOIC ACID, METHYL ESTER (18:2W6,9 ALL CIS), 3,6,9-OCTADECATRIENOIC ACID, METHYL ESTER (18:3W3), 7-OCTADECENOIC ACID, METHYL ESTER (18:1W7 CIS), 7-OCTADECENOIC ACID, METHYL ESTER (18:1W7 CIS), 11-Dodecenoic acid, 10-hydroxy-, methyl ester, OCTADECANOIC ACID, METHYL ESTER (18:0), 10-METHYL OCTADECANOIC ACID (10ME18:0), Cyclopropyl Nonadecanoic Acid (Cyc 19:0), NONADECANOIC ACID, METHYL ESTER (19:0), 4-Amino-5-methyl-2(1H)-pyrimidinethione, Methyl 8,11,14-eicosatrienoate, 1,2-Benzisothiazole, 3-(hexahydro-1H-azepin-1-yl)-, 1,1-dioxide, Dodecanoic acid, 11-hydroxy-, methyl ester, N-1-Naphthyl-N'-4-[N-aziridyl]butylurea, Succinic acid, 1-cyclopentylethyl ethyl ester, Octadecanoic acid, 9,10-dichloro-, methyl ester, 1-Methoxycarbonylethyl-5-methoxycarbonylpentyl ether, 16-Hexadecanoyl hydrazide, L-Leucine, N-acetyl-, methyl ester, Methyl undecanoate (11:0), Decanedioic acid, dimethyl ester, Pentadecanal-, TETRADECANOIC ACID, METHYL ESTER (14:0), Undecanedioic acid, dimethyl ester, ISOPENTADECANOIC ACID, METHYL ESTER (ISO 15:0), ANTEISO PENTADECANOIC ACID (A15:0), Hexadecanal, PENTADECANOIC ACID, METHYL ACID (15:0), HEXADECANOIC ACID, METHYL ESTER (16:0), 7-HEXADECENOIC ACID, METHYL ESTER (16:1W7TRANS), Methyl hexadec-9-enoate, Oxirane, hexadecyl-, HEXADECANOIC ACID, METHYL ESTER (16:0), HEPTADECANOIC ACID, METHYL ESTER (17:0), ANTEISO HEPTADECANOIC ACID, METHYL ESTER, Oxirane, heptadecyl-, HEPTADECANOIC ACID, METHYL ESTER (17:0), 3,6,9-OCTADECATRIENOIC ACID, METHYL ESTER (18:3W3), 6,9-OCTADECADIENOIC ACID, METHYL ESTER (18:2W6,9 ALL CIS), 7-OCTADECENOIC ACID, METHYL ESTER (18:1W7 CIS), 7-OCTADECENOIC ACID, METHYL ESTER (18:1W7 CIS), Oxirane, hexadecyl-, OCTADECANOIC ACID, METHYL ESTER (18:0), Octadecanoic acid, 3-hydroxy-, methyl ester, 10-METHYL OCTADECANOIC ACID (10ME18:0), 6,9-TETRACOSADIENOIC ACID, METHYL ESTER (24:2W6), Z,E-2,13-Octadecadien-1-ol, Cyclopropyl Nonadecanoic Acid (Cyc 19:0), Bicyclo[10.8.0]eicosane, cis-, NONADECANOIC ACID, METHYL ESTER (19:0), Oxirane, tetradecyl-, Octadecanoic acid, 3-hydroxy-, methyl ester, Methyl 12-oxo-octadecanoate, 9-EICOSENOIC ACID, METHYL ESTER (20:1W9TRANS), 9-EICOSENOIC ACID, METHYL ESTER (20:1W9TRANS), Cyclopropanecarboxylic acid, heptadecyl ester, Oxirane, tetradecyl-, EICOSANOIC ACID, METHYL ESTER (20:0), Heptane, 1,1-diethoxy-, 1-Nonadecene, 1-Nonadecene, Oxirane, tetradecyl-, Docosanoic acid, 4,4-dimethyl-, methyl ester, Octadecanoic acid, 3-hydroxy-, methyl ester, Octadecanoic acid, 9,10-dichloro-, methyl ester, 9-DOCOSENOIC ACID, METHYL ESTER (22:1W9TRANS), 9-DOCOSENOIC ACID, METHYL ESTER (22:1 W9CIS), 3-Methoxymethoxy-2,3-dimethylundec-1-ene, Phthalic acid, 2-ethylhexyl tridecyl ester, DOCOSANOIC ACID, METHYL ESTER (22:0), 10-Undecynoic acid, methyl ester, TRICOSANOIC ACID, METHYL ESTER (23:0), 2,2-Dimethylpropanoic acid, heptadecyl ester, TETRACOSENOIC ACID, METHYL ESTER (24:1), TETRACOSENOIC ACID, METHYL ESTER (24:1), TETRACOSENOIC ACID, METHYL ESTER (24:1), TETRACOSANOIC ACID, METHYL ESTER (24:0), 2,6,10,14,18,22-Tetracosahexaene, 2,6,10,15,19,23-hexamethyl-, (all-E)-, Cyclotrisiloxane, hexamethyl-, Cyclotrisiloxane, hexamethyl-, Cyclotrisiloxane, hexamethyl-, 1,2,8,9-Dibenzpentacene, TETRADECANOIC ACID, METHYL ESTER (14:0), PENTADECANOIC ACID, METHYL ACID (15:0), ANTEISO PENTADECANOIC ACID (A15:0), PENTADECANOIC ACID, METHYL ACID (15:0), HEXADECANOIC ACID, METHYL ESTER (16:0), 7-HEXADECENOIC ACID, METHYL ESTER (16:1W7TRANS), 7-HEXADECENOIC ACID, METHYL ESTER (16:1W7TRANS), HEXADECANOIC ACID, METHYL ESTER (16:0), ISO HEPTADECANOIC ACID, METHYL ESTER (ISO17:0), ISO HEPTADECANOIC ACID, METHYL ESTER (ISO17:0), 9-Hexadecenoic acid, methyl ester, (Z)-, HEPTADECANOIC ACID, METHYL ESTER (17:0), Iso-Octadecanoic Acid, Methyl Ester (Iso 18:0), 9-OCTADECENOIC ACID, METHYL ESTER (18:1W9CIS), 7-OCTADECENOIC ACID, METHYL ESTER (18:1W7 CIS), OCTADECANOIC ACID, METHYL ESTER (18:0), 10-METHYL OCTADECANOIC ACID (10ME18:0), Cyclopropaneoctanoic acid, 2-octyl-, methyl ester, Methyl 13-eicosenoate. In some non-limiting embodiments the microorganism is *Rhodococcus opacus* DSM 43205. In some non-limiting embodiments the microorganism is *Rhodococcus* sp. DSM 3346. In some non-limiting embodiments the microorganism is *Cupriavidus necator* DSM 531 or DSM 541. In some non-limiting embodiments the microorganism is *Ralstonia eutropha* N-1, DSM 13513.

Aspects of the invention relate to engineered organisms for use in the production of molecules for industrial application. As used herein, "engineered organisms" refer to organisms that recombinantly express nucleic acids. In some embodiments, such nucleic acids encode enzymes as discussed herein. Homologs and alleles of genes associated with the invention can be identified by conventional techniques. Also encompassed by the invention are nucleic acids, referred to as "primers" or "primer sets," that hybridize under stringent conditions to the genes described herein. The term "stringent conditions" as used herein refers to parameters with which the art is familiar. Nucleic acid hybridization parameters may be found in references which compile such methods, e.g. Molecular Cloning: A Laboratory Manual, J. Sambrook, et al., eds., Fourth Edition, Cold Spring Harbor Laboratory Press, Cold Spring Harbor, N.Y., 2012, or Current Protocols in Molecular Biology, F. M. Ausubel, et al., eds., John Wiley & Sons, Inc., New York.

It should be appreciated that the genes associated with invention can be obtained from a variety of sources. It should be further appreciated that any of the nucleic acids and/or polypeptides described herein can be codon-optimized and expressed recombinantly in a codon-optimized form.

As one of ordinary skill in the art would be aware, homologous genes for enzymes described herein could be obtained from other species and could be identified by homology searches, for example through a protein BLAST search, available at the National Center for Biotechnology Information (NCBI) internet site (ncbi.nlm.nih.gov). Genes associated with the invention can be PCR amplified from DNA from any source of DNA which contains the given gene. In some embodiments, genes associated with the invention are synthetic. Any means of obtaining a gene encoding the enzymes associated with the invention are compatible with the instant invention.

In general, homologs and alleles typically will share at least 75% nucleotide identity and/or at least 80% amino acid identity to the sequences of nucleic acids and polypeptides, respectively, in some instances will share at least 90% nucleotide identity and/or at least 90% amino acid identity and in still other instances will share at least 95% nucleotide identity and/or at least 95% or 99% amino acid identity. The homology can be calculated using various, publicly available software tools developed by NCBI (Bethesda, Md.) that can be obtained through the NCBI internet site. Exemplary tools include the BLAST software, also available at the NCBI internet site (www.ncbi.nlm.nih.gov). Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code. The invention also embraces codon optimization to suit optimal codon usage of a host cell.

The invention also provides modified nucleic acid molecules which include additions, substitutions and deletions of one or more nucleotides. In preferred embodiments, these modified nucleic acid molecules and/or the polypeptides they encode retain at least one activity or function of the unmodified nucleic acid molecule and/or the polypeptides, such as enzymatic activity. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules which encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2-6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

The invention embraces variants of polypeptides. As used herein, a "variant" of a polypeptide is a polypeptide which contains one or more modifications to the primary amino acid sequence of the polypeptide. Modifications which create a variant can be made to a polypeptide, for example to: 1) reduce or eliminate an activity of a polypeptide; 2) enhance a property of a polypeptide; 3) provide a novel activity or property to a polypeptide, such as addition of an antigenic epitope or addition of a detectable moiety; or 4) provide equivalent or better binding between molecules (e.g., an enzymatic substrate). Modifications to a polypeptide are typically made to the nucleic acid which encodes the polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the amino acid sequence. One of skill in the art will be familiar with methods for predicting the effect on protein conformation of a change in protein sequence, and can thus "design" a variant of a polypeptide according to known methods. One example of such a method is described by Dahiyat and Mayo in Science 278:82 87, 1997, whereby proteins can be designed de novo. The method can be applied to a known protein to vary only a portion of the polypeptide sequence. By applying the computational methods of Dahiyat and Mayo, specific variants of a polypeptide can be proposed and tested to determine whether the variant retains a desired conformation.

In general, variants include polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of a polypeptide by eliminating proteolysis by proteases in an expression system (e.g., dibasic amino acid residues in yeast expression systems in which KEX2 protease activity is present).

Mutations of a nucleic acid which encode a polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant polypeptides) which are silent as to the amino acid sequence of the polypeptide, but which provide preferred codons for translation in a particular host. The preferred codons for translation of a nucleic acid in, e.g., E. coli, are well known to those of ordinary skill in the art. Still other mutations can be made to the noncoding sequences of a gene or cDNA clone to enhance expression of the polypeptide. The activity of variant polypeptides can be tested by cloning the gene encoding the variant polypeptide into a bacterial or mammalian expression vector, introducing the vector into an appropriate host cell, expressing the variant polypeptide, and testing for a functional capability of the polypeptides as disclosed herein.

The skilled artisan will also realize that conservative amino acid substitutions may be made in polypeptides to provide functionally equivalent variants of the foregoing polypeptides, i.e., the variants retain the functional capabilities of the polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Fourth Edition, Cold Spring Harbor Laboratory Press, Cold Spring Harbor, N.Y., 2012, or Current Protocols in Molecular Biology, F. M. Ausubel, et al., eds., John Wiley & Sons, Inc., New York. Exemplary functionally equivalent variants of polypeptides include conservative amino acid substitutions in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In general, it is preferred that fewer than all of the amino acids are changed when preparing variant polypeptides. Where particular amino acid residues are known to confer function, such amino acids will in some embodiments not be replaced, or alternatively, will in some embodiments be replaced by conservative amino acid substitutions. In some embodiments, preferably, 1, 2, 3, 4, 5, 6, 7, 8, 9, 10, 11, 12, 13, 14, 15, 16, 17, 18, 19, 20 residues can be changed when preparing variant polypeptides. In some embodiments, it is generally preferred that the fewest number of substitutions is made. Thus, one method for generating variant polypeptides is to substitute all other amino acids for a particular single amino acid, then assay activity of the variant, then repeat the process with one or more of the polypeptides having the best activity.

Conservative amino-acid substitutions in the amino acid sequence of a polypeptide to produce functionally equivalent variants of the polypeptide typically are made by alteration of a nucleic acid encoding the polypeptide. Such substitutions can be made by a variety of methods known to one of ordinary skill in the art. For example, amino acid substitutions may be made by PCR-directed mutation, site-directed mutagenesis according to the method of Kunkel (Kunkel, Proc. Nat. Acad. Sci. U.S.A. 82: 488-492, 1985), or by chemical synthesis of a gene encoding a polypeptide.

It should be appreciated that some cells compatible with the invention may express an endogenous copy of one or more of the genes associated with the invention as well as a recombinant copy. In some embodiments if a cell has an endogenous copy of one or more of the genes associated with the invention then the methods will not necessarily require adding a recombinant copy of the gene(s) that are endogenously expressed. In some embodiments the cell may endogenously express one or more enzymes from the pathways described herein.

In some embodiments, one or more of the genes associated with the invention is expressed in a recombinant expression vector. As used herein, a "vector" may be any of a number of nucleic acids into which a desired sequence or sequences may be inserted by restriction and ligation for transport between different genetic environments or for expression in a host cell. Vectors are typically composed of DNA although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host cell such as a host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When a nucleic acid molecule encoding an enzyme associated with aspects of the invention is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing elements for expression are commercially available and known to those skilled in the art. See, e.g., Sambrook et al., Molecular Cloning: A Laboratory Manual, Fourth Edition, Cold Spring Harbor Laboratory Press, 2012. Cells can be genetically engineered by the introduction into the cells of heterologous nucleic acids, such as DNA or RNA. As used herein a "recombinant cell" refers to a cell that expresses heterologous nucleic acids. That heterologous nucleic acid, such as DNA or RNA can be placed under operable control of transcriptional elements to permit the expression of the heterologous DNA in the host cell. Heterologous expression of genes associated with the invention, is described in non-limiting examples of bacterial cells. As one of ordinary skill in the art would appreciate, methods disclosed herein can include other bacterial cells, and in some embodiments could include archaeal cells, fungi (including yeast cells), mammalian cells, plant cells, etc.

A nucleic acid molecule that encodes an enzyme associated with aspects of the invention can be introduced into a cell or cells using methods and techniques that are standard in the art. For example, nucleic acid molecules can be introduced by standard protocols such as transformation including chemical transformation and electroporation, transduction, particle bombardment, etc. Expressing a nucleic acid molecule encoding an enzymes associated with aspects of the invention also may be accomplished by integrating the nucleic acid molecule into the genome.

Aspects of the invention relate to expression of bacterial cells. Bacterial cells associated with the invention can be cultured in some embodiments in media of any type (rich or minimal), including fermentation medium, and any composition. As would be understood by one of ordinary skill in the art, routine optimization would allow for use of a variety of types of media. The selected medium can be supplemented with various additional components. Some non-limiting examples of supplemental components include glucose, antibiotics, IPTG for gene induction and ATCC Trace Mineral Supplement. Similarly, other aspects of the medium and growth conditions of the cells of the invention may be optimized through routine experimentation. For example, pH and temperature are non-limiting examples of factors which can be optimized. In some embodiments, factors such as choice of media, media supplements, and temperature can influence production levels of a desired molecule. In some embodiments the concentration and amount of a supplemental component may be optimized. In some embodiments, how often the media is supplemented with one or more supplemental components, and the amount of time that the media is cultured before harvesting the desired molecule is optimized.

The liquid cultures used to grow cells associated with the invention can be housed in any of the culture vessels known and used in the art. In some embodiments large scale production in a bioreactor vessel can be used to produce large quantities of a desired molecule.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The methods and techniques of the present disclosure are generally performed according to conventional methods well-known in the art. Generally, nomenclatures used in connection with, and techniques of biochemistry, enzymology, molecular and cellular biology, microbiology, genetics and protein and nucleic acid chemistry and hybridization described herein are those well-known and commonly used in the art. The methods and techniques of the present disclosure are generally performed according to conventional methods well known in the art and as described in various general and more specific references that are cited and discussed throughout the present specification unless otherwise indicated.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

EXAMPLES

Example 1

Production of Amino Acids from Feedstock Consisting of a Syngas, or Components Thereof

*Cupriavidus necator* (also known as *Ralstonia eutropha*) strains DSM 531 and DSM541 were cultured using a $H_2/CO_2/O_2$ gas mixture and mineral salt fermentation medium. The culture was grown for 96 hrs in 20 ml MSM medium (1 L Medium A: 9 g Na2HPO412H2O, 1.5 g H2PO4, 1.0 g NH4Cl and 0.2 g MgSO47H2O per 1 L; 10 ml Medium B: 50 mg Ferric ammonium citrate and 100 mg CaCl2 per 100 ml; 10 ml Medium C: 5 g NaHCO3 per 100 ml; and 1 ml Trace Mineral Solution: 100 mg ZnSO47H2O, 30 mg MnCl24H2O, 300 mg H3BO3, 200 mg COCl26H2O, 10 mg CuCl22H2O, 20 mg NiCl26H2O and 30 mg Na2MoO42H2O per 1 L) in a serum bottle supplemented with 66.7% H2, 9.5% CO2, 5% O2 and 18.8% N2 at 30° C. and 200 rpm.

Figure 5:
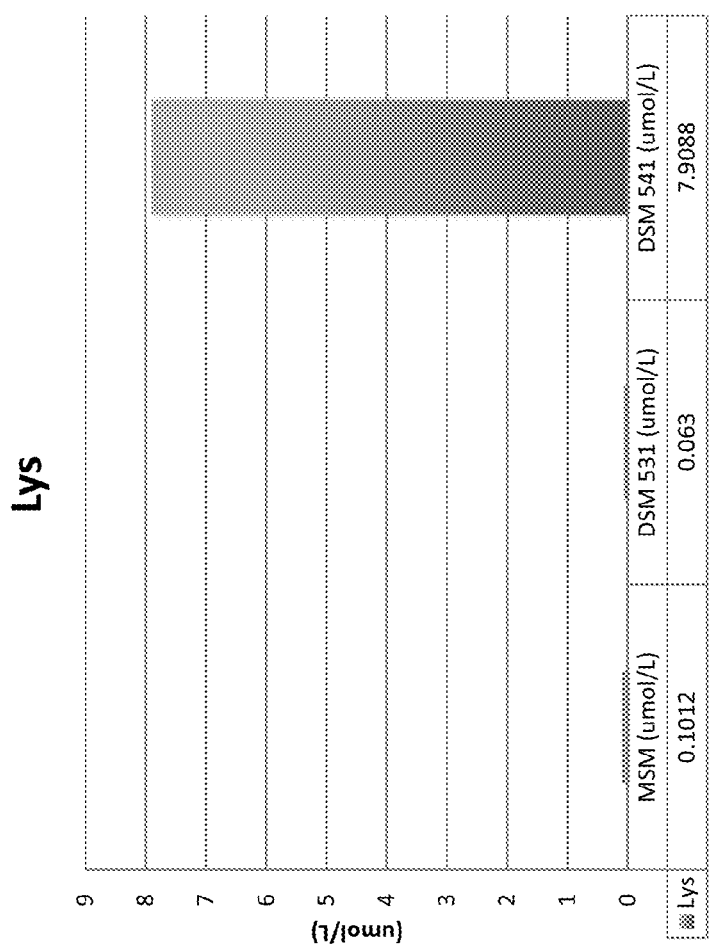
FIG. 5 shows enhanced production of Lysine in *C. necator* DSM 541 cultures.

For lysine detection in the growth media, 1 ml of the cells (O.D=0.1) were separated by centrifugation (10,000 rpm, 5 min at room temperature) and the supernatant (200 µl) was further filtrated (0.22µ). Samples of the supernatants were collected and analyzed for secretion of amino-containing compounds, such as amino acids including lysine, tyrosine, and phenylalanine, as shown in Table 2. It was observed that *C. necator* strain DSM541 secreted higher concentrations of lysine, tyrosine, and phenylalanine into the medium compared to *C. necator* strain DSM531. The analyses were performed on 200 µl of sterile filtered fermentation medium. Compounds were isolated and derivatized using a clean-up and derivatization kit (e.g. EZ-FaaST (Phenomenex) followed by liquid chromatography-mass spectrometry to separate and identify compounds that had been secreted by the bacterial strains into the medium (Table 2). The levels of lysine found in the media from DSM 541 were 125 fold higher than DSM 531. (FIG. 5).

Example 2

Production of Amino Acids from Feedstock Consisting of a Syngas, or Components Thereof, Using an Engineered Microorganism Bacterial strains can be genetically modified to increase production of amino-containing molecules such as lysine. *Ralstonia eutropha* N-1 strain DSM 13513 can be engineered to express exogenous genes or up-regulate native genes coding for enzymes involved in lysine biosynthesis such as aspartate kinase (EC 2.7.2.4, see, for example, SEQ ID NO:1) (Kalinowski et al., 1991), dihydrodipicolinate synthase (EC 4.2.1.52, see, for example, SEQ ID NO:2), (Patek et al., 1997) or in lysine secretion such as lysine exporter (Vrljic et al., 1996) (see, for example, SEQ ID NO:3). In some embodiments, increased lysine production is obtained by down-regulation of enzymes in the citric acid cycle, such as succinyl-CoA synthase (EC 6.2.1.4, see, for example, alpha subunit SEQ ID NO:4 and beta subunit SEQ ID NO:5) (Johnson et al., 1998).

Aromatic amino acids are synthesized through the Shikimate pathway. Bacterial strains are engineered to produce increased quantifies of the aromatic amino acids phenylalanine and tyrosine by over-expressing enzymes in this pathway, such as chorismate synthase (EC 4.2.3.5, SEQ ID NO:6).

*Rhodococcus opacus* PD630 produces a chorismate synthase for the production of aromatic amino acids (Holder et al., 2011). Basic Local Alignment Search Tool (BLAST) of the protein sequence of the chorismate synthase from *Rhodococcus opacus* PD360 against the NCBI nr database (All non-redundant GenBank CDS translations+PDB+SwissProt+PIR+PRF excluding environmental samples from WGS projects) reveals multiple protein sequences with high homology. As described herein, homologous proteins can be used for practice of the invention.

To generate a bacterial strain that produces increased quantities of amino acids, expression vectors are constructed. The aspartate kinase, dihydrodipicolinate synthase, and chorismate synthase genes from the *Ralstonia eutropha* are amplified from the *R. eutropha* genome using the primer pairs provided by SEQ ID NO:11 and 12, 13 and 14, and 19 and 20, respectively. The genes can also be synthesized. The cloned genes are inserted into a pBBR1MCS-derived broad host-range vector. In some embodiments, all genes are regulated by a single promoter to yield a single, polycistronic mRNA transcript. Gene expression can be modulated by placing the over-expressed genes under control of the heterologous araBAD promoter or the native rbc promoter (RuBisCO carboxylase/oxygenase promoter). Plasmid manipulation is performed in *E. coli*.

Plasmids prepared as described above are transformed into *Ralstonia eutropha* using electroporation (11.5 kV/cm, 25 µF, 5 ms). For plasmid containing an inducible promoter, the inducer molecule will be added to the culture at mid-log phase. In embodiments in which the plasmid contains the rbc promoter, the genes are expressed constitutively.

The genetically modified *Ralstonia eutropha* is grown to high cell density using a gas-based feedstock such as syngas. Bacterial cells and fermentation supernatant are separated by centrifugation at 10,000 rpm for 10 minutes. To lyse the bacterial cells, pellets are washed twice with 10 mM Tris pH 8.0 containing 10 mM EDTA (TE buffer) and resuspended in TE buffer containing 10% SDS followed by tip sonication (3×30 sec, 30% duty cycle, power level 7). Supernatant is filtered through a 0.2 micron filter. The identification and quantity of free amino acids in the cell extract and in the supernatant (secreted) are determined after purification and derivatization using a clean-up and derivatization kit (e.g., EZ-faast kit (Phenomenex, Torrance, Calif.) followed by High Performance Liquid Chromatography coupled to Mass Spectrometry (HPLC-MS).

Total bacterial protein is isolated by salt precipitation using high concentrations of $(NH_4)_2SO_4$ followed by dialysis. The isolated bacterial protein is hydrolyzed by treatment with HO, and the amino acid composition is determined following separation and quantitation by Ion-Exchange Chromatography. Results of these experiments are expected to show production of amino acids from feedstock consisting of a syngas or components thereof using overexpression in a chemoautotrophic production strain that can be grown to high cell density using a gas-based feedstock.

2.1 Enhanced Production of Lysine

*Cupriavidus necator* wild type (DSM 531) and the mutant strain that does not form poly-β-hydroxy-butyrate (DSM 541), were grown under chemoautotrophic conditions for 96 hrs in 20 ml MSM medium (1 L Medium A: 9 g Na$_2$HPO$_4$12H$_2$O, 1.5 g H$_2$PO$_4$, 1.0 g NH$_4$Cl and 0.2 g MgSO$_4$7H$_2$O per 1 L; 10 ml Medium B: 50 mg Ferric ammonium citrate and 100 mg CaCl$_2$ per 100 ml; 10 ml Medium C: 5 g NaHCO$_3$ per 100 ml; and 1 ml Trace Mineral Solution: 100 mg ZnSO$_4$7H$_2$O, 30 mg MnCl$_2$4H$_2$0, 300 mg H$_3$BO$_3$, 200 mg COCl$_2$6H$_2$0, 10 mg CuCl$_2$2H$_2$O, 20 mg NiCl$_2$6H$_2$O and 30 mg Na$_2$MoO$_4$2H$_2$O per 1 L) in a serum bottle supplemented with 66.7% H$_2$, 9.5% CO$_2$, 5% O$_2$ and 18.8% N$_2$ at 30° C. and 200 rpm.

For lysine detection in the growth media, 1 ml of the cells (O.D=0.1) were separated by centrifugation (10,000 rpm, 5 min at room temperature) and the supernatant (200 μl) was further filtrated (0.22μ). The compounds were isolated from the supernatant and derivatized using EZ-FaaST and analyzed by LC-MS. The levels of lysine found in the media from DSM 541 were 125 fold higher than DSM 531. (FIG. 5)

Example 3

Production of Putrescine from Feedstock Consisting of a Syngas, or Components Thereof

*Cupriavidus Necator* (also known as *Ralstonia eutropha*) strains DSM 531 and DSM541 were grown on an H$_2$/CO$_2$/O$_2$ gas mixture and mineral salt fermentation medium (1 L Medium A: 9 g Na2HPO412H2O, 1.5 g H2PO4, 1.0 g NH4Cl and 0.2 g MgSO47H2O per 1 L; 10 ml Medium B: 50 mg Ferric ammonium citrate and 100 mg CaCl2 per 100 ml; 10 ml Medium C: 5 g NaHCO3 per 100 ml; and 1 ml Trace Mineral Solution: 100 mg ZnSO47H2O, 30 mg MnCl24H20, 300 mg H3BO3, 200 mg COCl26H20, 10 mg CuCl22H2O, 20 mg NiCl26H2O and 30 mg Na2MoO42H2O per 1 L) for 96 hours in 20 ml medium in a serum bottle supplemented with 66.7% H2, 9.5% CO2, 5% O2 and 18.8% N2 at 30° C. and 200 rpm.

For putresine detection in the growth media, 1 ml of the cells (O.D=0.1) were separated by centrifugation (10,000 rpm, 5 min at room temperature) and the supernatant was further filtrated (0.22μ). Samples of the supernatant were collected and analyzed for secretion of putrescine into the aqueous broth, as shown in Table 2. It was observed that *C. necator* strain DSM531 secreted higher concentrations of putrescine into the medium compared to *C. necator* strain DSM541. The analyses were performed on 200 μl of sterile filtered fermentation broth. Compounds were isolated and derivatized using a clean-up and derivatization kit (e.g., EZ-FaaST (Phenomenex) followed by liquid chromatography-mass spectrometry to separate and identify the compounds that had been secreted by the bacterial strains into the medium (Table 2).

Example 4

Production of Putrescine from Feedstock Consisting of a Syngas, or Components Thereof, Using an Engineered Microorganism Bacterial strains such as *Ralstonia eutropha* N-1 strain DSM 13513 can be genetically engineered to increase production of putrescine. Biochemical synthesis of putrescine is achieved by enzymatic degradation of arginine by arginase (EC 3.5.3.1, SEQ ID N0:7), followed by enzymatic decarboxylation of ornithine in a reaction catalyzed by ornithine decarboxylase (EC 4.1.1.17, SEQ ID N0:8). *Corynebacterium glutamicum* produces an exemplary ornithine decarboxylase that can be used for the production of putrescine (Schneider and Wendisch, 2010).

To generate a bacterial strain that produces increased quantities of putrescine, expression vectors are constructed. The arginase and ornithine decarboxylase genes from *Ralstonia eutropha* are amplified from the *R. eutropha* genome using the cloning primer pairs provided by SEQ ID NO 17 and 18, and 21 and 22, respectively. Alternatively, the arginase and ornithine genes can be synthesized. The genes are inserted into a pBBR1MCS-derived broad host-range vector. In some embodiments, all genes are regulated by a single promoter to yield a single, polycistronic mRNA transcript. Gene expression can be modulated by placing the over-expressed genes under control of the heterologous araBAD promoter or the native rbc promoter (RuBisCO carboxylase/oxygenase promoter). Plasmid manipulation is performed in *E. coli*.

Plasmids prepared as described above are transformed into *Ralstonia eutropha* using electroporation (11.5 kV/cm, 25 μF, 5 ms). For plasmids containing an inducible promoter, the inducer molecule is added to the culture at mid-log phase. In embodiments in which the plasmid contains the rbc promoter, the genes are expressed constitutively.

The genetically modified *Ralstonia eutropha* is grown to high cell densities using a gas-based feedstock such as syngas. Bacterial cells and fermentation supernatant are separated by centrifugation at 10,000 rpm for 10 minutes. The recovered supernatant is filtered through a 0.2 micron filter. Production and secretion of putrescine are evaluated. The supernatant is also acidified to pH 2 to precipitate soluble proteins; the precipitate is removed by centrifugation.

The pellet of bacterial cells is washed with 0.1 M HCl in 0.25/0.75 water/methanol to recover co-precipitated putrescine hydrochloride. Putrescine purity is assessed by NMR and quantified by pH titration.

Example 5

Production of Caprolactam from Feedstock Consisting of a Syngas, or Components Thereof, Using an Engineered Microorganism Bacterial strains such as *Ralstonia eutropha* N-1 strain DSM 13513 can be genetically engineered for the production of caprolactam by expressing genes involved in the biosynthetic pathway. Biochemical synthesis of caprolactam is achieved by enzymatic conversion of lysine through the metabolic pathway: lysine→6-aminohex-2-enoic acid→6-aminocaproic acid→caprolactam. Carbon nitrogen lyase (EC 4.3.1.-) activity converts lysine into 6-aminohex-2-enoic acid (Raemarkers-Franken et al., 2011), which can then be converted into 6-aminocaproic acid using enzymes with α-β-enoate reductase (EC 1.3.1.-) activity, for example enzymes from species such as *Acremonium, Clostridium, Moorella* and *Ochrobactrum* (Raemarkers-Franken et al., 2009). An enzyme with amidohydrolase (EC 3.5.2.-) activity (Burgard et al., 2010) catalyzes the conversion of 6-aminocaproic acid to caprolactam.

In some embodiments, an enzyme with tyrosine phenol lyase activity (EC 4.1.99.2, SEQ ID NO:9) can convert tyrosine into phenol, which can then be chemically converted into benzene and caprolactam. *Erwinia herbicola* produces an exemplary tyrosine phenol lyase that can be used for the production of phenol (Mikamu et al., 2000).

Alternatively, phenol can be chemically converted to cyclohexanone which can then be converted to caprolactam.

As an additional alternative, purified lysine can be used for the chemical synthesis of caprolactam (see, for example U.S. Pat. No. 7,399,855 B2 and U.S. Patent Publication US 2010/0145003 A1; Frost 2008; Frost 2010)].

To generate a bacterial strain that produces increased quantities of caprolactam, expression vectors are constructed. Genes for the biosynthesis of caprolactam can be amplified from the genomes of appropriate microorganisms or be synthesized. The genes can be inserted into a pBBR1MCS-derived broad host-range vector. In some embodiments, all genes are regulated by a single promoter to yield a single, polycistronic mRNA transcript. Gene expression can be modulated by placing the over-expressed genes under control of the heterologous araBAD promoter or the native rbc promoter (RuBisCO carboxylase/oxygenase promoter). Plasmid manipulation is performed in E. coli.

Plasmids prepared as described above can be transformed into Ralstonia eutropha using electroporation (11.5 kV/cm, 25 μF, 5 ms). For plasmids containing an inducible promoter, the inducer molecule can be added to the culture at mid-log phase. In embodiments in which the plasmid contains the rbc promoter, the genes are expressed constitutively.

The genetically modified Ralstonia eutropha is grown to a high cell density using a gas-based feedstock such as syngas. Bacterial cells and fermentation supernatant are separated by centrifugation at 10,000 rpm for 10 minutes. The recovered supernatant is filtered through a 0.2 micron filter. Production and secretion of lysine, benzene, and caprolactam are evaluated by high-performance liquid chromatography-mass spectrometry or by gas chromatography coupled to mass spectrometry.

Secreted lysine can be purified by running the supernatant through a commercially available ion-exchange resin (e.g., DOWEX (Dow, Pittsburgh, Calif.)).

Example 6

Production of Styrene from Feedstock Consisting of a Syngas, or Components Thereof, Using an Engineered Microorganism Bacterial strains such as the *Cupriavidus necator* strain that produces amino acids described in Example 1 can be genetically engineered for the production of styrene.

Styrene can be produced from the aromatic amino acid phenylalanine through the following metabolic pathway: phenylalanine→cinnamic acid→styrene. Phenylalanine ammonium lyase (EC 4.3.1.24) activity catalyzes the conversion of phenylalanine into cinnamic acid, which can be further converted into styrene through a decarboxylation step. *Streptomyces maritimus* produces an exemplary phenylalanine ammonium lyase that can be used for the production of cinnamic acid (Piel et al., 2000). Exemplary enzymes that are compatible with the decarboxylation step include those belonging to a family of oxalate decarboxylases (EC 4.1.1.2), for example an oxalate decarboxylase from *Rhodococcus jostii* RHA1 that can produce styrene ([McLeod et al., 2006)S. In some embodiments, in order to further increase production of styrene, the endogenous styrene degradation pathway can be minimized by down-regulation of the styrene monooxygenase complex (Mooney et al., 2006).

To generate a bacterial strain that produces increased quantities of styrene, expression vectors are constructed. Genes for the biosynthesis of styrene can be amplified from the genomes of appropriate microorganisms or be synthesized. The genes can be inserted into a pBBR1MCS-derived broad host-range vector. In some embodiments, all genes can be regulated by a single promoter to yield a single, polycistronic mRNA transcript. Gene expression can in some embodiments be modulated by placing the over-expressed genes under control of the heterologous araBAD promoter or the native rbc promoter (RuBisCO carboxylase/oxygenase promoter). Plasmid manipulation is performed in E. coli.

Plasmids prepared as described above can be transformed into *Ralstonia eutropha* using electroporation (11.5 kV/cm, 25 μF, 5 ms). For plasmids containing an inducible promoter, the inducer molecule can be added to the culture at mid-log phase. In embodiments in which the plasmid contains the rbc promoter, the genes are expressed constitutively.

The genetically modified *Ralstonia eutropha* is grown to a high cell density using a gas-based feedstock such as syngas. Bacterial cells and fermentation supernatant are separated by centrifugation at 10,000 rpm for 10 minutes. The recovered supernatant is filtered through a 0.2 micron filter. Production and secretion of styrene are evaluated.

Example 7

Production of 1,3-Butanediol from Feedstock Consisting of a Syngas, or Components Thereof

*Cupriavidus necator* (also known as *Ralstonia eutropha*) strain DSM541 was cultured using a $H_2/CO_2/O_2$ gas mixture and mineral salt fermentation medium (1 L Medium A: 9 g Na2HPO412H2O, 1.5 g H2PO4, 1.0 g NH4Cl and 0.2 g MgSO47H2O per 1 L; 10 ml Medium B: 50 mg Ferric ammonium citrate and 100 mg CaCl2 per 100 ml; 10 ml Medium C: 5 g NaHCO3 per 100 ml; and 1 ml Trace Mineral Solution: 100 mg ZnSO47H2O, 30 mg MnCl24H2O, 300 mg H3BO3, 200 mg COCl26H2O, 10 mg CuCl22H2O, 20 mg NiCl26H2O and 30 mg Na2MoO42H2O per 1 L). Samples of the supernatant were collected and analyzed for the secretion of 1,3-butanediol by gas chromatography-mass spectrometry (GC-MS), as shown in FIGS. 1A and 1B.

GC-MS

For butanediol analysis, samples were injected manually using a SPME syringe (SPME fiber assembly Polydimethylsiloxane, Sigma Aldrich). Reactor broth samples were placed in 2 mL GC vials with a septum top. The SPME was injected into the samples for 30 seconds and then placed into the GC injector for 5 seconds. Compounds were detected on an Agilent 6890N GC/MS (Agilent, Santa Clara, Calif.) on a HP1 60 m column×0.25 mm ID. The injector temperature was 250° C. and was run in split mote (8:1) with an initial GC temperature of 60° C., ramp at 5° C./min to a final temp of 100° C. which was held for 5 minutes. Peak ID was accomplished through a NIST08 library search and comparison with 1,4-Butanediol standard material. Butanediol standards were prepared by adding known quantities of standard to fresh media and injecting with the same method as the broth samples.

Example 8

Production of 1,3-Butadiene from Feedstock Consisting of a Syngas, or Components Thereof, Using an Engineered Microorganism

*Cupriavidus necator* strain DSM541 can grow on a carbon-containing gas such as syngas, producer gas, CO2, carbon monoxide and mixtures of the same containing hydrogen gas, to produce polymers of 3-hydroxybutyrate (poly-3-hydroxybutyrate, P3HB). During fermentative growth, P3HB can be degraded, and 3-hydroxybutyrate and 1,3-butanediol are produced. *C. necator* strains can be genetically engineered to produce increased quantities of butadiene by introducing an exogenous oleate hydratase enzyme (EC 4.2.1.53, SEQ ID NO:10).

To generate a bacterial strain that produces increased quantities of 1,3-butadiene, expression vectors are constructed. A gene encoding an oleate hydratase can be amplified from the genomes of an appropriate microorganism or be synthesized. The gene can be inserted into a pBBR1MCS-derived broad host-range vector. Gene expression can in some embodiments be modulated by placing the over-expressed genes under control of the heterologous araBAD promoter or the native rbc promoter (RuBisCO carboxylase/oxygenase promoter). Plasmid manipulation is performed in *E. coli*.

Plasmids prepared as described above can be transformed into *Ralstonia eutropha* using electroporation (11.5 kV/cm, 25 µF, 5 ms). For plasmids containing an inducible promoter, the inducer molecule can be added to the culture at mid-log phase. In embodiments in which the plasmid contains the rbc promoter, the genes are expressed constitutively.

The genetically modified *Ralstonia eutropha* is grown to a high cell density using a gas-based feedstock such as syngas. Bacterial cells and fermentation supernatant are separated by centrifugation at 10,000 rpm for 10 minutes. The recovered supernatant is filtered through a 0.2 micron filter. Production and secretion of butadiene are evaluated.

8.1 PHB Purification and Extraction

PHB is purified and extracted according to the following methods:

Polymer Analysis

Isolation/Extraction of Polymers:

1: Add chloroform to lyophilized bacteria (6 ml of chloroform/g bacteria). Incubate at 60° C. for 4 hours.
2: Recover chloroform extract and dry down to approximately ⅓ of volume under nitrogen at 40° C.
3: Add concentrated chloroform extract to ice-cold methanol (at least a 1:4 ratio of chloroform to methanol).
4: Isolate precipitated polymers.
5: Wash by re-dissolving polymers in chloroform and precipitate with methanol (1:4 ratio). Repeat washing a couple of times.

Production of Monomers (Methanolysis):

1: Add 1 ml of chloroform and 1 ml of methanol containing 2.8 M sulfuric acid.
2: Incubate for 2 hours at 100° C.
3: Cool and add 0.5 ml of distilled water.
4: Collect organic phase containing methyl-esters.

8.2: GC-MS

For polymer analysis, compounds were detected on an Agilent 6890N GC/MS (Agilent, Santa Clara, Calif.) on a HP1 60 m column×0.25 mm ID. Samples were placed in GC vial inserts with a final volume in hexane of 50 uL. Samples were injected using an automatic injector, injector temperature was 250° C. and was run in split mote (8:1) with an initial GC temperature of 40° C., ramp at 4° C./min to a final temp of 100° C., then a ramp of 10° C./min to 225° C., finally a 20° C./min ramp to 312 C. Peak ID was accomplished through a NIST08 library.

Example 9

Production of Omega-7 Fatty Acids from Feedstock Consisting of a Syngas, or Components Thereof

*Rhodococcus opacus* strain DSM 43205 was cultured using a $H_2/CO_2/O_2$ gas mixture and mineral salt fermentation medium. The cell mass was separated from the supernatant of the culture by centrifugation. The supernatant was discarded and a chloroform/methanol (C/M) extraction was performed on the biomass pellet. Lipids were applied to Silica-60 columns, and different lipid groups were separated and eluted from the column with organic solvents including hexane, chloroform, isopropanol, methanol and acetone. Mild alkaline methylation was performed to methylate non-fatty acid lipids and acid methylation was performed to methylate fatty acids. Fatty acid methyl esters (FAMEs) were analyzed by gas chromatography-mass spectrometry (GC-MS). The GC-MS analysis revealed that *Rhodococcus opacus* strain DSM 43205 cultured with the gas mixture produced triacylglycerols, which contained high amounts of omega-7 fatty acids, including palmitoleic acid (C16:1, also known as 9-hexadecenoic acid) and vaccenic acid (C18:1, also known as 11-octadecenoic acid) as shown in FIG. 4. Analysis of the biomass showed 40% lipid content; further analysis of the lipid content showed 13% C16:1 omega 7 fatty acid (palmitoleic acid) and 21% C18:1 omega 7 fatty acid (vaccenic acid). Table 1 provides the lipid content and growth conditions for the samples presented in FIG. 4.

GC-MS

For FAME analysis, compounds were detected on an Agilent 6890N GC/MS (Agilent, Santa Clara, Calif.) on a HP1 60 m column×0.25 mm ID. Samples were placed in GC vial inserts with a final volume in hexane of 50 uL. Samples were injected using an automatic injector, the injector temperature was 250° C. and was run in split mote (8:1) with an initial GC temperature of 100° C., ramp at 10° C./min to a final temp of 150° C., then a ramp of 3° C./min to 250° C., finally a 10° C./min ramp to 312° C. which is held for 7 min. Peak ID was accomplished through a NIST08 library and comparison to known standards (Supelco 37 Component FAME Mix). Quantification was accomplished through an external standard added to each sample prior to injection (methyl undecanoate) and extraction efficiency was quantified by an internal standard (1,2-dinonadecanoyl-sn-glycero-3-phosphocholine).

TABLE 1

Lipid content of *Rhodococcus opacus* cultures.

| Strain | Growth Conditions | Sample | Total Lipid in C/M extract (% of dry wt) | Total Lipid soluble in hexane (1% of dry wt) |
|---|---|---|---|---|
| R. opacus | Gas | A | 42 | 14 |
| R. opacus | Gas | B | 27 | 3 |

Example 10

Production of Omega-7 Fatty Acids from Feedstock Consisting of a Syngas, or Components Thereof As demonstrated in Example 9 and FIG. 4, *Rhodococcus opacus* strain DSM 43205 can grow on a carbon-containing gas such as syngas, producer gas, $CO_2$, carbon monoxide and mixtures of the same containing hydrogen gas; and/or C1 compounds, to produce and accumulate lipids, including triacylglycerols, which contain high amounts of omega-7 fatty acids, including palmitoleic acid (C16:1) and vaccenic acid (C18:1).

Production of omega-7 fatty acids is further enhanced by culturing *Rhodococcus opacus* strain DSM 43205 to a high cell density using a gas feedstock, turning off the input of nitrogen nutrient (ammonium) and/or phosphorous nutrient (phosphate) to facilitate the accumulation of lipids including triacylglycerols. The cells are harvested by spinning at 10000 rpm for 10 minutes and the wet mass is applied to a lyophilizer overnight to obtain dry cell material. The lipids are extracted by adding methanol to the dry cell material and incubating at 60° C. for 30 minutes followed by the addition of 2 volumes of chloroform and shaking at 40° C. for 30 minutes. The extract is spun at 1500 rpm for 5 minutes and supernatant containing the lipids is recovered. The lipids are applied to Silica-60 columns and the different lipid groups are separated and eluted from the column with organic solvents including hexane, chloroform, isopropanol, methanol and acetone. The different lipid fractions are analyzed by gas chromatography-mass spectrometry.

g $MgSO_4 7H_2O$ per 1 L; 10 ml Medium B: 50 mg Ferric ammonium citrate and 100 mg $CaCl_2$ per 100 ml; 10 ml Medium C: 5 g $NaHCO_3$ per 100 ml; and 1 ml Trace Mineral Solution: 100 mg $ZnSO_4 7H_2O$, 30 mg $MnCl_2 4H_2O$, 300 mg $H_3BO_3$, 200 mg $COCl_2 6H_2O$, 10 mg $CuCl_2 2H_2O$, 20 mg $NiCl_2 6H_2O$ and 30 mg $Na_2MoO_4 2H_2O$ per 1 L) and found to produce and accumulate biopolymers including PHBs.

Strain DSM531 was grown to high cell density using a gas feedstock (up to optical density between 60 to 130 at 650 nm). Cells were harvested by spinning at 10000 rpm for 10 minutes. Wet mass was applied to a lyophilizer overnight to obtain dry cell material. Biopolymers were extracted by

TABLE 2

Analysis of secreted amino-compounds.

| | Compound | Blank | DSMZ 531: C. necator umol/L | DSMZ 541: C. necator umol/L | fold difference |
|---|---|---|---|---|---|
| Glu | Glutamic acid | 0.1952 | 11.556 | 40.614 | 3.5 |
| Sar | Sarcosine | 1.7232 | 2.5708 | 36.4692 | 14.2 |
| Ser | Serine | 1.7688 | 7.9428 | 35.8164 | 4.5 |
| Gly | Glycine | 9.4757 | 10.3272 | 35.0351 | 3.4 |
| Ala | Alanine | 0.6504 | 5.996 | 32.3436 | 5.4 |
| Thr | Threonine | 0.216 | 5.4152 | 22.9456 | 4.2 |
| Val | Valine | 0.0984 | 4.182 | 21.5904 | 5.2 |
| Ile | Isoleucine | 0.0272 | 2.1476 | 14.0068 | 6.5 |
| Orn | Ornithine | 0.9324 | 10.4876 | 13.056 | 1.2 |
| His | Histidine | 0.99 | 2.3816 | 12.0852 | 5.1 |
| Arg | Arginine | 0.2988 | 0.4112 | 9.3428 | 22.7 |
| Phe | Phenylalanine | 0.1 | 3.4216 | 8.6652 | 2.5 |
| Lys | Lysine | 0.1012 | 0.063 | 7.9088 | 125.5 |
| Tyr | Tyrosine | 0.386 | 2.9448 | 7.3972 | 2.5 |
| Cit | Citosine | 0.3332 | 0.6572 | 6.8248 | 10.4 |
| Asp | Asparatic acid | 2.1964 | 3.2776 | 4.6132 | 1.4 |
| Gln | Glutamine | 0.1412 | 1.2548 | 4.2944 | 3.4 |
| Pro | Proline | 0.0477 | 1.2567 | 4.1107 | 3.3 |
| Leu | Leucine | 0.054 | 2.5558 | 3.7205 | 1.5 |
| Trp | Tryptophan | 0.0352 | 0.9464 | 2.7072 | 2.9 |
| Met | Methionine | 0.0156 | 1.3944 | 1.614 | 1.2 |
| Tpr | Tpr | 0.034 | 0.5208 | 0.8052 | 1.5 |
| B-Ala | B-Alanine | 0 | 2.0904 | 0.6688 | 0.3 |
| SAM | S-Adenosylmethionine | 0 | 0 | 0.5604 | |
| SAH | S-Adenosylhomocysteine | 1.194 | 2.3232 | 0.2812 | 0.1 |
| MetSo | Methionine Sulfoxide | 0.0128 | 0.3696 | 0.2528 | 0.7 |
| Hcy-PCA | Hcy-PCA | 0.024 | 0.1944 | 0.2344 | 1.2 |
| a-AAA | a-AAA | 0.0096 | 0.2008 | 0.1492 | 0.7 |
| APA | APA | 0 | 0.0248 | 0.134 | 5.4 |
| Put | Putracine | 0.1912 | 15.0568 | 0.128 | 0.0 |
| Cys-PCA | Cys-PCA | 0.0392 | 0.7148 | 0.1272 | 0.2 |
| GSH-PCA | GSH-PCA | 0.0056 | 0.0052 | 0.0468 | 9.0 |
| Spd | Spd | 0.0652 | 0.0728 | 0.0444 | 0.6 |
| 3-His | 3-His | 0.0264 | 0.0384 | 0.0276 | 0.7 |
| Cy2 | Cy2 | 0.0364 | 0.0628 | 0.0128 | 0.2 |
| Cth | Cth | 0.0072 | 0.0072 | 0.0124 | 1.7 |
| CysGly-PCA | CysGly-PCA | 0.002 | 0.01 | 0.0112 | 1.1 |
| Erg | Erg | 0.0076 | 0.0512 | 0.0084 | 0.2 |
| Hcy2 | Hcy2 | 0.0116 | 0.008 | 0.0048 | 0.6 |

Example 11

Production of Polyhydroxybutyrate (PHB) from Feedstock Consisting of a Syngas or Components Thereof

*Cupriavidus Necator* (also known as *Ralstonia eutropha*) strain DSM531 was cultured using a $H_2/CO_2/O_2$ gas mixture and mineral salt fermentation medium (1 L Medium A: 9 g $Na_2HPO_4 12H_2O$, 1.5 g $H_2PO_4$, 1.0 g $NH_4Cl$ and 0.2 adding chloroform to the dry cell material and incubating at 60 degrees Celsius for 4 hours. Extract was spun at 1500 rpm for 5 minutes and supernatant containing the extracted biopolymers was recovered. Supernatant was concentrated under nitrogen and biopolymers was precipitated and recovered by adding concentrated supernatant to 4 volumes of ice-cold methanol and spinning at 1500 rpm for 5 minutes (FIG. 2). Recovered biopolymers were re-dissolved in chloroform. Monomer production was facilitated by adding methanol and sulfuric acid and incubation at 100 degrees Celsius for 2 hours. Following the addition of water to create a 2-phase extraction system, the monomeric methyl-ester was isolated in the organic phase and analyzed by GC/MS (FIG. 3A-3D).

Polymer Analysis

Isolation/Extraction of Polymers:

1: Added chloroform to lyophilized bacteria (6 ml of chloroform/g bacteria). Incubated at 60° C. for 4 hours.
2: Recovered chloroform extract and dried down to approximately ⅕ of volume under nitrogen at 40° C.
3: Added concentrated chloroform extract to ice-cold methanol (at least a 1:4 ratio of chloroform to methanol).
4: Isolated precipitated polymers.
5: Washed by re-dissolving polymers in chloroform and precipitate with methanol (1:4 ratio). Repeated washing a couple of times.

Production of Monomers (Methanolysis):

1: Added 1 ml of chloroform and 1 ml of methanol containing 2.8 M sulfuric acid.
2: Incubated for 2 hours at 100° C.
3: Cooled and added 0.5 ml of distilled water.
4: Collected organic phase containing methyl-esters.

GC-MS

For polymer analysis, compounds were detected on an Agilent 6890N GC/MS (Agilent, Santa Clara, Calif.) on a HP1 60 m column×0.25 mm ID. Samples were placed in GC vial inserts with a final volume in hexane of 50 uL. Samples were injected using an automatic injector, injector temperature was 250° C. and was run in split mote (8:1) with an initial GC temperature of 40° C., ramp at 4° C./min to a final temp of 100° C., then a ramp of 10° C./min to 225° C., finally a 20° C./min ramp to 312 C. Peak ID was accomplished through a NIST08 library.

Example 12

Increasing Production of Polyhydroxybutyrate (PHB) from Feedstock Consisting of a Syngas or Components Thereof

*Cupriavidus Necator* (also known as *Ralstonia eutropha*) strain DSM531) can grow on a carbon-containing gas such as syngas, producer gas, CO2, carbon monoxide and mixtures of the same containing hydrogen gas; and/or C1 compounds to produce and accumulate biopolymers including PHBs.

Strain DSM531 can be grown to high cell density using a gas feedstock (over optical density at 650 nm). The input of nitrogen nutrient (ammonium) and/or phosphorous nutrient (phosphate) is turned off to facilitate the accumulation of biopolymers including PHBs. Cells are harvested by spinning at 10000 rpm for 10 minutes. Wet mass is applied to a lyophilizer overnight to obtain dry cell material. Biopolymers are extracted by adding chloroform to the dry cell material and incubating at 60 degrees Celsius for 4 hours. Extract is spun at 1500 rpm for 5 minutes and supernatant containing the extracted biopolymers is recovered. Supernatant is concentrated under nitrogen and biopolymers are precipitated and recovered by adding concentrated supernatant to 4 volumes of ice-cold methanol and spinning at 1500 rpm for 5 minutes. Recovered biopolymers are re-dissolved in chloroform. Monomer production is facilitated by adding methanol and sulfuric acid and incubation at 100 degrees Celsius for 2 hours. Following the addition of water to create a 2-phase extraction system, the monomeric methyl-ester is isolated in the organic phase and analyzed by GC/MS.

Polymer Analysis

Isolation/Extraction of Polymers:

1: Add chloroform to lyophilized bacteria (6 ml of chloroform/g bacteria). Incubate at 60° C. for 4 hours.
2: Recover chloroform extract and dry down to approximately ⅕ of volume under nitrogen at 40° C.
3: Add concentrated chloroform extract to ice-cold methanol (at least a 1:4 ratio of chloroform to methanol).
4: Isolate precipitated polymers.
5: Wash by re-dissolving polymers in chloroform and precipitate with methanol (1:4 ratio). Repeat washing a couple of times.

Production of Monomers (Methanolysis):

1: Add 1 ml of chloroform and 1 ml of methanol containing 2.8 M sulfuric acid.
2: Incubate for 2 hours at 100° C.
3: Cool and add 0.5 ml of distilled water.
4: Collect organic phase containing methyl-esters.

GC-MS

For polymer analysis, compounds are detected on an Agilent 6890N GC/MS (Agilent, Santa Clara, Calif.) on a HP1 60 m column×0.25 mm ID. Samples are placed in GC vial inserts with a final volume in hexane of 50 uL. Samples are injected using an automatic injector, injector temperature is 250° C. and is run in split mote (8:1) with an initial GC temperature of 40° C., ramp at 4° C./min to a final temp of 100° C., then a ramp of 10° C./min to 225° C., finally a 20° C./min ramp to 312 C. Peak ID is accomplished through a NIST08 library.

REFERENCES

Burgard et al., 2010. Microorganisms for the production of adipic acid and other compounds. U.S. Pat. No. 7,799,545 B2.

Frost 2008. Synthesis of caprolactam from lysine. U.S. Pat. No. 7,399,855 B2.

Frost 2010. Catalytic deamination for caprolactam production. Patent # US 2010/0145003 A1.

Holder et al., 2011. Comparative and functional genomics of *Rhodococcus opacus* PD630 for biofuel development. PLoS Genet. (9) e-pub: E1002219.

Johnson et al., 1998. Genetic evidence for the expression of ATP- and GTP-specific succinyl-coA synthetases in multicellular eukaryotes. J. Biol. Chem. (273) 27580-6.

Kalinowski et al., 1991. Genetic and biochemical analysis of the aspartokinase from *Corynebacterium glutamicum*. Mol. Microbiol. (5) 1197-1204.

Mikami et al., 2000. Tyrosine phenol-lyase from *Erwinia herbicola*. Protein databank entry ID #1C7G.

Patek et al., 1997. Identification and transcriptional analysis of the dapB-orf2-dapA-orf4 operon of *Corynebacterium glutamicum*, encoding two enzymes involved in 1-lysine synthesis. Biotech. Letters 19 (11) 1113-17.

Piel et al., 2000. Cloning, sequencing and analysis of the enterocin biosynthesis gene cluster from the marine isolate '*Streptomyces maritimus*': evidence for the derailment of an aromatic polyketide synthase. Chem. Biol. (7) 943-55.

Raemakers-Franken et al., 2009. Biochemical synthesis of 6-aminocaproic acid. U.S. Pat. No. 7,491,520 B2.

Raemakers-Franken et al., 2011. Methods of finding a biocatalyst having ammonia lyase activity. Patent App # WO/2011/078667.

Schneider and Wendisch, 2010. Putrescine production by engineered *Corynebacterium glutamicum*. Appl. Microbiol. Biotechnol. (88) 859-68.

Vrljic et al., 1996. A new type of transporter with a new type of cellular function: I-lysine export from *Corynebacterium glutamicum*. Mol. Microbiol. (22) 815-26.

What is claimed is:

1. A method for the production of omega-7 fatty acids from feedstock comprising syngas, the process comprising passing said syngas to a bioreactor for contact therein with chemoautotrophic *Rhodococcus* microorganisms DSM 3346 or DSM 43205, wherein said *Rhodococcus* microorganisms convert said syngas into omega-7 fatty acids in said bioreactor and produce a cell mass.

2. The method of claim 1 further comprising separating the cell mass from a supernatant by centrifugation to create a biomass pellet.

3. The method of claim 2 wherein the biomass pellet contains omega-7 fatty acids.

4. The method of claim 3 wherein the omega-7 fatty acids comprise palmitoleic acid (C16:1) and vaccenic acid (C18:1).

5. The method of claim 2 further comprising an extraction step wherein the supernatant is discarded and lipids are eluted from the biomass pellet with an organic solvent.

6. The method of claim 5 wherein the organic solvent is selected from a group comprising: hexane, chloroform, isopropanol, methanol, and acetone.

7. The method of claim 1 wherein the microorganism is a *Rhodococcus opacus* strain.

* * * * *

SEQUENCE LISTING

<160> NUMBER OF SEQ ID NOS: 22

<210> SEQ ID NO 1
<211> LENGTH: 416
<212> TYPE: PRT
<213> ORGANISM: Cupriavidus necator

<400> SEQUENCE: 1

```
Met Ala Leu Ile Val His Lys Tyr Gly Gly Thr Ser Met Gly Ser Thr
 1               5                  10                  15

Glu Arg Ile Lys Asn Val Ala Lys Arg Val Ala Lys Trp His Arg Ala
            20                  25                  30

Gly His Arg Val Val Val Val Pro Ser Ala Met Ser Gly Glu Thr Asn
        35                  40                  45

Arg Leu Leu Gly Leu Ala Lys Glu Ile Ser Pro Gln Pro Asn Pro Arg
    50                  55                  60

Glu Leu Asp Met Leu Ala Ser Thr Gly Glu Gln Ala Ser Val Ala Leu
65                  70                  75                  80

Leu Ala Ile Ala Leu His Gly Glu Asp Ile Asp Ala Val Ser Tyr Thr
                85                  90                  95

Gly Trp Gln Val Pro Val Lys Thr Asp Ser Ala Tyr Thr Lys Ala Arg
            100                 105                 110

Ile Glu Ser Ile Asp Asp Glu Arg Ile Leu Ala Asp Leu Asp Ala Gly
        115                 120                 125

Arg Val Val Val Ile Thr Gly Phe Gln Gly Ile Asp Asp Asp Gly Asn
    130                 135                 140

Ile Thr Thr Leu Gly Arg Gly Gly Ser Asp Thr Ser Ala Val Ala Ile
145                 150                 155                 160

Ala Ala Ala Ile Glu Ala Asp Glu Cys Leu Ile Tyr Thr Asp Val Asp
                165                 170                 175

Gly Val Tyr Thr Thr Asp Pro Arg Val Val Glu Asp Ala Arg Arg Leu
            180                 185                 190

Asp Gln Ile Thr Phe Glu Glu Met Leu Glu Met Ala Ser Leu Gly Ser
        195                 200                 205

Lys Val Leu Gln Ile Arg Ser Val Glu Phe Ala Gly Lys Tyr Arg Val
    210                 215                 220

Lys Thr Arg Val Leu Ser Ser Leu Thr Asp Pro Leu Met Pro Leu Glu
225                 230                 235                 240

Gln Glu Met His Ser Gly Thr Leu Ile Thr Phe Glu Glu Asp Ser Thr
                245                 250                 255

Met Glu Ala Ala Val Ile Ser Gly Ile Ala Phe Ala Arg Asp Glu Ala
            260                 265                 270

Lys Ile Thr Val Leu Gly Val Pro Asp Lys Pro Gly Ile Ala Tyr Gln
        275                 280                 285

Ile Leu Gly Pro Val Ala Asp Ala Asn Ile Asp Val Asp Met Ile Ile
    290                 295                 300

Gln Asn Gln Ser Val Asp Gly Lys Thr Asp Phe Thr Phe Thr Val Pro
305                 310                 315                 320

Arg Gly Glu Tyr Gln Arg Ala Leu Ala Ile Leu Asn Asp Gly Val Lys
                325                 330                 335

Ser His Ile Gly Ala Gly Ser Val Ser Gly Asp Pro Lys Val Ser Lys
            340                 345                 350

Val Ser Val Val Gly Val Gly Met Arg Ser His Val Gly Ile Ala Ser
        355                 360                 365
```

```
Lys Met Phe Arg Thr Leu Ser Glu Glu Gly Ile Asn Ile Gln Met Ile
        370                 375                 380
Ser Thr Ser Glu Ile Lys Ile Ser Val Leu Ile Asp Glu Lys Tyr Met
385                 390                 395                 400
Glu Leu Ala Val Arg Ala Leu His Lys Ala Phe Glu Leu Glu Gln Ala
                405                 410                 415

<210> SEQ ID NO 2
<211> LENGTH: 304
<212> TYPE: PRT
<213> ORGANISM: Cupriavidus necator

<400> SEQUENCE: 2

Met Asn Asn Lys Leu Thr Ala Ala Asp Leu Arg Gly Ile Phe Pro Ala
1               5                   10                  15
Ile Pro Thr Pro Val Thr Ala Asp Asp Arg Ile Asp Gln Asp Ala Thr
            20                  25                  30
Arg Lys Leu Met Ala Tyr Leu Leu Ala Asn Gly Val Ser Gly Val Val
        35                  40                  45
Pro Leu Gly Gly Thr Gly Glu Tyr Gly Ala Leu Ala Arg Glu Glu Arg
    50                  55                  60
Val Arg Met Ala Ala Leu Cys Val Glu Ala Ala Gly Gln Val Pro
65                  70                  75                  80
Val Ile Pro Gly Val Leu Asp Pro Gly Phe His Asp Ala Leu Asp Ala
                85                  90                  95
Gly Lys Ala Phe Ala Gly Val Gly Ala Ser Ala Leu Met Val Leu Thr
            100                 105                 110
Pro Tyr Tyr Thr Ser Pro Thr Gln Gln Gly Ile Arg Asp Tyr Phe Leu
        115                 120                 125
Arg Tyr Ala Asp Ala Ser Pro Val Pro Val Met Ile Tyr Glu Ile Pro
    130                 135                 140
Tyr Arg Thr Arg Ile Ala Ile Ala Pro Glu Val Leu His Glu Leu Ser
145                 150                 155                 160
Arg His Glu Asn Ile Ile Gly Met Lys Ala Cys Asn Thr Asp Met Tyr
                165                 170                 175
His Phe Leu Lys Val Val Ala Gly Val Asp Asp Ser Phe Ser Val Phe
            180                 185                 190
Ser Gly Glu Asp Ser Leu Phe Pro Leu His Met Ala Gly Gly Ala Arg
        195                 200                 205
Gly Gly Val Val Val Thr Ala Ser Val Leu Pro Arg Thr Trp Arg Ala
    210                 215                 220
Ile Tyr Glu Leu Gly Val Ala Gly Asn Thr Ala Gln Ala Val Arg Leu
225                 230                 235                 240
His Arg Glu Leu Ile Pro Leu Leu Asp Leu Ala Phe Ser Glu Thr Asn
                245                 250                 255
Pro Gly Pro Leu Lys Ser Val Leu Asp Leu Val Gly Val Thr Ala Pro
            260                 265                 270
Lys Val Leu Ala Pro Leu Val Ala Pro Ala Pro Gly Leu Gln Ala Gln
        275                 280                 285
Leu Arg Ala Glu Leu Thr Gln Arg Leu Gln Ala Glu Ala Ala Leu Ala
    290                 295                 300

<210> SEQ ID NO 3
<211> LENGTH: 216
<212> TYPE: PRT
<213> ORGANISM: Ralstonia eutropha
```

```
<400> SEQUENCE: 3

Met Asn Ser Leu Pro Asp Thr Ala Ser Leu Ala Leu Ser Ile Ala Leu
1               5                   10                  15

Gln Gly Leu Ala Leu Ser Leu Gly Leu Ile Val Ala Ile Gly Ala Gln
            20                  25                  30

Asn Ala Phe Val Leu Arg Gln Gly Leu Arg Arg Gln His Val Gly Ser
        35                  40                  45

Val Val Leu Phe Cys Ala Ala Asp Ala Leu Leu Ile Ala Ala Gly
    50                  55                  60

Val Met Gly Met Ala Gln Ala Leu Gly Asp Arg Pro Gly Leu Ala Arg
65                  70                  75                  80

Ala Leu Ala Val Ala Gly Ser Val Phe Leu Ala Ile Tyr Gly Trp Gln
                85                  90                  95

Ala Leu Gln Arg Ala Arg Gln Ser His Gln Leu Lys Ala Ala Asp Gly
            100                 105                 110

Val Asp Gly Leu Gly Arg Gly Ala Val Leu Ala Gln Ala Ala Phe
            115                 120                 125

Thr Leu Leu Asn Pro His Val Tyr Leu Asp Thr Val Leu Leu Val Gly
130                 135                 140

Ser Ile Gly Ala Gln Gln Pro Ala Ala Leu Arg Gly Trp Phe Val Ala
145                 150                 155                 160

Gly Ala Ser Ala Ala Ser Leu Phe Trp Phe Gly Leu Leu Gly Phe Gly
                165                 170                 175

Ala Arg Trp Leu Ala Pro Trp Phe Ala Arg Pro Lys Ala Trp Arg Val
            180                 185                 190

Leu Asp Gly Val Ile Ala Met Thr Met Phe Val Leu Ser Ala Leu Leu
            195                 200                 205

Val Arg His Val Phe Asn Ala Val
    210                 215

<210> SEQ ID NO 4
<211> LENGTH: 293
<212> TYPE: PRT
<213> ORGANISM: Ralstonia eutropha

<400> SEQUENCE: 4

Met Ser Ile Leu Ile Asn Lys Asp Thr Lys Val Ile Thr Gln Gly Ile
1               5                   10                  15

Thr Gly Lys Thr Gly Gln Phe His Thr Arg Gly Cys Arg Asp Tyr Ala
            20                  25                  30

Asn Gly Lys Asn Cys Phe Val Ala Gly Val Asn Pro Lys Lys Ala Gly
        35                  40                  45

Glu Asp Phe Glu Gly Ile Pro Ile Tyr Ala Ser Val Lys Asp Ala Lys
    50                  55                  60

Ala Gln Thr Gly Ala Thr Val Ser Val Ile Tyr Val Pro Pro Ala Gly
65                  70                  75                  80

Ala Ala Ala Ala Ile Trp Glu Ala Val Asp Ala Asp Leu Asp Leu Val
                85                  90                  95

Val Cys Ile Thr Glu Gly Ile Pro Val Arg Asp Met Met Glu Val Lys
            100                 105                 110

Asp Arg Met Arg Arg Glu Asn Lys Lys Thr Leu Leu Leu Gly Pro Asn
        115                 120                 125

Cys Pro Gly Leu Ile Thr Pro Asp Glu Ile Lys Ile Gly Ile Met Pro
    130                 135                 140
```

```
Gly His Ile His Arg Lys Gly Arg Ile Gly Val Val Ser Arg Ser Gly
145                 150                 155                 160

Thr Leu Thr Tyr Glu Ala Val Gly Gln Leu Thr Ala Leu Gly Leu Gly
            165                 170                 175

Gln Ser Ser Ala Val Gly Ile Gly Gly Asp Pro Ile Asn Gly Leu Lys
        180                 185                 190

His Ile Asp Val Met Lys Met Phe Asn Asp Pro Glu Thr Asp Ala
    195                 200                 205

Val Val Met Ile Gly Glu Ile Gly Gly Pro Asp Glu Ala Asn Ala Ala
        210                 215                 220

Tyr Trp Ile Lys Asp Asn Met Lys Lys Pro Val Val Gly Phe Ile Ala
225                 230                 235                 240

Gly Val Thr Ala Pro Pro Gly Lys Arg Met Gly His Ala Gly Ala Leu
                245                 250                 255

Ile Ser Gly Gly Ala Asp Thr Ala Gln Ala Lys Leu Glu Ile Met Glu
            260                 265                 270

Ala Cys Gly Ile Thr Val Thr Lys Asn Pro Ser Glu Met Ala Arg Leu
        275                 280                 285

Leu Lys Ala Lys Leu
    290

<210> SEQ ID NO 5
<211> LENGTH: 389
<212> TYPE: PRT
<213> ORGANISM: Ralstonia eutropha

<400> SEQUENCE: 5

Met Asn Ile His Glu Tyr Gln Gly Lys Glu Ile Leu Arg Lys Tyr Asn
1               5                   10                  15

Val Pro Val Pro Arg Gly Ile Pro Ala Phe Ser Val Ala Glu Ala Leu
            20                  25                  30

Lys Ala Ala Glu Glu Leu Gly Gly Pro Val Trp Val Val Lys Ala Gln
        35                  40                  45

Ile His Ala Gly Gly Arg Gly Lys Gly Gly Gly Val Lys Val Ala Lys
    50                  55                  60

Ser Ile Asp Asp Val Lys Thr Tyr Ala Thr Asn Ile Leu Gly Met Gln
65                  70                  75                  80

Leu Val Thr His Gln Thr Gly Pro Glu Gly Lys Lys Val Asn Arg Leu
                85                  90                  95

Leu Ile Glu Glu Gly Ala Asp Ile Lys Lys Glu Leu Tyr Val Ser Leu
            100                 105                 110

Val Val Asp Arg Val Ser Gln Lys Ile Ala Leu Met Ala Ser Ser Glu
        115                 120                 125

Gly Gly Met Asp Ile Glu Glu Val Ala Ala His Thr Pro Glu Lys Ile
    130                 135                 140

His Thr Leu Ile Ile Glu Pro Ser Thr Gly Leu Thr Asp Ala Asp Ala
145                 150                 155                 160

Asp Asp Ile Ala Arg Lys Ile Gly Val Pro Asp Ala Ser Val Ala Gln
                165                 170                 175

Ala Arg Gln Ala Leu Gln Gly Leu Tyr Lys Ala Phe Tyr Asp Thr Asp
            180                 185                 190

Ala Ser Leu Ala Glu Ile Asn Pro Leu Ile Leu Thr Gly Glu Gly Lys
        195                 200                 205

Val Ile Ala Leu Asp Ala Lys Phe Asn Phe Asp Ser Asn Ala Leu Phe
```

```
                    210                 215                 220
Arg His Pro Glu Ile Val Ala Tyr Arg Asp Leu Asp Glu Glu Asp Ala
225                 230                 235                 240

Asn Glu Ile Glu Ala Ser Lys Phe Asp Leu Ala Tyr Ile Ser Leu Asp
                245                 250                 255

Gly Asn Ile Gly Cys Leu Val Asn Gly Ala Gly Leu Ala Met Ala Thr
                260                 265                 270

Met Asp Thr Ile Lys Leu Phe Gly Gly Glu Pro Ala Asn Phe Leu Asp
                275                 280                 285

Val Gly Gly Gly Ala Thr Thr Glu Lys Val Thr Glu Ala Phe Lys Leu
290                 295                 300

Met Leu Lys Asn Pro Asn Val Glu Ala Ile Leu Val Asn Ile Phe Gly
305                 310                 315                 320

Gly Ile Met Arg Cys Asp Val Ile Ala Glu Gly Val Ile Ser Ala Ser
                325                 330                 335

Lys Ala Val Asn Leu Thr Val Pro Leu Val Val Arg Met Lys Gly Thr
                340                 345                 350

Asn Glu Asp Leu Gly Lys Lys Met Leu Ala Asp Ser Gly Leu Pro Ile
                355                 360                 365

Ile Ala Ala Asp Thr Met Glu Glu Ala Ala Gln Lys Val Val Ala Ala
                370                 375                 380

Ala Ala Gly Lys Lys
385

<210> SEQ ID NO 6
<211> LENGTH: 370
<212> TYPE: PRT
<213> ORGANISM: Ralstonia eutropha

<400> SEQUENCE: 6

Met Ser Gly Asn Thr Leu Gly Leu Leu Phe Thr Val Thr Thr Phe Gly
1               5                   10                  15

Glu Ser His Gly Pro Ala Ile Gly Ala Val Val Asp Gly Cys Pro Pro
                20                  25                  30

Gly Met Asp Leu Thr Glu Ala Asp Ile Gln Gly Asp Leu Asp Arg Arg
            35                  40                  45

Lys Pro Gly Thr Ser Arg His Val Thr Gln Arg Lys Glu Pro Asp Gln
        50                  55                  60

Val Glu Ile Leu Ser Gly Val Phe Glu Gly Lys Thr Thr Gly Thr Pro
65                  70                  75                  80

Ile Cys Leu Leu Ile Arg Asn Thr Asp Gln Arg Ser Lys Asp Tyr Gly
                85                  90                  95

Asn Ile Val Glu Thr Phe Arg Pro Gly His Ala Asp Tyr Thr Tyr Trp
                100                 105                 110

Gln Lys Tyr Gly Ile Arg Asp Tyr Arg Gly Gly Gly Arg Ser Ser Ala
            115                 120                 125

Arg Leu Thr Ala Pro Val Val Ala Ala Gly Ala Val Ala Lys Lys Trp
        130                 135                 140

Leu Arg Glu Gln Phe Gly Thr Glu Ile Arg Gly Tyr Met Ser Lys Leu
145                 150                 155                 160

Gly Glu Ile Glu Val Pro Phe Ser Asp Trp Ser His Val Pro Glu Asn
                165                 170                 175

Pro Phe Phe Ala Ala Asn Ala Asp Ile Val Pro Glu Leu Glu Thr Tyr
                180                 185                 190
```

Met Asp Ala Leu Arg Arg Asp Gly Asp Ser Val Gly Ala Arg Ile Glu
            195                 200                 205

Val Val Ala Ser Asn Val Pro Val Gly Leu Gly Glu Pro Leu Phe Asp
    210                 215                 220

Arg Leu Asp Ala Asp Ile Ala His Ala Met Met Gly Leu Asn Ala Val
225                 230                 235                 240

Lys Gly Val Glu Ile Gly Ala Gly Phe Lys Ser Val Glu Gln Arg Gly
                245                 250                 255

Ser Glu His Gly Asp Glu Leu Thr Ala Gln Gly Phe Arg Gly Asn Asn
            260                 265                 270

Ala Gly Gly Ile Leu Gly Gly Ile Ser Thr Gly Gln Asp Ile Thr Val
        275                 280                 285

Ser Leu Ala Ile Lys Pro Thr Ser Ser Ile Arg Thr Pro Arg Glu Ser
    290                 295                 300

Ile Asp Lys Ala Gly Asn Ala Ala Thr Val Glu Thr Phe Gly Arg His
305                 310                 315                 320

Asp Pro Cys Val Gly Ile Arg Ala Thr Pro Ile Ala Glu Ala Leu Leu
                325                 330                 335

Ala Leu Val Leu Val Asp His Ala Leu Arg His Arg Ala Gln Cys Gly
            340                 345                 350

Asp Val Lys Val Asp Thr Pro Arg Ile Pro Ala Gln Ala Pro Gly Gln
        355                 360                 365

Pro Gly
    370

<210> SEQ ID NO 7
<211> LENGTH: 304
<212> TYPE: PRT
<213> ORGANISM: Ralstonia eutropha

<400> SEQUENCE: 7

Met Lys Pro Ile Thr Leu Phe Gly Ala Pro Thr Asp Val Gly Ala Ser
1               5                   10                  15

Thr Arg Gly Cys Thr Met Gly Pro Glu Ala Leu Arg Ile Ala Asp Ile
                20                  25                  30

Val Pro Ala Leu Ala Arg Met Gly Leu Asp Val Ser Asp Ala Gly Asn
            35                  40                  45

Ile Ala Gly Pro Val Asn Pro Leu Ala Pro Val Gln Gly Leu Arg
        50                  55                  60

His Leu Asp Glu Val Val Ala Trp Asn Arg Gly Val Phe Glu Ala Ser
65                  70                  75                  80

Thr Arg Ile Leu Gln Ala Gly Arg Met Pro Val Leu Leu Gly Gly Asp
                85                  90                  95

His Cys Leu Ala Val Gly Ser Val Ser Ala Val Ala Arg His Cys Arg
            100                 105                 110

Glu Ala Gly Arg Lys Leu Val Val Leu Trp Leu Asp Ala His Ala Asp
        115                 120                 125

Ala Asn Ile Gly Thr Ser Thr Pro Thr Gly Asn Met His Gly Met Pro
    130                 135                 140

Val Ala Cys Leu Cys Gly Asp Gly Pro Thr Pro Leu Thr Thr Leu Gly
145                 150                 155                 160

Gly Gln Pro Pro Ala Val Arg Pro Glu Glu Ile Arg Gln Val Gly Ile
                165                 170                 175

Arg Ser Val Asp Ala Gln Glu Lys Leu Arg Leu His Ala Leu Gly Leu
            180                 185                 190

Lys Val Phe Asp Met Arg Tyr Ile Asp Glu Tyr Gly Met Arg Gln Thr
            195                 200                 205

Met Glu Gln Ala Leu Ala Gly Val Asp Asp Thr His Leu His Val
    210                 215                 220

Ser Phe Asp Val Asp Phe Ile Asp Ser Ala Ile Ala Pro Gly Val Gly
225                 230                 235                 240

Thr Thr Val Leu Gly Gly Pro Thr Tyr Arg Glu Thr Gln Leu Cys Met
                245                 250                 255

Glu Met Ile Ala Asp Thr Gly Arg Leu Ser Ser Leu Asp Val Met Glu
                260                 265                 270

Leu Asn Pro Ala Cys Asp Val Arg Asn Glu Thr Ala Arg Leu Val Val
            275                 280                 285

Asp Phe Leu Glu Ser Leu Phe Gly Lys Ser Thr Leu Leu Arg Ala Arg
290                 295                 300

<210> SEQ ID NO 8
<211> LENGTH: 756
<212> TYPE: PRT
<213> ORGANISM: Ralstonia eutropha

<400> SEQUENCE: 8

Met Lys Phe Arg Phe Pro Val Ile Ile Asp Glu Asp Phe Arg Ser
1               5                   10                  15

Glu Asn Ile Ser Gly Ser Gly Ile Arg Ala Leu Ala Glu Ala Ile Glu
                20                  25                  30

Lys Glu Gly Met Glu Val Met Gly Leu Thr Ser Tyr Gly Asp Leu Thr
            35                  40                  45

Ser Phe Ala Gln Gln Ser Ser Arg Ala Ser Thr Phe Ile Val Ser Ile
    50                  55                  60

Asp Asp Asp Glu Phe Val Thr Ala Asp Gln Pro Glu Ala Ala Ala
65                  70                  75                  80

Ile Glu Lys Leu Arg Ala Phe Val Asn Glu Val Arg Arg Arg Asn Thr
                85                  90                  95

Asp Leu Pro Ile Phe Leu Tyr Gly Glu Thr Arg Thr Ser Arg His Ile
            100                 105                 110

Pro Asn Asp Ile Leu Arg Glu Leu His Gly Phe Ile His Met Phe Glu
    115                 120                 125

Asp Thr Pro Glu Phe Val Ala Arg His Ile Ile Arg Glu Ala Lys Val
130                 135                 140

Tyr Leu Asp Thr Leu Ala Pro Pro Phe Phe Lys Ala Leu Ile Asp Tyr
145                 150                 155                 160

Ala Gln Asp Ser Ser Tyr Ser Trp His Cys Pro Gly His Ser Gly Gly
                165                 170                 175

Val Ala Phe Leu Lys Ser Pro Val Gly Gln Val Phe His Gln Phe Phe
            180                 185                 190

Gly Glu Asn Met Leu Arg Ala Asp Val Cys Asn Ala Val Asp Glu Leu
    195                 200                 205

Gly Gln Leu Leu Asp His Thr Gly Pro Val Ala Ala Ser Glu Arg Asn
210                 215                 220

Ala Ala Arg Ile Phe Asn Ser Asp His Met Phe Phe Val Thr Asn Gly
225                 230                 235                 240

Thr Ser Thr Ser Asn Lys Met Val Trp His Ala Asn Val Ala Pro Gly
                245                 250                 255

Asp Ile Val Val Val Asp Arg Asn Cys His Lys Ser Ile Leu His Ala

```
                260                 265                 270
Ile Met Met Thr Gly Ala Ile Pro Val Phe Leu Met Pro Thr Arg Asn
            275                 280                 285
His Tyr Gly Ile Ile Gly Pro Ile Pro Lys Ser Glu Phe Asp Pro Glu
        290                 295                 300
Thr Ile Arg Arg Lys Ile Ala Asn His Pro Phe Ala Ser Lys Ala Lys
305                 310                 315                 320
Asn Gln Lys Pro Arg Ile Leu Thr Ile Thr Gln Gly Thr Tyr Asp Gly
                325                 330                 335
Val Leu Tyr Asn Ala Glu Gln Ile Lys Glu Met Leu Ala Ser Glu Ile
            340                 345                 350
Asp Thr Leu His Phe Asp Glu Ala Trp Leu Pro His Ala Ala Phe His
        355                 360                 365
Glu Phe Tyr His Asn Met His Ala Ile Gly Arg Asp Arg Pro Arg Ser
    370                 375                 380
Lys Asp Ala Leu Val Phe Ala Thr Gln Ser Thr His Lys Leu Leu Ala
385                 390                 395                 400
Gly Leu Ser Gln Ala Ser Gln Ile Leu Val Gln Asp Ser Glu Thr Arg
                405                 410                 415
Lys Leu Asp Arg Tyr Arg Phe Asn Glu Ala Tyr Leu Met His Thr Ser
            420                 425                 430
Thr Ser Pro Gln Tyr Ala Ile Ile Ala Ser Cys Asp Val Ala Ala Ala
        435                 440                 445
Met Met Glu Ala Pro Gly Gly Pro Ala Leu Val Glu Glu Ser Ile Gln
    450                 455                 460
Glu Ala Leu Asp Phe Arg Arg Ala Met Arg Lys Val Glu Gly Asp Phe
465                 470                 475                 480
Glu Ala Gly Asn Asn Gly Asp Trp Trp Phe Lys Val Trp Gly Pro Asp
                485                 490                 495
Thr Leu Asn Asp Glu Gly Met Pro Glu Arg Glu Gln Trp Met Leu Lys
            500                 505                 510
Ala Asn Glu Arg Trp His Gly Phe Gly Asp Leu Ala Asp Gly Phe Asn
        515                 520                 525
Leu Leu Asp Pro Ile Lys Ala Thr Ile Thr Pro Gly Leu Asp Val
    530                 535                 540
Asp Gly Glu Phe Ser Asp Arg Gly Ile Pro Ala Ala Ile Val Thr Lys
545                 550                 555                 560
Tyr Leu Ala Glu His Gly Ile Ile Ile Glu Lys Thr Gly Leu Tyr Ser
                565                 570                 575
Phe Phe Ile Met Phe Thr Ile Gly Ile Thr Lys Gly Arg Trp Asn Ser
            580                 585                 590
Leu Val Thr Glu Leu Gln Gln Phe Lys Asp Asp Tyr Asp Gln Asn Gln
        595                 600                 605
Pro Leu Trp Arg Val Leu Pro Glu Phe Val Gly Lys His Pro Gln Tyr
    610                 615                 620
Glu Arg Met Gly Leu Arg Asp Leu Cys Asp Ala Val His Ser Val Tyr
625                 630                 635                 640
Lys Ala Asn Asp Val Ala Arg Val Thr Thr Glu Met Tyr Leu Ser Asp
                645                 650                 655
Met Glu Pro Ala Met Lys Pro Ser Asp Ala Trp Ser Met Met Ala His
            660                 665                 670
Arg Glu Ile Glu Arg Val Pro Val Asp Asp Leu Glu Gly Arg Val Thr
        675                 680                 685
```

```
Ala Ile Leu Leu Thr Pro Tyr Pro Gly Ile Pro Leu Ile Pro
    690             695             700

Gly Glu Arg Phe Asn Arg Thr Ile Val Gln Tyr Leu Lys Phe Ala Arg
705                 710             715                 720

Glu Phe Asn Lys Leu Phe Pro Gly Phe Glu Thr Asp Val His Gly Leu
                725             730                 735

Val Glu Glu Val Asp Gly Arg Lys Ala Tyr Phe Val Asp Cys Val
        740             745             750

Lys Gln Gly Ser
    755
```

<210> SEQ ID NO 9
<211> LENGTH: 454
<212> TYPE: PRT
<213> ORGANISM: Rhodobacter capsulatus

<400> SEQUENCE: 9

```
Met Lys Thr Ile Ile Glu Pro Phe Arg Ile Lys Ser Val Glu Pro Ile
1               5                   10                  15

Arg Leu Thr Ser Arg Pro Glu Arg Glu Arg Leu Ala Arg Ala Ala Gly
            20                  25                  30

Tyr Asn Leu Phe Gly Leu His Ser Asp Asp Val Leu Ile Asp Leu Leu
        35                  40                  45

Thr Asp Ser Gly Thr Gly Ala Met Ser Ser Leu Gln Trp Ala Ala Val
    50                  55                  60

Met Gln Gly Asp Glu Ser Tyr Ala Gly Ser Pro Ser Phe Phe Arg Phe
65                  70                  75                  80

Glu Ala Ala Val Gln Asn Leu Met Pro Phe Lys His Ile Ile Pro Thr
                85                  90                  95

His Gln Gly Arg Ala Ala Glu Ala Ile Leu Phe Ser Ile Phe Gly Gly
            100                 105                 110

Lys Gly Arg Arg Ile Pro Ser Asn Thr His Phe Asp Thr Thr Arg Gly
        115                 120                 125

Asn Ile Glu Ala Ser Gly Ala Thr Gly Asp Asp Leu Val Ile Ala Glu
    130                 135                 140

Gly Lys Asp Pro Gln Asn Leu His Pro Phe Lys Gly Asn Met Asp Leu
145                 150                 155                 160

Ala Arg Leu Glu Ala Tyr Leu Glu Ala His Ala Glu Val Pro Leu
                165                 170                 175

Val Met Ile Thr Ile Thr Asn Asn Ala Gly Gly Gln Pro Val Ser
            180                 185                 190

Leu Ala Asn Ile Arg Ala Val Ala Asp Leu Ala His Arg Tyr Gly Lys
        195                 200                 205

Pro Phe Val Ile Asp Gly Cys Arg Phe Ala Glu Asn Ala Trp Phe Ile
    210                 215                 220

Lys Thr Arg Glu Glu Gly Gln Ala Asp Arg Ser Ile Pro Glu Ile Val
225                 230                 235                 240

Arg Asp Cys Phe Ala Val Ala Asp Gly Met Thr Met Ser Ala Lys Lys
                245                 250                 255

Asp Ala Phe Gly Asn Ile Gly Gly Trp Leu Ala Leu Asn Asp Asp Asp
            260                 265                 270

Leu Ala Glu Glu Ala Arg Gly His Leu Ile Arg Thr Glu Gly Phe Pro
        275                 280                 285

Thr Tyr Gly Gly Leu Ala Gly Arg Asp Leu Asp Ala Leu Ala Gln Gly
```

```
              290                 295                 300
Leu Val Glu Ile Val Asp Glu Asp Tyr Leu Arg Tyr Arg Ile Arg Thr
305                 310                 315                 320

His Gln Tyr Ile Val Glu Arg Leu Asp Ala Met Gly Val Pro Val Val
                325                 330                 335

Lys Pro Ala Gly Gly His Ala Val Phe Ile Asp Ala Arg Ala Trp Leu
            340                 345                 350

Ser His Ile Pro Pro Leu Glu Tyr Pro Gly Gln Ala Leu Ala Val Ala
            355                 360                 365

Leu Tyr Glu Ile Ala Gly Val Arg Ser Cys Glu Ile Gly Thr Ala Met
370                 375                 380

Phe Gly Arg Gln Pro Asp Gly Ser Glu Lys Pro Ala Ala Met Asp Leu
385                 390                 395                 400

Val Arg Leu Ala Phe Pro Arg Arg Thr Tyr Thr Gln Ser His Ala Asp
                405                 410                 415

Tyr Ile Val Glu Ala Phe Glu Glu Leu Ala Ala Thr Lys Asp Ala Leu
                420                 425                 430

Arg Gly Tyr Arg Ile Val Lys Glu Pro Lys Leu Met Arg His Phe Thr
            435                 440                 445

Cys Arg Phe Glu Lys Leu
    450

<210> SEQ ID NO 10
<211> LENGTH: 645
<212> TYPE: PRT
<213> ORGANISM: Sulfurospirillum multivorans

<400> SEQUENCE: 10

Met Asn Asn Gln Lys Ser Thr Ile Asp Thr Ser Lys Phe Asp Asn Val
1               5                   10                  15

Leu Asp Ser Ser Lys Thr Phe Val Asp His Glu Pro Asp Ser Ser Lys
                20                  25                  30

Glu Ile Gln Arg Asn Thr Pro Gln Lys Thr Met Pro Phe Ser Asp Gln
            35                  40                  45

Ile Gly Asn Tyr Gln Arg Asn Arg Gly Ile Pro Ala Tyr Ser Tyr Asp
        50                  55                  60

Glu Ser Lys Val Tyr Ile Val Gly Ser Gly Ile Ala Gly Leu Ser Ala
65                  70                  75                  80

Ala Phe Tyr Leu Ile Arg Asp Gly Arg Ile Pro Ala Gln Asn Ile Thr
                85                  90                  95

Phe Leu Glu Lys Leu Ser Val Glu Gly Gly Ser Met Asp Gly Ala Gly
            100                 105                 110

Asp Ala Arg Glu Gly Tyr Ile Ile Arg Gly Gly Arg Glu Met Asp Met
        115                 120                 125

Thr Tyr Glu Asn Leu Trp Asp Leu Phe Gln Asp Val Pro Ala Val Glu
130                 135                 140

Leu Pro Glu Pro Tyr Ser Val Leu Asp Glu Tyr Arg Leu Leu Asn Asp
145                 150                 155                 160

Asn Asp Ser Asn Tyr Ser Lys Ala Arg Phe Ile His Asn Lys Gly His
                165                 170                 175

Ile Thr Asp Phe Ser Lys Phe Gly Leu Ser Lys Lys Asp Gln Leu Ala
            180                 185                 190

Ile Ile Lys Leu Leu Leu Lys Lys Lys Glu Asp Leu Asp Asp Val Thr
        195                 200                 205
```

-continued

```
Ile Gln Asp Tyr Phe Ser Glu Ser Phe Leu Ala Ser Asp Phe Trp Thr
210                 215                 220
Leu Trp Arg Thr Met Phe Ala Phe Glu Asn Trp His Ser Val Leu Glu
225                 230                 235                 240
Cys Lys Leu Tyr Met His Arg Phe Leu His Val Leu Asp Gly Met Lys
                245                 250                 255
Asp Leu Ser Ala Leu Val Phe Pro Lys Tyr Asn Gln Tyr Asp Thr Phe
            260                 265                 270
Ile Ala Pro Leu Arg Lys Leu Leu Gln Glu Lys Gly Val Gln Phe Gln
        275                 280                 285
Phe Asp Thr Leu Val Glu Asp Leu Glu Ile Thr Met Thr His Asn Glu
290                 295                 300
Lys Ile Val Glu Asn Ile Val Thr Ile His Asn Glu Thr Ser Ser Lys
305                 310                 315                 320
Ile Ala Val Gly Arg Asp Asp Tyr Val Ile Val Thr Thr Gly Ser Met
                325                 330                 335
Thr Glu Asp Thr Phe Tyr Gly Asp Asn His Asn Ala Pro Ile Ile Ser
            340                 345                 350
Ile Asp Asn Thr Thr Ser Gly Gln Ser Ser Gly Trp Lys Leu Trp Lys
        355                 360                 365
Asn Leu Ala Lys Lys Ser Glu Val Phe Gly Lys Pro Glu Lys Phe Cys
370                 375                 380
Ser Thr Ile Glu His Ser Ser Trp Glu Ser Ala Thr Leu Thr Cys Lys
385                 390                 395                 400
Pro Ser Ala Phe Val Glu Lys Leu Lys Lys Leu Ser Val Asn Asp Pro
                405                 410                 415
Tyr Ser Gly Lys Thr Val Thr Gly Gly Ile Ile Thr Ile Thr Asp Ser
            420                 425                 430
Asn Trp Leu Met Ser Phe Thr Cys Asn Arg Gln Pro His Phe Ile Glu
        435                 440                 445
Gln Pro Asp Asp Ile Leu Val Ile Trp Leu Tyr Ala Leu Phe Met Asp
450                 455                 460
Lys Glu Gly Asn Tyr Val Lys Lys Pro Met Pro Glu Cys Ser Gly Asp
465                 470                 475                 480
Glu Ile Leu Thr Glu Leu Cys Tyr His Leu Gly Ile Lys Asp Asp Leu
                485                 490                 495
Glu Asn Val Leu Lys Asn Thr Ile Val Arg Thr Ala Phe Met Pro Tyr
            500                 505                 510
Ile Thr Ser Met Phe Met Pro Arg Ala Lys Gly Asp Arg Pro Arg Ile
        515                 520                 525
Val Pro Lys Gly Cys Lys Asn Leu Gly Leu Ile Gly Gln Phe Val Glu
530                 535                 540
Thr Asn Asn Asp Ile Val Phe Thr Met Glu Ser Ser Ile Arg Thr Ala
545                 550                 555                 560
Arg Ile Ala Val Tyr Thr Leu Leu Asn Leu Asn Lys Gln Val Pro Asp
                565                 570                 575
Ile Asn Pro Leu Gln Tyr Asp Ile Arg Gln Leu Leu Lys Ala Val Lys
            580                 585                 590
Ser Leu Asn Asp Asp Gln Pro Phe Ile Gly Glu Gly Ile Leu Arg Lys
        595                 600                 605
Phe Leu Lys Asp Thr Tyr Tyr Glu Tyr Ile Leu Pro Pro Met Ser Lys
610                 615                 620
Glu Ser Glu Gln Glu Ser Ser Phe Met Glu His Ile Glu Lys Ile Lys
```

```
                625                 630                 635                 640

Glu Trp Ile Leu Arg
            645

<210> SEQ ID NO 11
<211> LENGTH: 20
<212> TYPE: DNA
<213> ORGANISM: artificial sequence
<220> FEATURE:
<223> OTHER INFORMATION: synthetic polynucleotide

<400> SEQUENCE: 11
atggctctca tcgttcacaa                                                     20

<210> SEQ ID NO 12
<211> LENGTH: 19
<212> TYPE: DNA
<213> ORGANISM: artificial sequence
<220> FEATURE:
<223> OTHER INFORMATION: synthetic polynucleotide

<400> SEQUENCE: 12
tcacgcctgt tccagttcg                                                      19

<210> SEQ ID NO 13
<211> LENGTH: 25
<212> TYPE: DNA
<213> ORGANISM: artificial sequence
<220> FEATURE:
<223> OTHER INFORMATION: synthetic polynucleotide

<400> SEQUENCE: 13
gttctgggac gaggtgacgc tgcag                                               25

<210> SEQ ID NO 14
<211> LENGTH: 24
<212> TYPE: DNA
<213> ORGANISM: artificial sequence
<220> FEATURE:
<223> OTHER INFORMATION: synthetic polynucleotide

<400> SEQUENCE: 14
gtatgcggcc aggttgcgtg ccag                                                24

<210> SEQ ID NO 15
<211> LENGTH: 28
<212> TYPE: DNA
<213> ORGANISM: artificial sequence
<220> FEATURE:
<223> OTHER INFORMATION: synthetic polynucleotide

<400> SEQUENCE: 15
atgaactccc tgcctgacac cgcttccc                                            28

<210> SEQ ID NO 16
<211> LENGTH: 30
<212> TYPE: DNA
<213> ORGANISM: artificial sequence
<220> FEATURE:
<223> OTHER INFORMATION: synthetic polynucleotide

<400> SEQUENCE: 16
tcacactgcg ttgaatacgt gacgcaccag                                          30

<210> SEQ ID NO 17
```

```
<211> LENGTH: 28
<212> TYPE: DNA
<213> ORGANISM: artificial sequence
<220> FEATURE:
<223> OTHER INFORMATION: synthetic polynucleotide

<400> SEQUENCE: 17
tgaagcgccc aggaagcatt ctggacag                                28

<210> SEQ ID NO 18
<211> LENGTH: 25
<212> TYPE: DNA
<213> ORGANISM: artificial sequence
<220> FEATURE:
<223> OTHER INFORMATION: synthetic polynucleotide

<400> SEQUENCE: 18
cgcgcgaaga acccgcccgt ttcac                                   25

<210> SEQ ID NO 19
<211> LENGTH: 26
<212> TYPE: DNA
<213> ORGANISM: artificial sequence
<220> FEATURE:
<223> OTHER INFORMATION: synthetic polynucleotide

<400> SEQUENCE: 19
cctcgtcgcc tacgtcgaac gcatgc                                  26

<210> SEQ ID NO 20
<211> LENGTH: 25
<212> TYPE: DNA
<213> ORGANISM: artificial sequence
<220> FEATURE:
<223> OTHER INFORMATION: synthetic polynucleotide

<400> SEQUENCE: 20
cagcacgccg atctgcacgg cgttg                                   25

<210> SEQ ID NO 21
<211> LENGTH: 27
<212> TYPE: DNA
<213> ORGANISM: artificial sequence
<220> FEATURE:
<223> OTHER INFORMATION: synthetic polynucleotide

<400> SEQUENCE: 21
ccgagtggga aggctatgtg acgctgg                                 27

<210> SEQ ID NO 22
<211> LENGTH: 24
<212> TYPE: DNA
<213> ORGANISM: artificial sequence
<220> FEATURE:
<223> OTHER INFORMATION: synthetic polynucleotide

<400> SEQUENCE: 22
gtggtagtgg cagccgagcc ggtg                                    24
```